(12) United States Patent
Sakuma et al.

(10) Patent No.: US 9,873,683 B2
(45) Date of Patent: Jan. 23, 2018

(54) P2X4 RECEPTOR ANTAGONIST

(71) Applicants: NIPPON CHEMIPHAR CO., LTD., Tokyo (JP); KYUSHU UNIVERSITY, Fukuoka (JP)

(72) Inventors: Shogo Sakuma, Saitama (JP); Kunio Kobayashi, Saitama (JP); Masatoshi Ushioda, Tokyo (JP); Daisuke Saito, Tokyo (JP); Toshiyasu Imai, Tokyo (JP); Kazuhide Inoue, Tokyo (JP)

(73) Assignees: NIPPON CHEMIPHAR CO., LTD, Tokyo (JP); KYUSHU UNIVERSITY, Fukuoka (JP)

( * ) Notice: Subject to any disclaimer, the term of this patent is extended or adjusted under 35 U.S.C. 154(b) by 0 days.

(21) Appl. No.: 14/903,382

(22) PCT Filed: Jul. 11, 2014

(86) PCT No.: PCT/JP2014/068541
§ 371 (c)(1),
(2) Date: Apr. 22, 2016

(87) PCT Pub. No.: WO2015/005468
PCT Pub. Date: Jan. 15, 2015

(65) Prior Publication Data
US 2016/0244434 A1 Aug. 25, 2016

(30) Foreign Application Priority Data

Jul. 12, 2013 (JP) ................. 2013-146213

(51) Int. Cl.
*C07D 243/12* (2006.01)
*C07D 401/12* (2006.01)
(Continued)

(52) U.S. Cl.
CPC ......... *C07D 403/10* (2013.01); *C07D 401/04* (2013.01); *C07D 401/14* (2013.01);
(Continued)

(58) Field of Classification Search
CPC .. C07D 243/12; C07D 401/12; C07D 403/12; C07D 405/12; C07D 409/12
See application file for complete search history.

(56) References Cited

U.S. PATENT DOCUMENTS

2005/0074819 A1  4/2005  Inoue et al.
2011/0319610 A1  12/2011  Sakuma et al.
(Continued)

FOREIGN PATENT DOCUMENTS

EP  2397480 A1  12/2011
EP  2597088 A1  5/2013
(Continued)

OTHER PUBLICATIONS

Jeffrey A. M. Coull et al., "BDNF from microglia causes the shift in neuronal anion gradient underlying neuropathic pain", Nature, vol. 438, pp. 1017-1021, 2005.
M. Tsuda et al., "P2X4 receptors induced in spinal microglia gate tactile allodynia after nerve injury", Nature, vol. 424, pp. 778-783, 2003.
Kenichiro Nagata et al., "Inhibitory effects of antidepressants on P2X4 receptor: a novel mechanism in neuropathic pain relief", The 49th Convention of The Japanese Society for Neurochemistry, Program Lecture Abstract P3-N-114, 2006.
Buell et al., "An antagonist-insensitive P2x receptor expressed in epithelia and brain", The EMBO Journal, vol. 15, No. 1, pp. 55-62, 1996.
Seguela et al., "A Novel Neuronal P2x ATP Receptor Ion Channel with Widespread Distribution in the Brain", The Journal of Neuroscience, Jan. 15, 1996, pp. 448-455.
Bo et al., "A P2X purinoceptor cDNA conferring a novel pharmacological profile", FEBS Letters 375, 1995, pp. 129-133.
Soto et al., "P2X4: An ATP-activated ionotropic receptor cloned from rat brain", Proc. Natl. Acad. Sci. USA, vol. 93, pp. 3684-3688, 1996.
Wang et al., "Cloning and Pharmacological Characterization of a Fourth P2X Receptor Subtype Widely Expressed in Brain and Peripheral Tissues Including Various Endocrine Tissues", Biochemical and Biophysical Research Communications, vol. 220, pp. 196-202, 1996.

(Continued)

*Primary Examiner* — Savitha Rao
(74) *Attorney, Agent, or Firm* — Greenblum & Bernstein, P.L.C.

(57) ABSTRACT

The present invention relates to a compound represented by the following general formula (II), wherein, in the formula, $R^{1a}$ to $R^{6a}$ represent hydrogen atom, an alkyl group having 1 to 8 carbon atoms, and the like, $X^a$ represents C or N, $Y^a$ represents N or C(=O), provided that when $X^a$ is C, $Y^a$ represents N, and when $X^a$ is N, $Y^a$ represents C(=O), the double line consisting of the solid line and the broken line represents a single bond or double bond, $A^a$ represents benzene ring, pyridine ring, and the like, $D^a$ represents tetrazole ring, imidazole ring, and the like, $E^a$ represents $-(CR^{9a}R^{10a})_p-T^a-$, and $G^a$ represents benzene ring, pyridine ring, and the like, which has a P2X4 receptor antagonistic activity.

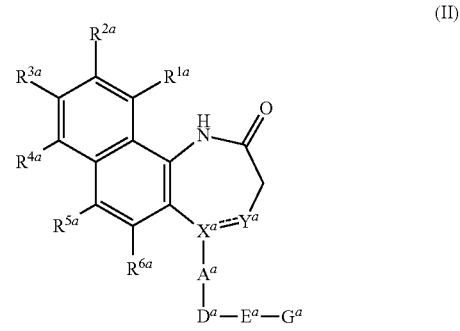

22 Claims, 1 Drawing Sheet

(51) Int. Cl.
| | |
|---|---|
| *C07D 403/12* | (2006.01) |
| *C07D 405/12* | (2006.01) |
| *C07D 409/12* | (2006.01) |
| *C07D 403/10* | (2006.01) |
| *C07D 401/04* | (2006.01) |
| *C07D 403/08* | (2006.01) |
| *C07D 401/14* | (2006.01) |
| *C07D 403/14* | (2006.01) |
| *C07D 405/14* | (2006.01) |
| *C07D 409/14* | (2006.01) |

(52) U.S. Cl.
CPC ......... *C07D 403/08* (2013.01); *C07D 403/14* (2013.01); *C07D 405/14* (2013.01); *C07D 409/14* (2013.01)

(56) References Cited

U.S. PATENT DOCUMENTS

| | | |
|---|---|---|
| 2013/0172550 A1 | 7/2013 | Sakuma et al. |
| 2013/0178625 A1 | 7/2013 | Ushioda et al. |

FOREIGN PATENT DOCUMENTS

| | | |
|---|---|---|
| EP | 2636414 A1 | 9/2013 |
| JP | 2005-74819 A | 3/2005 |
| JP | 2013-209292 A | 10/2013 |
| WO | 2004041258 A2 | 5/2004 |
| WO | 2004/085440 A1 | 10/2004 |
| WO | 2008/023847 A1 | 2/2008 |
| WO | 2010/090300 A1 | 8/2010 |
| WO | 2010/093061 A1 | 8/2010 |
| WO | 2012/008478 A1 | 1/2012 |
| WO | 2012/011549 A1 | 1/2012 |
| WO | 2012/014910 A1 | 2/2012 |
| WO | 2012/017876 A1 | 2/2012 |
| WO | 2012/060397 A1 | 5/2012 |
| WO | 2012-060397 A1 | 5/2012 |
| WO | 2012-161301 A1 | 11/2012 |
| WO | 2012/161301 A1 | 11/2012 |
| WO | 2013/105608 A1 | 7/2013 |

OTHER PUBLICATIONS

International Search Report issued with respect to application No. PCT/2014/068541, dated Oct. 14, 2014.
International Preliminary Report on Patentability issued with respect to application No. PCT/2014/068541, dated Jan. 12, 2016.
European Search Report issued with respect to Application No. 14822292.0, dated Jan. 3, 2017.
Examination Report from Australian Application No. 2014288116 dated Nov. 23, 2017.

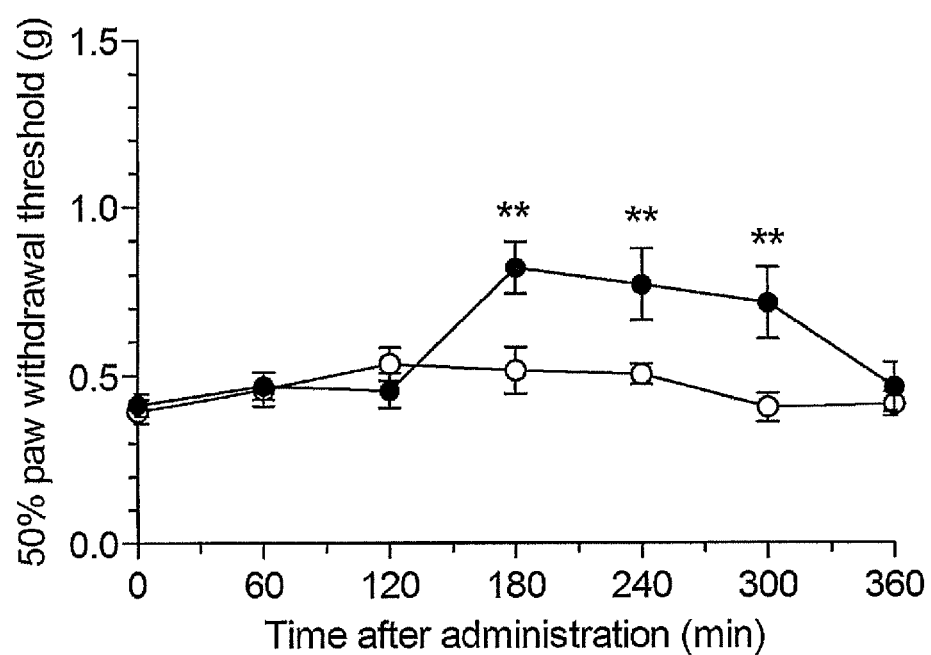

P2X4 RECEPTOR ANTAGONIST

TECHNICAL FIELD

The present invention relates to a diazepine derivative having a P2X4 receptor antagonist activity.

BACKGROUND ART

The ATP receptors are roughly classified into the P2X family of the ion channel type receptors, and the P2Y family of the G protein coupling type receptors, and seven kinds ($P2X_1$ to $P2X_7$) and eight kinds ($P2Y_1$, $P2Y_2$, $P2Y_4$, $P2Y_6$, and $P2Y_{11}$ to $P2Y_{14}$) of subtypes have so far been reported for each family.

The $P2X_4$ receptor (Genebank No. X87763), a subtype of the P2X family, has been reported to be widely expressed in the central nervous system, and the like (Non-patent documents 1 to 5).

The onset mechanisms of chronic or intractable pains including neuropathic pain have not been fully elucidated, and if non-steroidal anti-inflammatory drugs (NSAIDs) and morphine are not effective for such a pain, no therapy is available for that pain. Therefore, very heavy physical and mental burdens are given to patients and people around them. Neuropathic pain is often caused by injury of a peripheral nerve or the central nerve, and it is caused by, for example, after-trouble of operation, cancer, spinal cord injury, herpes zoster, diabetic neuritis, trigeminal neuralgia, and the like.

Recently, Inoue et al. verified the involvement of the P2X receptor in neuropathic pain by using a spinal nerve-damaged animal model in which allodynia can be detected, and they described that nerve-damaged type unusual pain (especially allodynia) is induced through the $P2X_4$ receptor expressed in the microglia cells of the spinal cord (Non-patent documents 6 and 7, and Patent document 1).

Therefore, a substance that inhibits the activity of the P2X4 receptor is expected to be a prophylactic or therapeutic agent for pains of nociceptive pain, inflammatory pain, and neuropathic pain caused by after-trouble of operation, cancers, spinal cord injury, herpes zoster, diabetic neuritis, trigeminal neuralgia, and the like.

Patent document 2 reported that a benzofuro-1,4-diazepin-2-one derivative represented by the following general formula (A):

[Formula 1]

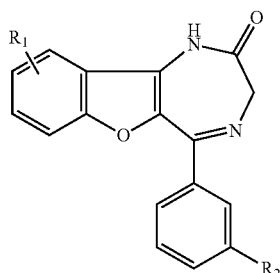

(A)

(in the formula, $R_1$ is a halogen, and $R_2$ is hydrogen, a halogen, nitro, cyano, C(O)—$OR_3$, C(O)—$NR_4R_5$, $SO_2$—$OR_3$, or $SO_2$—$NR_4R_5$, or $R_1$ is hydrogen, and $R_2$ is a halogen, nitro, cyano, C(O)—$OR_3$, C(O)—$NR_4R_5$, $SO_2$—$OR_3$, or $SO_2$—$NR_4R_5$) has a P2X4 receptor antagonist activity.

It was also reported that paroxetine, which is an antidepressant, has a P2X4 receptor antagonist activity (Non-patent document 8).

The inventors of the present invention also found that a naphtho[1,2-e][1,4]diazepin-2-one derivative represented by the following formula (B):

[Formula 2]

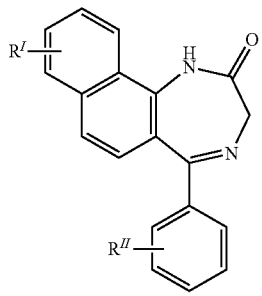

(B)

(in the formula, $R^I$ represents hydrogen, a lower alkyl, a lower alkoxy, and the like, and $R^{II}$ represents hydroxy, a lower alkyl, a lower alkoxy, tetrazolyl group, and the like), a naphtho[1,2-b][1,4]diazepin-2,4-dione derivative represented by the following general formula (C):

[Formula 3]

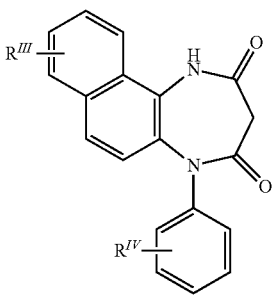

(C)

(in the formula, $R^{III}$ represents hydrogen, a lower alkyl, a lower alkoxy, and the like, and $R^{IV}$ represents hydrogen, a lower alkyl, a lower alkoxy, tetrazolyl group, and the like), and related compounds thereof have a P2X4 receptor antagonist activity, and filed patent applications therefor (Patent documents 3 to 10).

Patent documents 3 to 10 mentioned above do not specifically describe any naphtho[1,2-e][1,4]diazepin-2-one derivative represented by the aforementioned formula (B), nor naphtho[1,2-b][1,4]diazepin-2,4-dione derivative represented by the aforementioned general formula (C) in which tetrazole group or the like substitutes on the phenyl group or the like at the 5-position, and benzyl group or the like substitutes on the tetrazole group or the like.

PRIOR ART REFERENCES

Patent Documents

Patent document 1: Published U.S. Patent Application No. 20050074819

Patent document 2: WO2004/085440
Patent document 3: WO2008/023847
Patent document 4: WO2010/093061
Patent document 5: WO2010/090300
Patent document 6: WO2012/008478
Patent document 7: WO2012/11549
Patent document 8: WO2012/14910
Patent document 9: WO2012/17876
Patent document 10: WO2013/105608

Non-Patent Documents

Non-patent document 1: Buell et al. (1996) EMBO J., 15:55-62
Non-patent document 2: Seguela et al. (1996) J. Neurosci., 16:448-455
Non-patent document 3: Bo et al. (1995) FEBS Lett., 375:129-133
Non-patent document 4: Soto et al. (1996) Proc. Natl. Acad. Sci. USA, 93:3684-3788
Non-patent document 5: Wang et al. (1996) Biochem. Res. Commun., 220:196-202
Non-patent document 6: M. Tsuda et al. (2003) Nature, 424, 778-783
Non-patent document 7: Jeffrey A. M. Coull et al. (2005) Nature, 438, 1017-1021
Non-patent document 8: The 49th Convention of The Japanese Society for Neurochemistry (2006), Program Lecture Abstract P3-N-114

SUMMARY OF THE INVENTION

Object to be Achieved by the Invention

So far to date, any safe medicament in the form of a preparation for oral administration has not been provided which can be easily taken and has a superior P2X4 receptor antagonist activity.

An object of the present invention is to provide a diazepine derivative represented by the following general formula (I) or (II) and having a P2X4 receptor antagonist activity.

Means for Achieving the Object

The present invention thus relates to a compound represented by the following general formula (I), a tautomer or a stereoisomer of the compound, or a pharmacologically acceptable salt thereof, or a solvate of any of the foregoing:

[Formula 4]

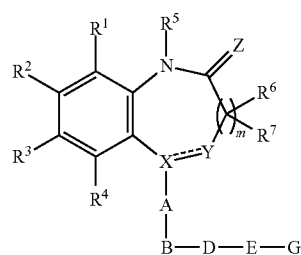

(I)

(wherein, in the formula, $R^1$ and $R^2$ may be the same or different, and represent hydrogen atom, an alkyl group having 1 to 8 carbon atoms, a cycloalkyl group having 3 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acylamino group having 2 to 8 carbon atoms, carboxyl group, an acyl group having 2 to 8 carbon atoms, an alkoxycarbonyl group (the alkoxy moiety has 1 to 8 carbon atoms), a phenyl group which may be substituted, a pyridyl group which may be substituted, or an aralkyl group (the aryl moiety has 6 to 10 carbon atoms, and the alkylene moiety has 1 to 8 carbon atoms), or $R^1$ and $R^2$ may bind together to form a condensed ring selected from naphthalene ring, quinoline ring, isoquinoline ring, tetrahydronaphthalene ring, indane ring, tetrahydroquinoline ring and tetrahydroisoquinoline ring together with the benzene ring to which they bind, the ring constituted by $R^1$ and $R^2$, bound to each other, together with the carbon atoms to which $R^1$ and $R^2$ bind, may be substituted with the same or different 1 to 4 substituents selected from an alkyl group having 1 to 8 carbon atoms, a cycloalkyl group having 3 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acylamino group having 2 to 8 carbon atoms, carboxyl group, an acyl group having 2 to 8 carbon atoms, an alkoxycarbonyl group (the alkoxy moiety has 1 to 8 carbon atoms), and an aralkyl group (the aryl moiety has 6 to 10 carbon atoms, and the alkylene moiety has 1 to 8 carbon atoms), $R^3$ and $R^4$ may be the same or different, and represent hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acylamino group having 2 to 8 carbon atoms, carboxyl group, an acyl group having 2 to 8 carbon atoms, an alkoxycarbonyl group (the alkoxy moiety has 1 to 8 carbon atoms), or an aralkyl group (the aryl moiety has 6 to 10 carbon atoms, and the alkylene moiety has 1 to 8 carbon atoms), $R^5$ represents hydrogen atom, an alkyl group having 1 to 8 carbon atoms, an alkenyl group having 2 to 8 carbon atoms, an alkyl group having 1 to 8 carbon atoms and substituted with 1 to 3 halogen atoms, an alkyl group having 1 to 8 carbon atoms and substituted with hydroxyl group, or an aralkyl group (the aryl moiety has 6 to 10 carbon atoms, and the alkylene moiety has 1 to 8 carbon atoms), $R^6$ and $R^7$ may be the same or different, and represent hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, or amino group, X represents C or N, Y represents N or C(═O), provided that when X is C, Y represents N, and when X is N, Y represents C(═O), the double line consisting of the solid line and the broken line represents a single bond or double bond, Z represents O, S or NH, A represents benzene ring, pyridine ring, pyrimidine ring, pyridazine ring, thiophene ring, furan ring, pyrazole ring, imidazole ring, quinoline ring, benzimidazole ring, or indane ring, which may have the same or different 1 to 4 substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, and a dialkylamino group having 2 to 8 carbon atoms, as a substituent, B represents O, S, $NR^8$, or an atomic bond, wherein $R^8$ represents hydrogen atom, or an alkyl group having 1 to 8 carbon atoms, D represents benzene ring, pyridine ring, pyrimidine ring, pyridazine ring, thiophene ring, furan ring, tetrazole ring, imidazole ring, imidazoline ring, triazole ring, thiazole ring, oxazole ring, isoxazole ring, pyrazole ring, pyrrole ring, pyrrolidine ring, piperazine ring, piperidine ring, or a 5- to 8-membered cycloalkyl ring, which may have the same or different 1 to 4 substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, and a dialkylamino group having 2 to 8 carbon atoms, as a substituent, E represents —$(CR^9R^{10})_n$-T-, wherein $R^9$ and $R^{10}$ may be the same or different, and represent hydrogen atom, hydroxyl group, or an alkyl group having 1 to 8 carbon atoms, or $R^9$ and $R^{10}$ may bind together to form an ethylene chain, n represents an integer of 0 to 8, and T represents O, S, $NR^{11}$, or an atomic bond, wherein $R^{11}$ represents hydrogen atom, or an alkyl group having 1 to 8 carbon atoms, G represents benzene ring, pyridine ring, imidazole ring, pyrrole ring, pyrazole ring, thiophene ring, furan ring, thiazole ring, oxazole ring, pyrimidine ring, pyridazine ring, pyrazine ring, naphthalene ring, quinoline ring, quinazoline ring, indole ring, indoline ring, piperazine ring, piperidine ring, morpholine ring, or a 5- to 8-membered cycloalkyl ring, which may have the same or different 1 to 5 substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, carbamoyl group, and methanesulfonyl group, as a substituent, and m represents an integer of 0 to 2).

The present invention also relates to a compound represented by the following general formula (II), a tautomer or a stereoisomer of the compound, or a pharmacologically acceptable salt thereof, or a solvate of any of the foregoing:

[Formula 5]

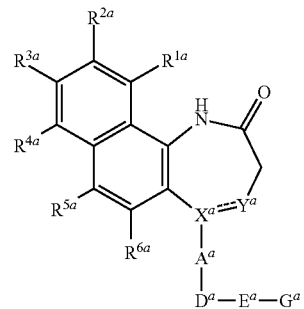

(II)

(wherein, in the formula, $R^{1a}$, $R^{2a}$, $R^{3a}$, $R^{4a}$, $R^{5a}$ and $R^{6a}$ may be the same or different, and represent hydrogen atom, an alkyl group having 1 to 8 carbon atoms, a cycloalkyl group having 3 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acylamino group having 2 to 8 carbon atoms, carboxyl group, an acyl group having 2 to 8 carbon atoms, an alkoxycarbonyl group (the alkoxy moiety has 1 to 8 carbon atoms), a phenyl group which may be substituted, a pyridyl group which may be substituted, or an aralkyl group (the aryl moiety has 6 to 10 carbon atoms, and the alkylene moiety has 1 to 8 carbon atoms), $X^a$ represents C or N, $Y^a$ represents N or C(═O), provided that when $X^a$ is C, $Y^a$ represents N, and when $X^a$ is N, $Y^a$ represents C(═O), the double line consisting of the solid line and the broken line represents a single bond or double bond, $A^a$ represents benzene ring, pyridine ring, pyrimidine ring, pyridazine ring, thiophene ring, furan ring, pyrazole ring, imidazole ring, quinoline ring, benzimidazole ring, or indane ring, which may have the same or different 1 to 4 substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, and a dialkylamino group having 2 to 8 carbon atoms, as a substituent, $D^a$ represents benzene ring, pyridine ring, pyrimidine ring, pyridazine ring, thiophene ring, furan ring, tetrazole ring, imidazole ring, imidazoline ring, triazole ring, thiazole ring, oxazole ring, isoxazole ring, pyrazole ring, pyrrole ring, pyrrolidine ring, piperazine ring, piperidine ring, or a 5- to 8-membered cycloalkyl ring, which may have the same or different 1 to 4 substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, and a dialkylamino group having 2 to 8 carbon atoms, as a substituent, $E^a$ represents —$(CR^{9a}R^{10a})_p$-$T^a$-, wherein $R^{9a}$ and $R^{10a}$ are the same or different, and represent hydrogen atom, hydroxyl group, or an alkyl group having 1 to 8 carbon atoms, or $R^{9a}$ and $R^{10a}$ may bind together to form an ethylene chain, p represents an integer of 0 to 8, and $T^a$ represents O, S, $NR^{11a}$, or an atomic bond, wherein $R^{11a}$ represents hydrogen atom, or an alkyl group having 1 to 8 carbon atoms, and $G^a$ represents benzene ring, pyridine ring, imidazole ring, pyrrole ring, pyrazole ring, thiophene ring, furan ring, thiazole ring, oxazole ring, pyrimidine ring, pyridazine ring, pyrazine ring, naphthalene ring, quinoline ring, quinazoline ring, indole ring, indoline ring, piperazine ring, piperidine ring, morpholine ring, or a 5- to 8-membered cycloalkyl ring, which may have the same or different 1 to 5 substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, carbamoyl group, and methanesulfonyl group, as a substituent).

The present invention also relates to a P2X4 receptor antagonist containing a compound represented by the aforementioned general formula (I) or (II), a tautomer or a stereoisomer of the compound, or a pharmacologically acceptable salt thereof, or a solvate of any of the foregoing as an active ingredient.

The present invention further relates to a prophylactic or therapeutic agent for nociceptive pain, inflammatory pain, or neuropathic pain containing a compound represented by the aforementioned general formula (I) or (II), a tautomer or a stereoisomer of the compound, or a pharmacologically acceptable salt thereof, or a solvate of any of the foregoing as an active ingredient.

BRIEF DESCRIPTION OF THE DRAWING

FIG. 1 shows results of measurement of the analgesic activity of the compound of the present invention (Example 86).

MODES FOR CARRYING OUT THE INVENTION

Hereafter, the present invention will be explained in detail.

In this specification, examples of the alkyl group having 1 to 8 carbon atoms include methyl group, ethyl group, propyl group, isopropyl group, butyl group, i-butyl group, t-butyl group, pentyl group, hexyl group, and the like.

Examples of the 5- to 8-membered cycloalkyl ring include cyclopentyl ring, cyclohexyl ring, and the like.

Examples of the cycloalkyl group having 3 to 8 carbon atoms include cyclopropyl group, cyclohexyl group, and the like.

Examples of the alkenyl group having 2 to 8 carbon atoms include allyl group, and the like.

Examples of the alkoxy group having 1 to 8 carbon atoms include methoxy group, ethoxy group, propoxy group, isopropoxy group, butoxy group, i-butoxy group, t-butoxy group, pentyloxy group, hexyloxy group, and the like.

Examples of the alkyl group having 1 to 8 carbon atoms and substituted with 1 to 3 halogen atoms include methyl group, ethyl group, propyl group, isopropyl group, butyl group, t-butyl group, and the like, which are substituted with 1 to 3 of halogen atoms such as fluorine atom, chlorine atom, and bromine atom, and preferred examples include trifluoromethyl group, chloromethyl group, 2-chloroethyl group, 2-bromoethyl group, 2-fluoroethyl group, and the like.

Examples of the alkoxy group having 1 to 8 carbon atoms and substituted with 1 to 3 halogen atoms include methoxy group, ethoxy group, propoxy group, isopropoxy group, butoxy group, t-butoxy group, and the like, which are substituted with 1 to 3 of halogen atoms such as fluorine atom, chlorine atom, and bromine atom, and preferred examples include trifluoromethoxy group, chloromethoxy group, 2-chloroethoxy group, 2-bromoethoxy group, 2-fluoroethoxy group, and the like.

Examples of the halogen atom include fluorine atom, chlorine atom, bromine atom, and the like.

Examples of the alkylamino group having 1 to 8 carbon atoms include methylamino group, ethylamino group, and the like.

Examples of the dialkylamino group having 2 to 8 carbon atoms include dimethylamino group, diethylamino group, and the like.

Examples of the acylamino group having 2 to 8 carbon atoms include acetylamino group.

Examples of the acyl group having 2 to 8 carbon atoms include acetyl group, and the like.

Examples of the alkoxycarbonyl group (the alkoxy moiety has 1 to 8 carbon atoms) include methoxycarbonyl group, and the like.

Examples of the aralkyl group (the aryl moiety has 6 to 10 carbon atoms, and the alkylene moiety has 1 to 8 carbon atoms) include benzyl group, and the like.

Examples of the alkyl group having 1 to 8 carbon atoms and substituted with hydroxyl group include 2-hydroxyethyl group, and the like.

Examples of the substituent of the phenyl group which may be substituted, and the pyridyl group which may be substituted include a halogen atom, an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, and the like.

The expression "$R^9$ and $R^{10}$ may bind together to form an ethylene chain" and "$R^{9a}$ and $R^{10a}$ may bind together to form an ethylene chain" in the definitions of E and $E^a$ included in the aforementioned general formulas (I) and (II) means that E and $E^a$ may contain a double bond.

As the compounds of the present invention represented by the aforementioned general formula (I), the compounds mentioned below are preferred.

(1)

The compound represented by the aforementioned general formula (I), a tautomer or a stereoisomer of the compound, or a pharmacologically acceptable salt thereof, or a solvate of any of the foregoing, wherein m is 1.

(2)

The compound represented by the aforementioned general formula (I) or the compound according to (1) mentioned above, a tautomer or a stereoisomer of the compound, or a pharmacologically acceptable salt thereof, or a solvate of any of the foregoing, wherein $R^1$ and $R^2$ bind together to form naphthalene ring together with the benzene ring to which they bind, and the naphthalene ring may be substituted with the same or different 1 to 4 substituents selected from an alkyl group having 1 to 8 carbon atoms, a cycloalkyl group having 3 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, and a dialkylamino group having 2 to 8 carbon atoms.

(3)

The compound represented by the aforementioned general formula (I) or the compound according to (1) or (2) mentioned above, a tautomer or a stereoisomer of the compound, or a pharmacologically acceptable salt thereof, or a solvate of any of the foregoing, wherein $R^3$ and $R^4$ may be the same or different, and are hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, or a dialkylamino group having 2 to 8 carbon atoms.

(4)

The compound represented by the aforementioned general formula (I) or the compound according to any one of (1) to (3) mentioned above, a tautomer or a stereoisomer of the compound, or a pharmacologically acceptable salt thereof, or a solvate of any of the foregoing, wherein $R^5$ is hydrogen atom.

(5)

The compound represented by the aforementioned general formula (I) or the compound according to any one of (1) to (4) mentioned above, a tautomer or a stereoisomer of the compound, or a pharmacologically acceptable salt thereof, or a solvate of any of the foregoing, wherein $R^6$ and $R^7$ are hydrogen atoms.

(6)

The compound represented by the aforementioned general formula (I) or the compound according to any one of (1) to (5) mentioned above, a tautomer or a stereoisomer of the compound, or a pharmacologically acceptable salt thereof, or a solvate of any of the foregoing, wherein X is N, and Y is C(=O).

(7)

The compound represented by the aforementioned general formula (I) or the compound according to any one of (1) to (6) mentioned above, a tautomer or a stereoisomer of the compound, or a pharmacologically acceptable salt thereof, or a solvate of any of the foregoing, wherein Z is O.

(8)

The compound represented by the aforementioned general formula (I) or the compound according to any one of (1) to (7) mentioned above, a tautomer or a stereoisomer of the compound, or a pharmacologically acceptable salt thereof, or a solvate of any of the foregoing, wherein A is benzene ring, or pyridine ring, which may have the same or different 1 to 4 substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, and a dialkylamino group having 2 to 8 carbon atoms, as a substituent.

(9)

The compound represented by the aforementioned general formula (I) or the compound according to any one of (1) to (8) mentioned above, a tautomer or a stereoisomer of the compound, or a pharmacologically acceptable salt thereof, or a solvate of any of the foregoing, wherein D is tetrazole ring, imidazole ring, imidazoline ring, triazole ring, pyrrole ring, pyrrolidine ring, piperazine ring, or piperidine ring, which may have the same or different 1 to 4 substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, and a dialkylamino group having 2 to 8 carbon atoms, as a substituent.

(10)

The compound represented by the aforementioned general formula (I) or the compound according to any one of (1) to (9) mentioned above, a tautomer or a stereoisomer of the compound, or a pharmacologically acceptable salt thereof, or a solvate of any of the foregoing, wherein B is an atomic bond.

(11)

The compound according to (10) mentioned above, a tautomer or a stereoisomer of the compound, or a pharmacologically acceptable salt thereof, or a solvate of any of the foregoing, wherein D binds to A via nitrogen atom.

(12)

The compound represented by the aforementioned general formula (I) or the compound according to any one of (1) to (11) mentioned above, a tautomer or a stereoisomer of the compound, or a pharmacologically acceptable salt thereof, or a solvate of any of the foregoing, wherein E is an alkylene chain having 1 to 5 carbon atoms.

(13)

The compound represented by the aforementioned general formula (I), or the compound according to any one of (1) to (12) mentioned above, a tautomer or a stereoisomer of the compound, or a pharmacologically acceptable salt thereof, or a solvate of any of the foregoing, wherein G is benzene ring, pyridine ring, imidazole ring, pyrrole ring, pyrazole ring, pyrimidine ring, pyridazine ring, pyrazine ring, or a 5- to 7-membered cycloalkyl ring, which may have the same or different 1 to 5 substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, carbamoyl group, and methanesulfonyl group.

(14)

The compound represented by the aforementioned general formula (I), a tautomer or a stereoisomer of the compound, or a pharmacologically acceptable salt thereof, or a solvate of any of the foregoing, wherein:

$R^1$ and $R^2$ bind together to form naphthalene ring, or indane ring together with the benzene ring to which they bind, and the naphthalene ring, or indane ring may be substituted with the same or different 1 to 4 substituents selected from an alkyl group having 1 to 8 carbon atoms, a cycloalkyl group having 3 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acylamino group having 2 to 8 carbon atoms, carboxyl group, an acyl group having 2 to 8 carbon atoms, an alkoxycarbonyl group (the alkoxy moiety has 1 to 8 carbon atoms), and an aralkyl group (the aryl moiety has 6 to 10 carbon atoms, and the alkylene moiety has 1 to 8 carbon atoms), $R^3$ and $R^4$ may be the same or different, and are hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, an acylamino group having 2 to 8 carbon atoms, carboxyl group, an acyl group having 2 to 8 carbon atoms, an alkoxycarbonyl group (the alkoxy moiety has 1 to 8 carbon atoms), or an aralkyl group (the aryl moiety has 6 to 10 carbon atoms, and the alkylene moiety has 1 to 8 carbon atoms), $R^5$ is hydrogen atom, an alkyl group having 1 to 8 carbon atoms, an alkenyl group having 2 to 8 carbon atoms, an alkyl group having 1 to 8 carbon atoms and substituted with 1 to 3 halogen atoms, an alkyl group having 1 to 8 carbon atoms and substituted with hydroxyl group, or an aralkyl group (the aryl moiety has 6 to 10 carbon atoms, and the alkylene moiety has 1 to 8 carbon atoms), $R^6$ and $R^7$ may be the same or different, and are hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, or amino group, X is N, Y is C(=O), the double line consisting of the solid line and the broken line is a single bond, Z is O, A is benzene ring, or pyridine ring, which may have the same or different 1 to 4 substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, and a dialkylamino group having 2 to 8 carbon atoms, as a substituent, B is an atomic bond, D is tetrazole ring, or imidazole ring, which may have the same or different 1 or 2 substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, and a dialkylamino group having 2 to 8 carbon atoms, D binds to A via nitrogen atom of D, and binds to E via carbon atom of D, E is $-(CR^9R^{10})_n-$, wherein $R^9$ and $R^{10}$ may be the same or different, and are hydrogen atom, hydroxyl group, or an alkyl group having 1 to 8 carbon atoms, and n is an integer of 1 to 8, G is benzene ring, which may have the same or different 1 to 5 substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, carbamoyl group, and methanesulfonyl group, as a substituent, and m is 1.

(15)

The compound represented by the aforementioned general formula (I), a tautomer or a stereoisomer of the compound, or a pharmacologically acceptable salt thereof, or a solvate of any of the foregoing, wherein:

$R^1$ and $R^2$ bind together to form naphthalene ring, or indane ring together with the benzene ring to which they bind, $R^3$ and $R^4$ are hydrogen atoms, $R^5$ is hydrogen atom, $R^6$ and $R^7$ are hydrogen atoms, X is N, Y is C(=O), the double line consisting of the solid line and the broken line is a single bond, Z is O, A is benzene ring, which may have the same or different 1 to 4 substituents selected from an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, and a dialkylamino group having 2 to 8 carbon atoms, as a substituent, B is an atomic bond, D is tetrazole ring, or imidazole ring, which may have, as a substituent, 1 or 2 substituents selected from an alkyl groups having 1 to 8 carbon atom, and an alkyl group having 1 to 8 carbon atoms and substituted with 1 to 3 halogen atoms, D binds to A via nitrogen atom of D, and binds to E via carbon atom of D, E is $-(CR^9R^{10})_n-$, wherein $R^9$ and $R^{10}$ are the same or different, and are hydrogen atom, or an alkyl group having 1 to 8 carbon atoms, and n is an integer of 1 to 4, G is benzene ring, which may have the same or different 1 to 5 substituents selected from an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, and carbamoyl group, as a substituent, and m is 1.

(16)

The compound represented by the aforementioned general formula (I), a tautomer or a stereoisomer of the compound, or a pharmacologically acceptable salt thereof, or a solvate of any of the foregoing, wherein:

$R^1$ and $R^2$ bind together to form naphthalene ring, or indane ring together with the benzene ring to which they bind, $R^3$ and $R^4$ are hydrogen atoms, $R^5$ is hydrogen atom, $R^6$ and $R^7$ are hydrogen atoms, X is N, Y is C(=O), the double line consisting of the solid line and the broken line is a single bond, Z is O, A is benzene ring, which may have the same or different 1 to 4 substituents selected from an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, and a dialkylamino group having 2 to 8 carbon atoms, as a substituent, B is an atomic bond, D is imidazole ring, which may have, as a substituent, 1 or 2 substituents selected from an alkyl groups having 1 to 8 carbon atom, and an alkyl group having 1 to 8 carbon atoms and substituted with 1 to 3 halogen atoms, D binds to A at the 2-position of the imidazole ring, and binds to E via nitrogen atom of the imidazole ring, E is $-(CR^9R^{10})_n-$, wherein $R^9$ and $R^{10}$ are the same or different, and are hydrogen atom, or an alkyl group having 1 to 8 carbon atoms, and n is an integer of 1 to 4, G is benzene ring, which may have the same or different 1 to 5 substituents selected from an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, and carbamoyl group, as a substituent, and m is 1.

As the compounds of the present invention represented by the aforementioned general formula (II), the compounds shown below are preferred.

(17)

The compound represented by the aforementioned general formula (II), a tautomer or a stereoisomer of the compound, or a pharmacologically acceptable salt thereof, or a solvate of any of the foregoing, wherein $R^{1a}$, $R^{2a}$, $R^{3a}$, $R^{4a}$, $R^{5a}$, and $R^{6a}$ may be the same or different, and are hydrogen atom, an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, or hydroxyl group.

(18)

The compound represented by the aforementioned general formula (II) or the compound according to (17) mentioned above, a tautomer or a stereoisomer of the compound, or a pharmacologically acceptable salt thereof, or a solvate of any of the foregoing, wherein $X^a$ is N, and $Y^a$ is C(=O).

(19)

The compound represented by the aforementioned general formula (II) or the compound according to (17) or (18) mentioned above, a tautomer or a stereoisomer of the compound, or a pharmacologically acceptable salt thereof, or a solvate of any of the foregoing, wherein $A^a$ is benzene ring, or pyridine ring, which may have the same or different 1 to 4 substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, and a dialkylamino group having 2 to 8 carbon atoms, as a substituent.

(20)

The compound represented by the aforementioned general formula (II) or the compound according to (17) or (18) mentioned above, a tautomer or a stereoisomer of the compound, or a pharmacologically acceptable salt thereof, or a solvate of any of the foregoing, wherein $A^a$ is benzene ring, which may have the same or different 1 to 4 substituents selected from an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, and amino group, as a substituent.

(21)

The compound represented by the aforementioned general formula (II) or the compound according to any one of (17) to (20) mentioned above, a tautomer or a stereoisomer of the compound, or a pharmacologically acceptable salt thereof, or a solvate of any of the foregoing, wherein $D^a$ is tetrazole ring, imidazole ring, imidazoline ring, triazole ring, pyrrole ring, pyrrolidine ring, piperazine ring, or piperidine ring, which may have the same or different 1 to 4 substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, and a dialkylamino group having 2 to 8 carbon atoms, as a substituent.

(22)

The compound represented by the aforementioned general formula (II) or the compound according to any one of (17) to (20) mentioned above, a tautomer or a stereoisomer of the compound, or a pharmacologically acceptable salt thereof, or a solvate of any of the foregoing, wherein $D^a$ is tetrazole ring.

(23)

The compound according to (21) or (22) mentioned above, a tautomer or a stereoisomer of the compound, or a pharmacologically acceptable salt thereof, or a solvate of any of the foregoing, wherein $D^a$ binds to $A^a$ via nitrogen atom.

(24)

The compound represented by the aforementioned general formula (II) or the compound according to any one of (17) to (23) mentioned above, a tautomer or a stereoisomer of the compound, or a pharmacologically acceptable salt thereof, or a solvate of any of the foregoing, wherein $E^a$ is an alkylene chain having 1 to 5 carbon atoms.

(25)

The compound represented by the aforementioned general formula (II) or the compound according to any one of (17) to (24) mentioned above, a tautomer or a stereoisomer of the compound, or a pharmacologically acceptable salt thereof, or a solvate of any of the foregoing, wherein $G^a$ is benzene ring, pyridine ring, imidazole ring, pyrrole ring, pyrazole ring, pyrimidine ring, pyridazine ring, pyrazine ring, or a 5- to 7-membered cycloalkyl ring, which may have the same or different 1 to 5 substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, hydroxyl group, nitro group, cyano group, amino group, an alkylamino group having 1 to 8 carbon atoms, a dialkylamino group having 2 to 8 carbon atoms, carbamoyl group, and methanesulfonyl group, as a substituent.

It is preferred that, in the aforementioned general formula (I), when A is benzene ring which may be substituted, and B is an atomic bond, X and D are mutually at para-positions on the benzene ring.

It is also preferred that, in the aforementioned general formula (I), when A is pyridine ring which may be substituted, and B is an atomic bond, the pyridine ring binds to X at the 3-position thereof, and binds to D at the 6-position thereof.

It is also preferred that, in the aforementioned general formula (II), when $A^a$ is benzene ring which may be substituted, and B is an atomic bond, $X^a$ and $D^a$ are mutually at para-positions on the benzene ring.

It is also preferred that, in the aforementioned general formula (II), when A is pyridine ring which may be substituted, the pyridine ring binds to $X^a$ at the 3-position thereof, and binds to $D^a$ at the 6-position thereof.

Examples of the pharmacologically acceptable salts of the compounds represented by the aforementioned general formula (I) or (II) include hydrochlorides, and alkali metal salts such as those of sodium, potassium, and lithium.

Further, there may be stereoisomers of the compounds of the present invention, such as cis- and trans-isomers, optically active substances, and racemates, and all of these substances fall within the scope of the present invention.

The synthetic schemes of the compounds of the present invention represented by the aforementioned general formula (I) or (II) are shown below.

(I) Synthesis Methods of
1,2-naphtho[1,2-b][1,4]diazepin-2,4-dione
Derivatives (1) Compounds represented by the aforementioned general formula (II) in which $X^a$ is N, $Y^a$ is C(=O), the double line consisting of the solid line and the broken line is a single bond, and $D^a$ is tetrazolyl group Synthesis method A

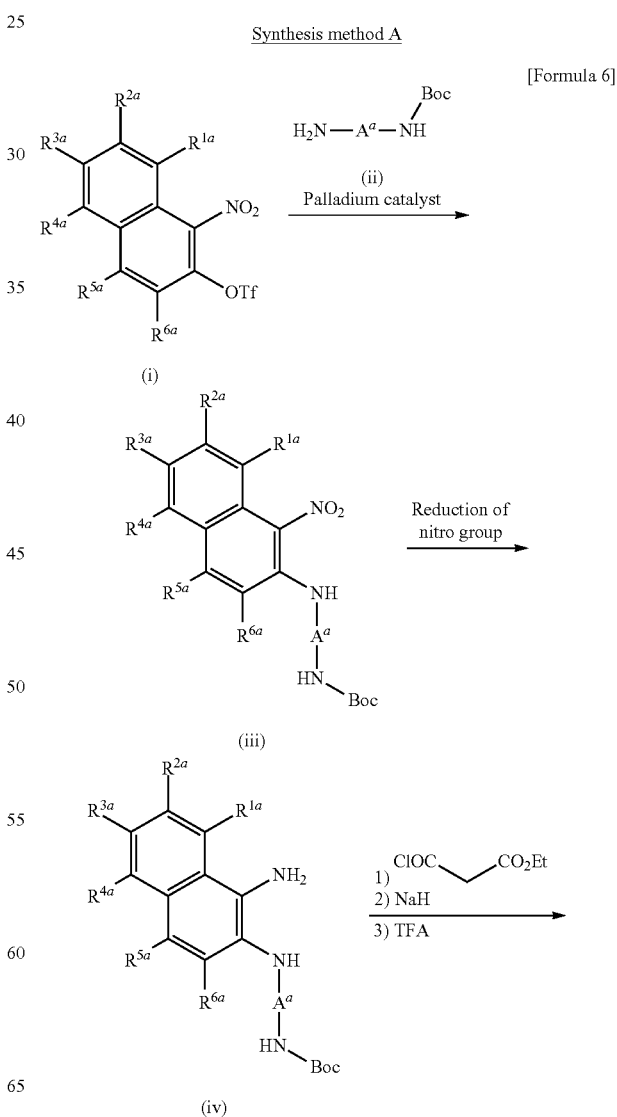

[Formula 6]

-continued

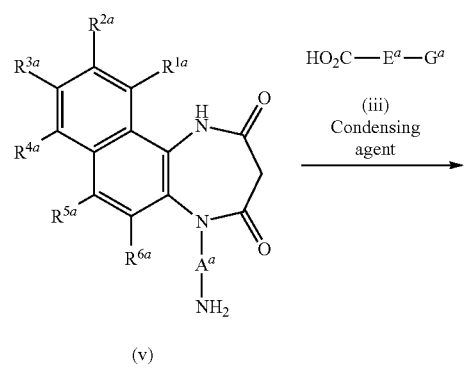

(v)

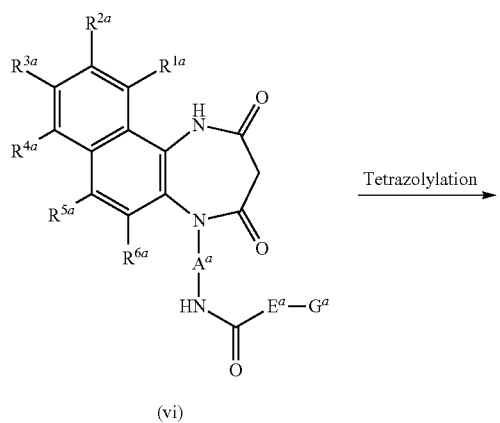

(vi)

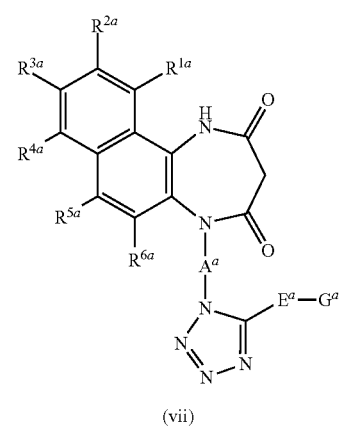

(vii)

(2) Compounds represented by the aforementioned general formula (II) in which $X^a$ is N, $Y^a$ is C(=O), the double line consisting of the solid line and the broken line is a single bond, and $D^a$ is tetrazolyl group Synthesis method B-1

[Formula 7]

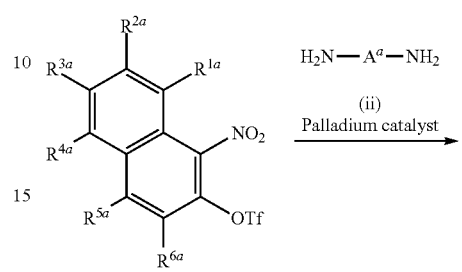

(i)

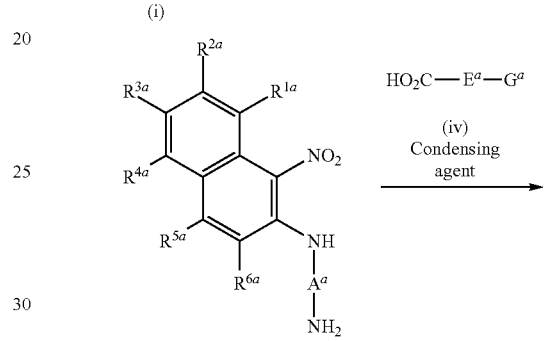

(iii)

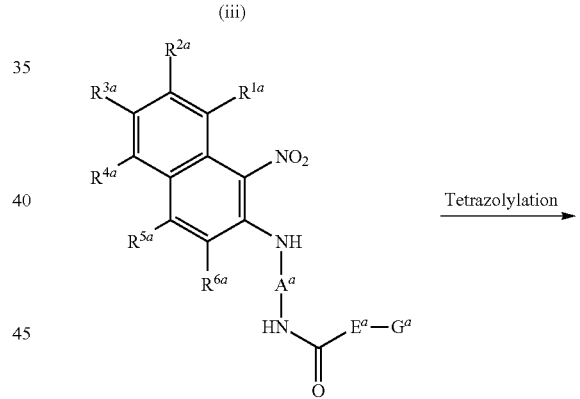

(v)

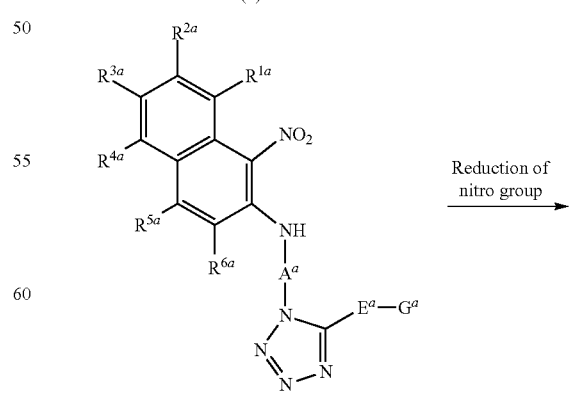

(vi)

(In the formulas, Boc represents t-butoxycarbonyl group, Et represents ethyl group, and $R^{1a}$ to $R^{6a}$, $A^a$, $E^a$, and $G^a$ have the same meanings as those defined above.)

-continued

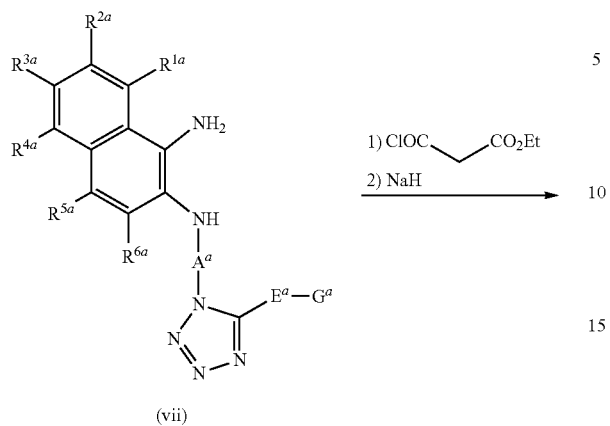

(vii)

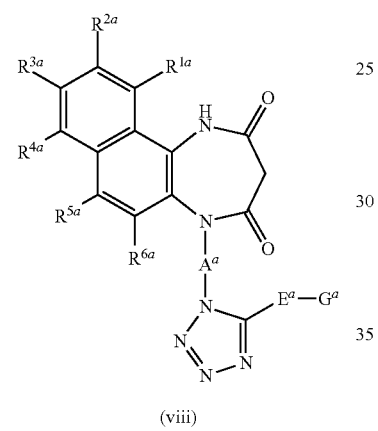

(viii)

(In the formulas, Et represents ethyl group, and $R^{1a}$ to $R^{6a}$, $A^a$, $E^a$, and $G^a$ have the same meanings as those defined above.)

(3) Compounds represented by the aforementioned general formula (II) in which $X^a$ is N, $Y^a$ is C(=O), the double line consisting of the solid line and the broken line is a single bond, and $D^a$ is imidazolyl group Synthesis method B-2

[Formula 8]

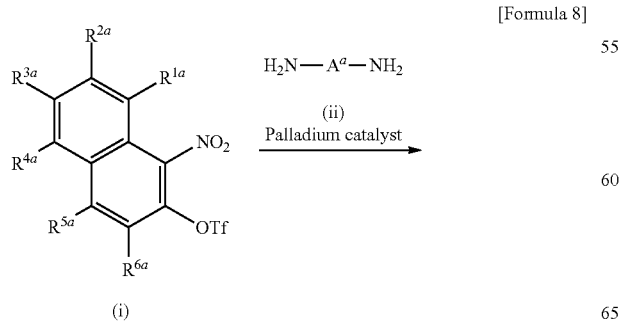

-continued

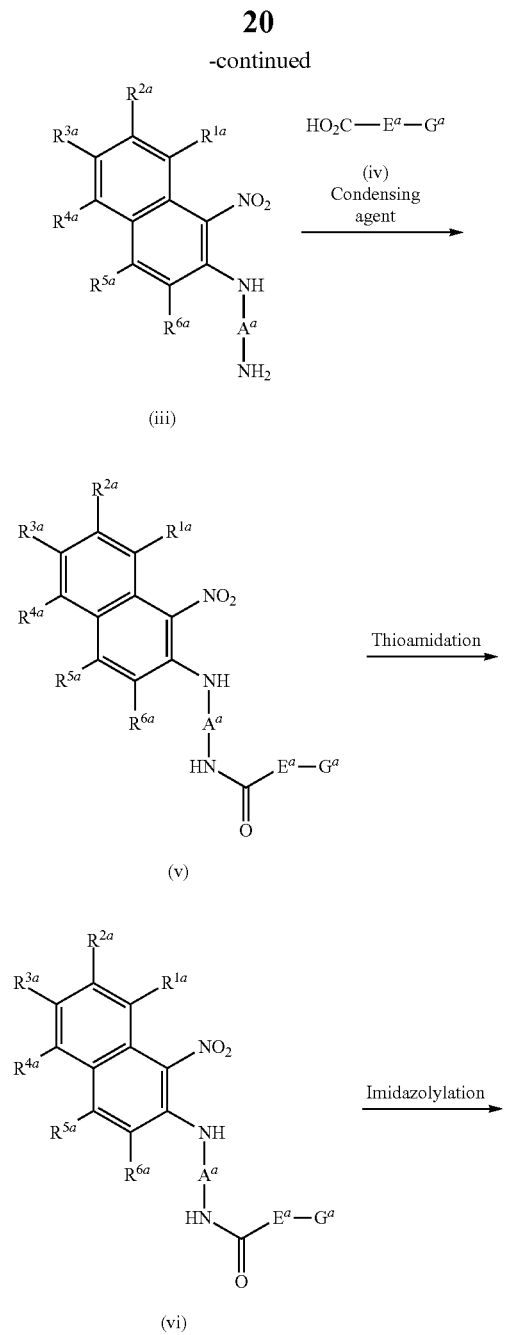

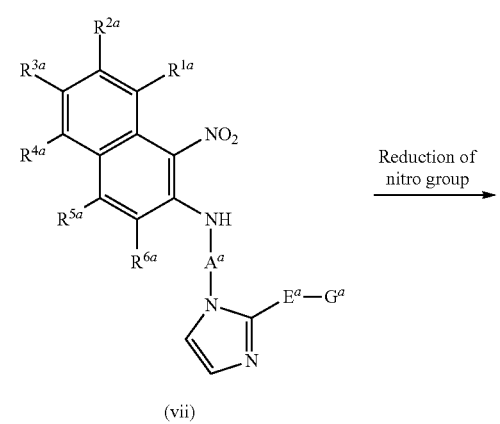

(vii)

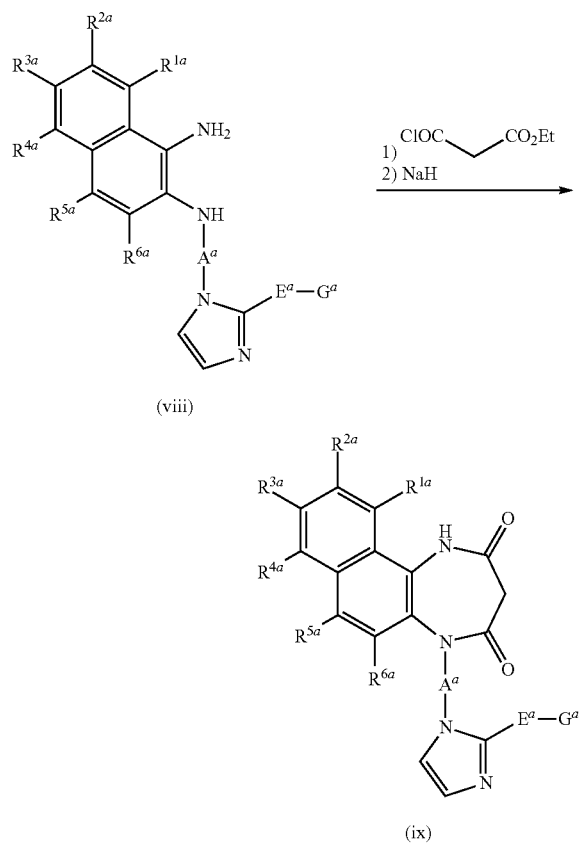

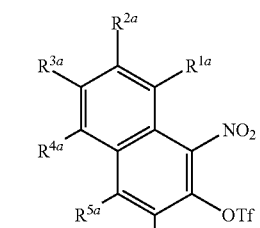

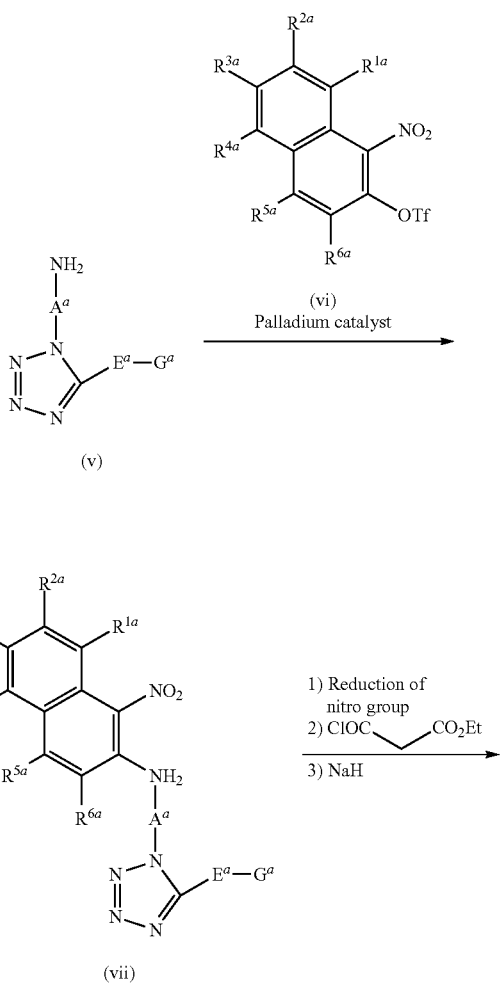

(In the formulas, Et represents ethyl group, and $R^{1a}$ to $R^{6a}$, $A^a$, $E^a$, and $G^a$ have the same meanings as those defined above.)

(4) Compounds represented by the aforementioned general formula (II) in which $X^a$ is N, $Y^a$ is C(=O), the double line consisting of the solid line and the broken line is a single bond, and $D^a$ is tetrazolyl group Synthesis method C

[Formula 9]

(In the formulas, Et represents ethyl group, and $R^{1a}$ to $R^{6a}$, $A^a$, $E^a$, and $G^a$ have the same meanings as those defined above.)

(5) Compounds represented by the aforementioned general formula (II) in which $X^a$ is N, $Y^a$ is C(=O), the double line consisting of the solid line and the broken line is a single bond, and $D^a$ is imidazolyl group Synthesis method D-1

[Formula 10]

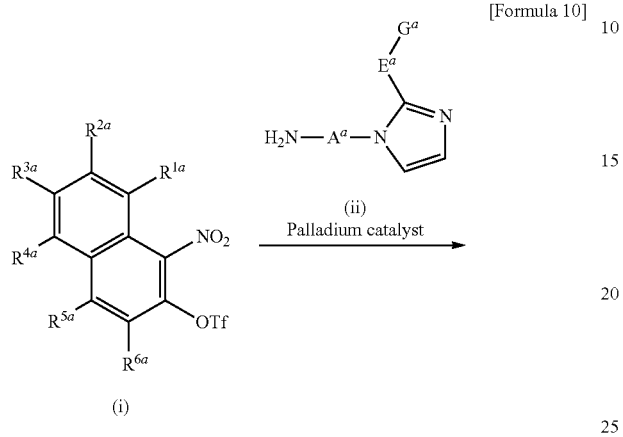

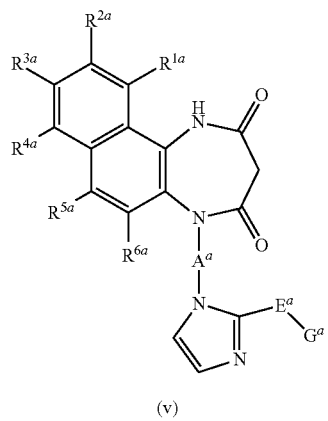

(In the formulas, Et represents ethyl group, and $R^{1a}$ to $R^{6a}$, $A^a$, $E^a$, and $G^a$ have the same meanings as those defined above.)

Synthesis method D-2

[Formula 11]

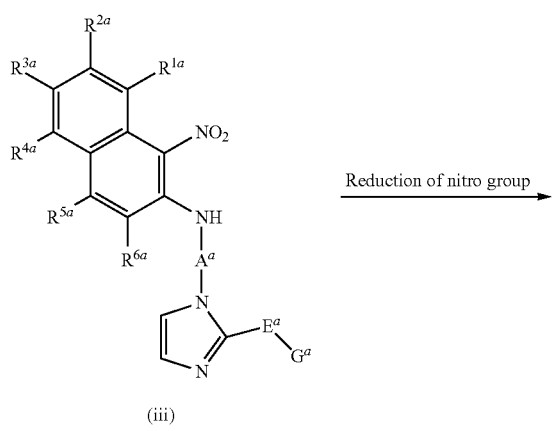

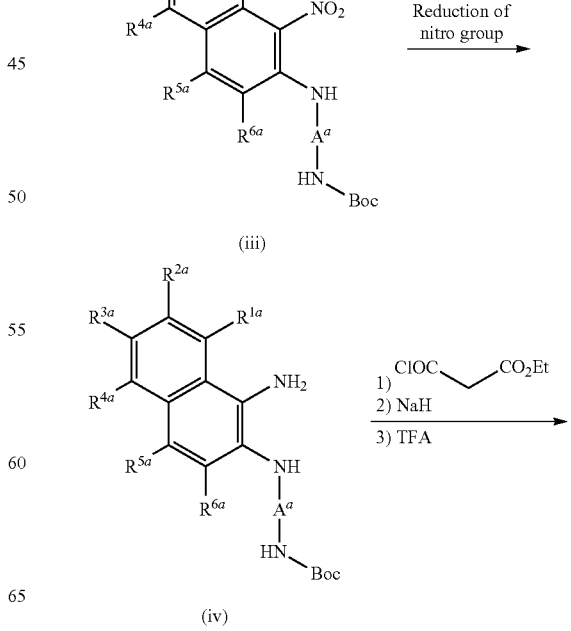

-continued

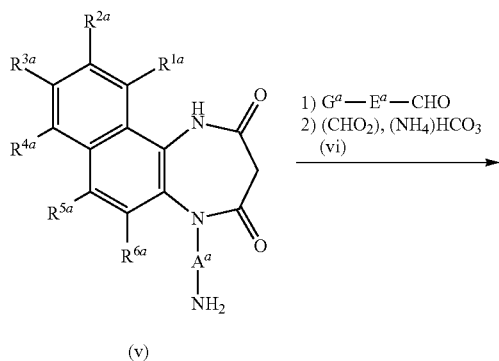

(v)

1) $G^a$—$E^a$—CHO
2) $(CHO_2)$, $(NH_4)HCO_3$
(vi)

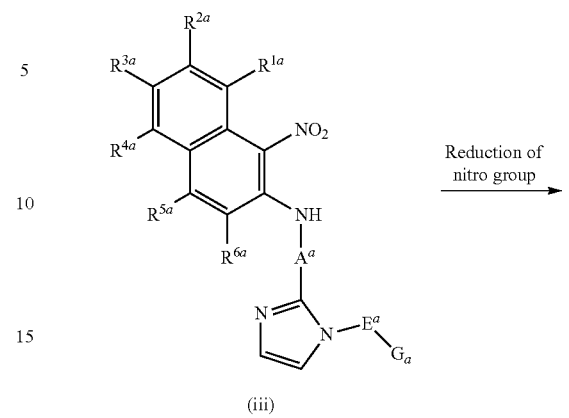

(iii)

Reduction of nitro group

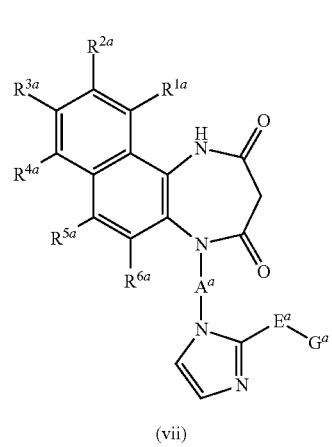

(vii)

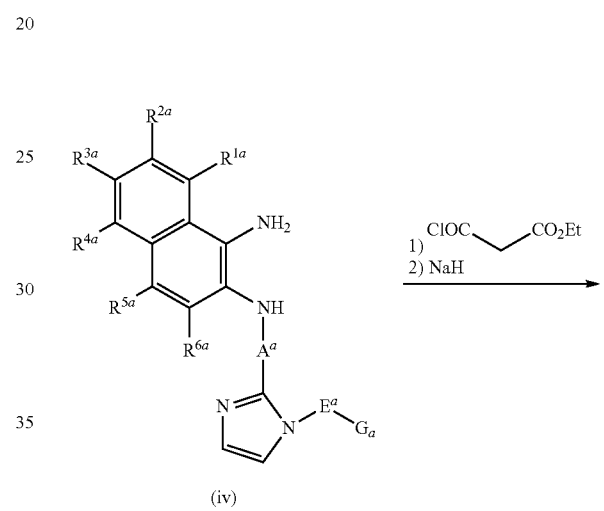

(iv)

1) ClOC—CO$_2$Et
2) NaH (In the formulas, Boc represents t-butoxycarbonyl group, Et represents ethyl group, and $R^{1a}$ to $R^{6a}$, $A^a$, $E^a$, and $G^a$ have the same meanings as those defined above.)

Synthesis method D-3

[Formula 12]

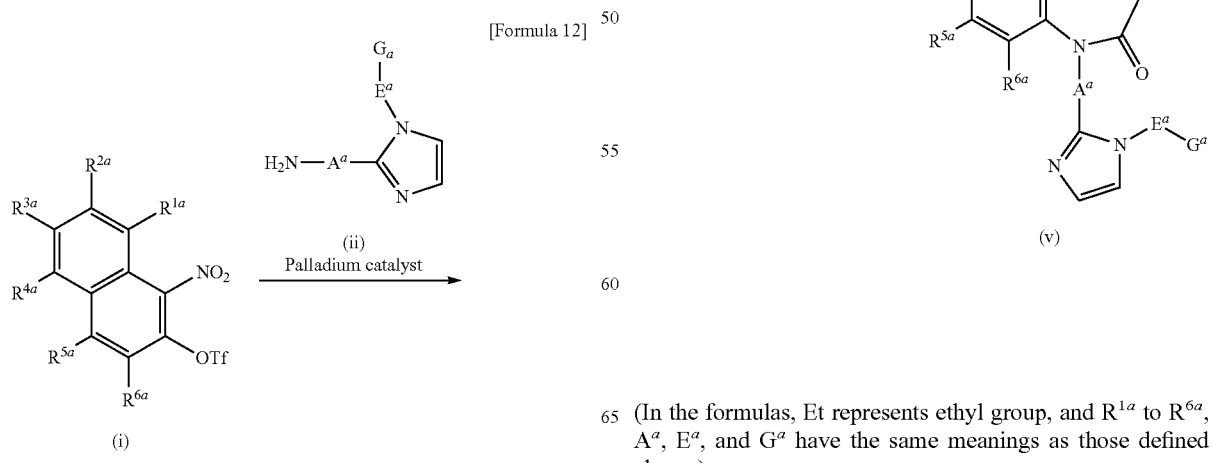

(i) (ii) Palladium catalyst (v)

(In the formulas, Et represents ethyl group, and $R^{1a}$ to $R^{6a}$, $A^a$, $E^a$, and $G^a$ have the same meanings as those defined above.)

Synthesis of method D-4

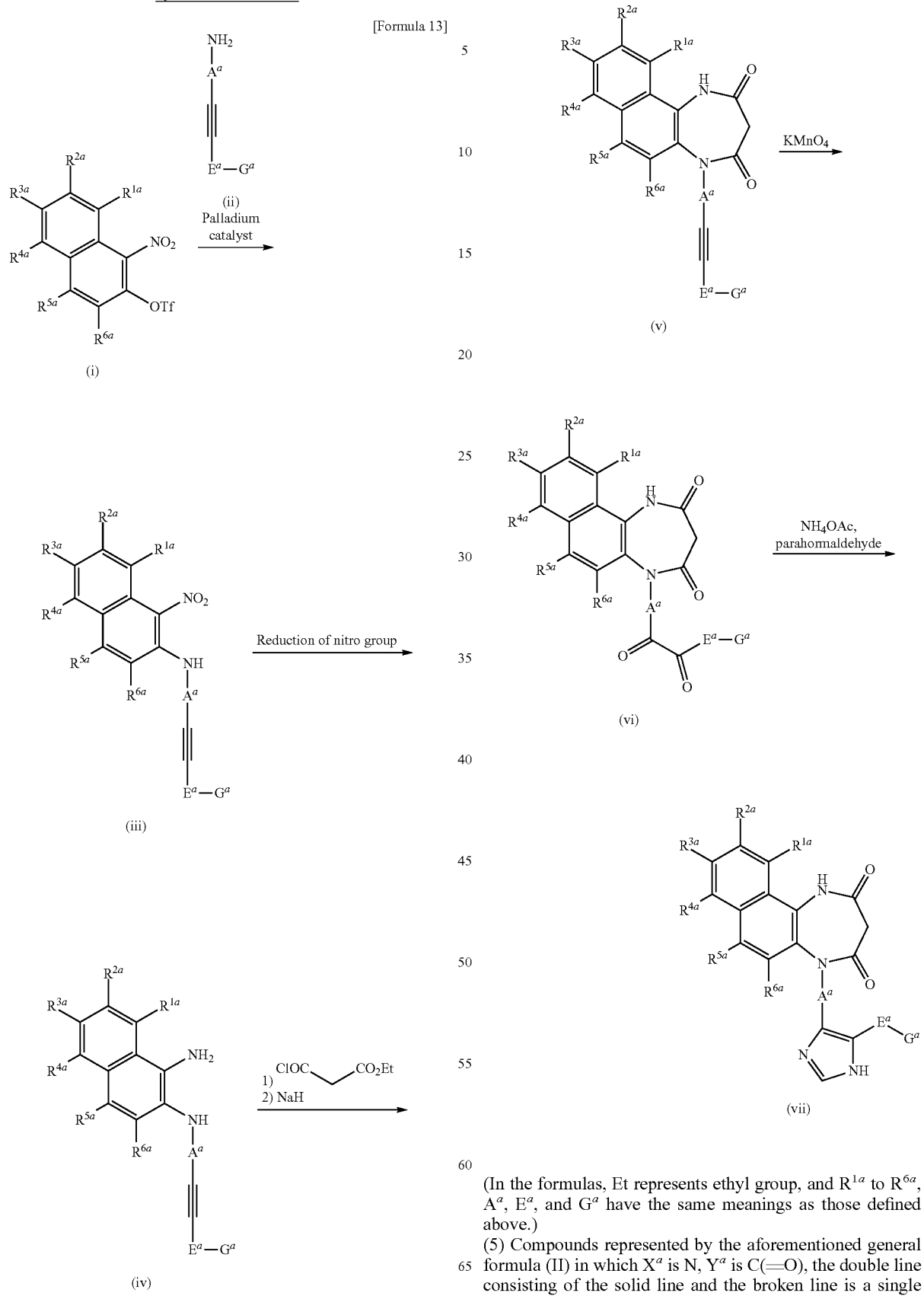

(In the formulas, Et represents ethyl group, and $R^{1a}$ to $R^{6a}$, $A^a$, $E^a$, and $G^a$ have the same meanings as those defined above.)

(5) Compounds represented by the aforementioned general formula (II) in which $X^a$ is N, $Y^a$ is C(=O), the double line consisting of the solid line and the broken line is a single bond, and $D^a$ is 4,5-dihydroimidazole group Synthesis method E

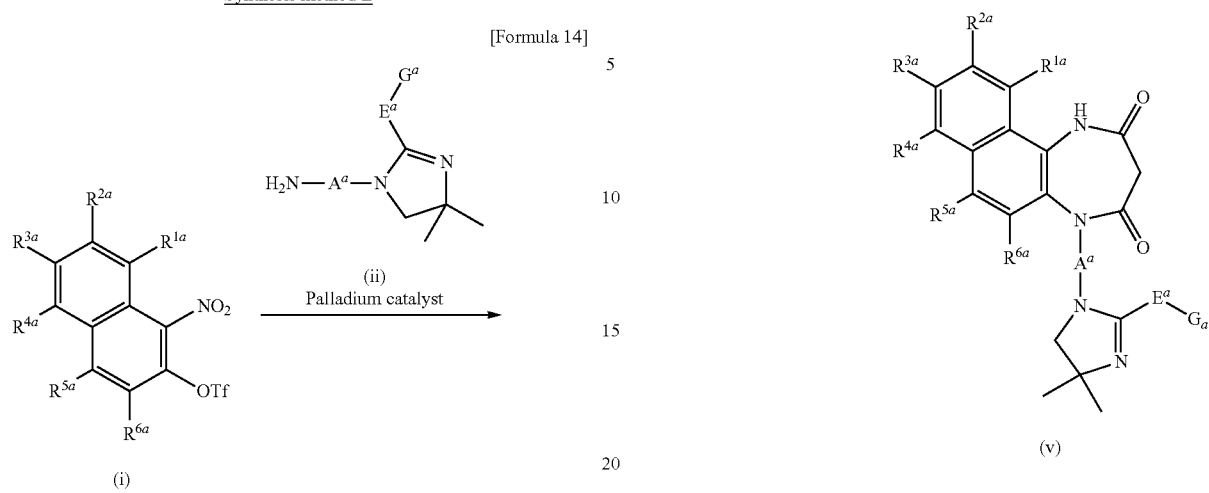

(In the formulas, Et represents ethyl group, and $R^{1a}$ to $R^{6a}$, $A^a$, $E^a$, $G^a$ have the same meanings as those defined above.)

(II) Synthesis Method of benzo[f]quinoxaline-2,3(1H,4H)-dione Derivatives (1) Compounds represented by the aforementioned general formula (I) in which X is N, Y is C(=O), the double line consisting of the solid line and the broken line is a single bond, D is tetrazolyl group, and m=0

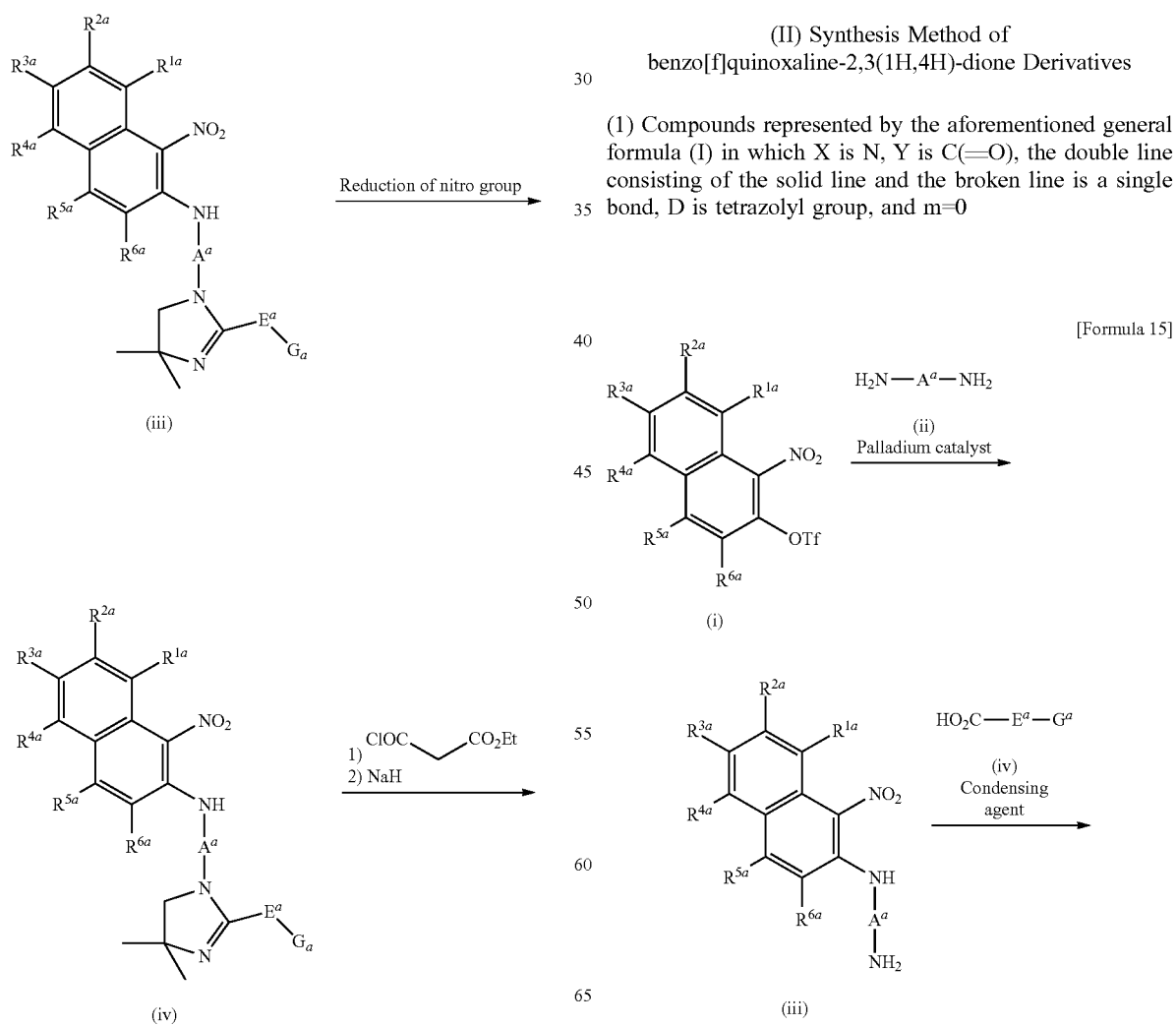

-continued

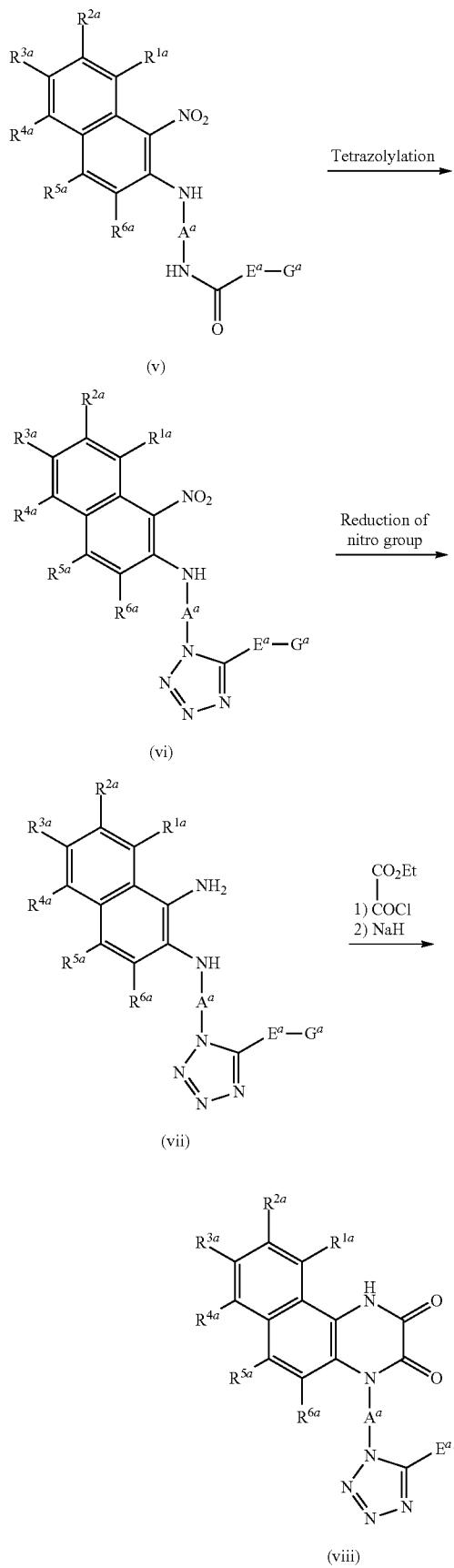

(In the formulas, Et represents ethyl group, and $R^{1a}$ to $R^{6a}$, $A^a$, $E^a$, and $G^a$ have the same meanings as those defined above for the aforementioned general formula (II).)

(III) Synthesis Method of 5,8,9,10-tetrahydroindeno [4,5-b][1,4]diazepine-2,4(1H,3H)-dione Derivatives (1) Compounds represented by the aforementioned general formula (I) in which X is N, Y is C(=O), the double line consisting of the solid line and the broken line is a single bond, D is tetrazolyl group, and m=1

[Formula 16]

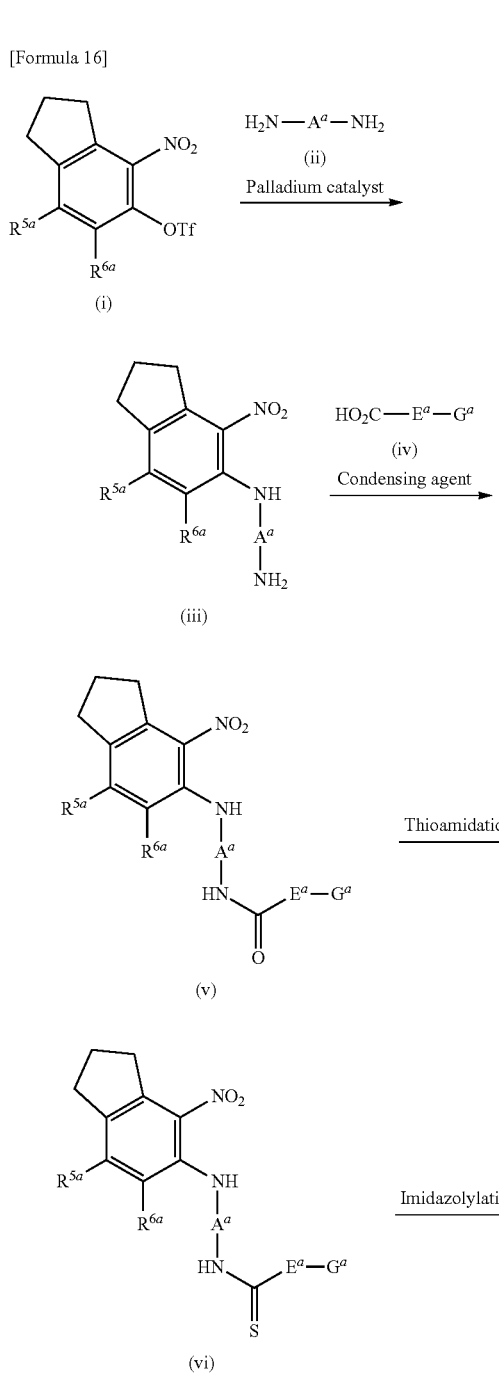

-continued

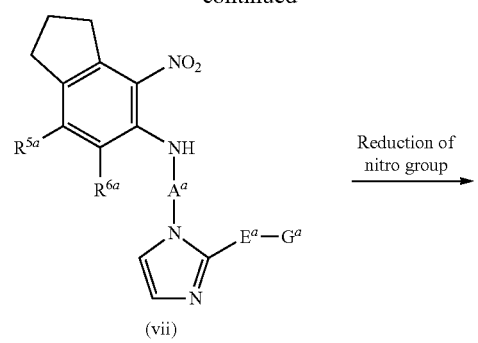

(vii)

Reduction of nitro group →

Synthesis method A

[Formula 17]

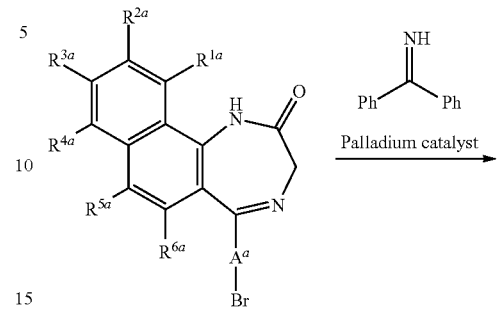

(i)

Palladium catalyst →

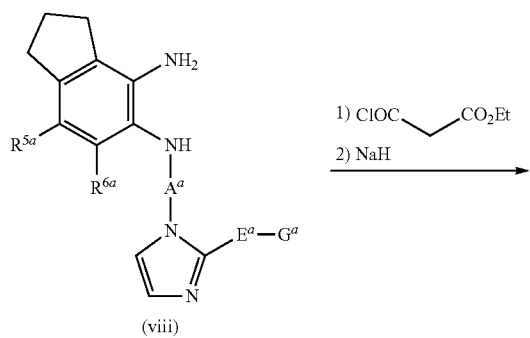

(viii)

1) ClOC~~CO₂Et
2) NaH
→

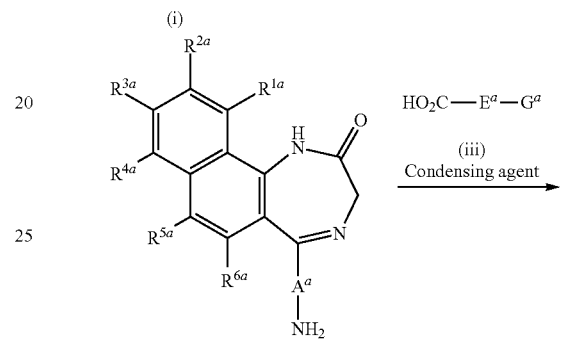

(ii)

HO₂C—Eᵃ—Gᵃ

(iii)
Condensing agent →

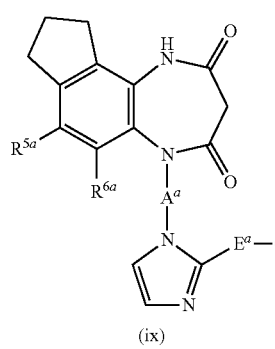

(ix)

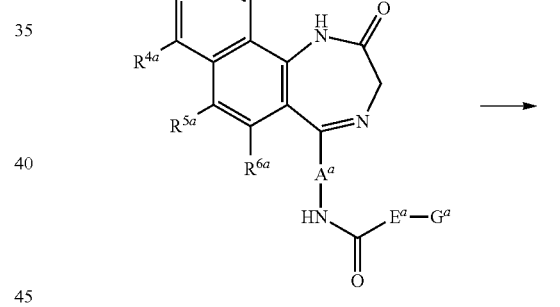

(iv)

→

(In the formulas, Et represents ethyl group, and R⁵ᵃ, R⁶ᵃ, Aᵃ, Eᵃ, and Gᵃ have the same meanings as those defined above for the aforementioned general formula (II).)

(IV) Synthesis Methods of naphtho[1,2-e][1,4]diazepin-2-one Derivatives (5) Compounds represented by the aforementioned general formula (II) in which Xᵃ is C, Yᵃ is N, the double line consisting of the solid line and the broken line is a double bond, and Dᵃ is tetrazolyl group

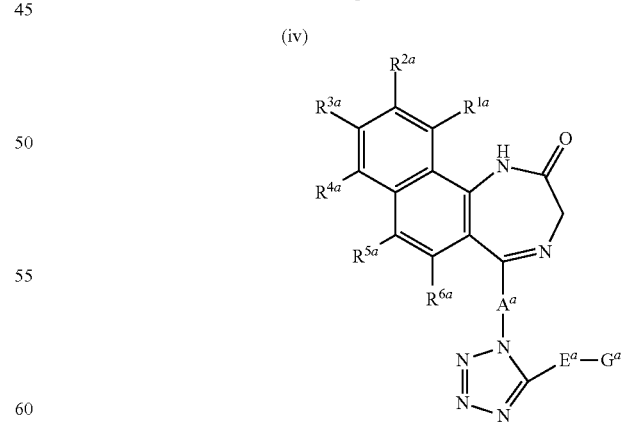

(v)

(In the formulas, Ph represents phenyl group, and R¹ᵃ to R⁶ᵃ, Aᵃ, Eᵃ, and Gᵃ have the same meanings as those defined above.)

(6) Compounds represented by the aforementioned general formula (II) in which $X^a$ is C, $Y^a$ is N, the double line consisting of the solid line and the broken line is a double bond, and $D^a$ is tetrazolyl group

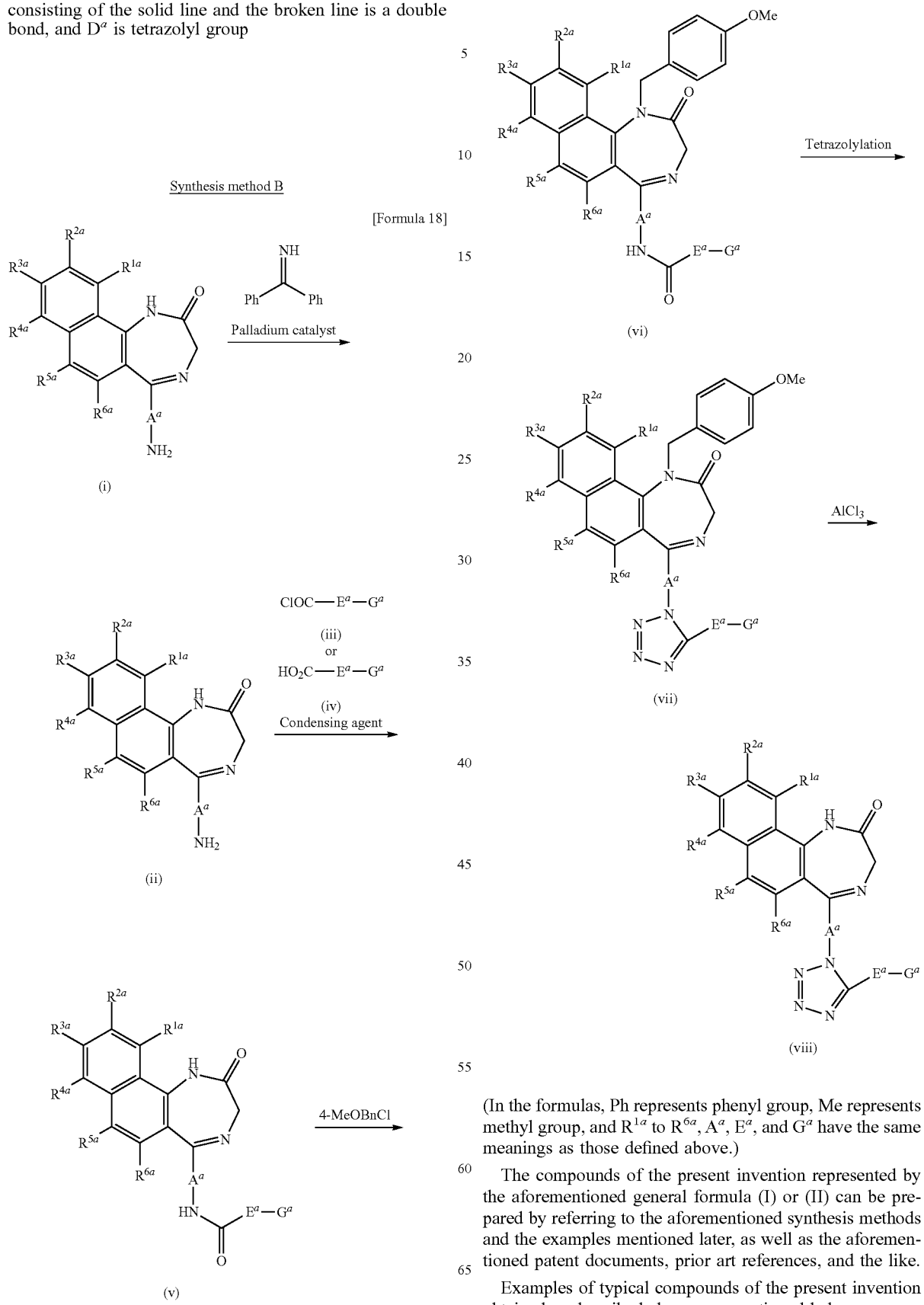

(In the formulas, Ph represents phenyl group, Me represents methyl group, and $R^{1a}$ to $R^{6a}$, $A^a$, $E^a$, and $G^a$ have the same meanings as those defined above.)

The compounds of the present invention represented by the aforementioned general formula (I) or (II) can be prepared by referring to the aforementioned synthesis methods and the examples mentioned later, as well as the aforementioned patent documents, prior art references, and the like.

Examples of typical compounds of the present invention obtained as described above are mentioned below.

Examples of Typical Compounds 1

[Formula 19]

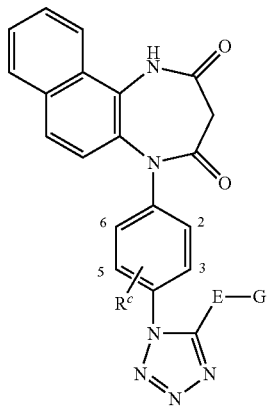

(In the formula, $R^C$, E, and G are as mentioned in Tables 1 to 3.)

TABLE 1

| $R^c$ | E | G |
|---|---|---|
| H | $CH_2$ | (2-OMe)Phenyl |
| H | $CH_2$ | (2-OH)Phenyl |
| H | $CH_2-CH_2$ | Pyridin-3-yl |
| H | $CH_2-CH_2$ | Phenyl |
| H | $CH_2$ | Pyridin-4-yl |
| H | $CH_2$ | Phenyl |
| H | $CH_2$ | Pyridin-3-yl |
| H | $CH_2-CH_2$ | Cyclohexyl |
| H | $CH_2-CH_2$ | Pyridin-4-yl |
| H | $CH_2$ | Pyridin-2-yl |
| H | $CH_2-CH_2$ | Pyridin-2-yl |
| H | $CH_2$ | Imidazol-1-yl |

TABLE 2

| $R^c$ | E | G |
|---|---|---|
| H | $CH_2-CH_2$ | Imidazol-1-yl |
| H | $CH_2-CH_2$ | (2-OMe)Phenyl |
| H | $CH_2-CH_2-CH_2$ | Phenyl |
| H | $NH-CH_2$ | Pyridin-2-yl |
| H | $CH_2-NH$ | Phenyl |
| H | $CH_2-O$ | Phenyl |
| H | $CH_2$ | (6-F)Pyridin-2-yl |
| H | $CH_2-CH_2$ | (6-F)Pyridin-2-yl |
| H | $C(Me)_2$ | (2-OMe)Phenyl |
| H | $C(Me)-CH_2$ | Pyridin-2-yl |
| H | $CH_2-C(Me)_2$ | Pyridin-2-yl |
| H | $CH_2-CH_2$ | Pyrimidin-2-yl |

TABLE 3

| $R^c$ | E | G |
|---|---|---|
| H | $CH_2-CH_2$ | Pyrazin-2-yl |
| H | $CH_2-CH_2$ | Pyridazin-3-yl |
| H | $CH_2-C(Me)_2$ | Pyridin-3-yl |
| 3-F | $CH(Me)$ | (2-OMe)Phenyl |
| 3-Me | $CH_2-CH_2$ | Pyridin-3-yl |
| 3-OMe | $CH_2-CH_2$ | Phenyl |
| 3,5-F | $CH_2$ | Pyridin-4-yl |
| 3-$NH_2$ | $CH_2$ | Phenyl |

TABLE 3-continued

| $R^c$ | E | G |
|---|---|---|
| 3,6-F | $CH_2$ | Pyridin-3-yl |
| 3-OMe | $CH_2-CH_2$ | Pyridin-2-yl |
| 3-CN | $CH_2-CH_2$ | Pyridin-2-yl |
| 3-$CF_3$ | $CH_2-CH_2$ | Pyridin-2-yl |

Examples of Typical Compounds 2

[Formula 20]

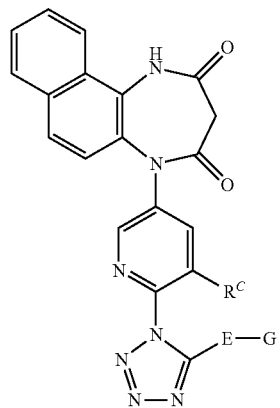

(In the formula, $R^C$, E, and G are as mentioned in Tables 4 to 6.)

TABLE 4

| $R^c$ | E | G |
|---|---|---|
| H | $CH_2$ | (2-OMe)Phenyl |
| H | $CH_2$ | (2-OH)Phenyl |
| H | $CH_2-CH_2$ | Pyridin-3-yl |
| H | $CH_2-CH_2$ | Phenyl |
| H | $CH_2$ | Pyridin-4-yl |
| H | $CH_2$ | Phenyl |
| H | $CH_2$ | Pyridin-3-yl |
| H | $CH_2-CH_2$ | Cyclohexyl |
| H | $CH_2-CH_2$ | Pyridin-4-yl |
| H | $CH_2$ | Pyridin-2-yl |
| H | $CH_2$ | Pyridin-2-yl |

TABLE 5

| $R^c$ | E | G |
|---|---|---|
| H | $CH_2$ | Imidazol-1-yl |
| H | $CH_2-CH_2$ | Imidazol-1-yl |
| H | $CH_2-CH_2$ | (2-OMe)Phenyl |
| H | $CH_2$ | (2-OMe)Phenyl |
| H | $CH_2-CH_2-CH_2$ | Phenyl |
| H | $CH_2$ | (6-F)Pyridin-2-yl |
| H | $CH_2-CH_2$ | (6-F)Pyridin-2-yl |
| H | $C(Me)_2$ | (2-OMe)Phenyl |
| H | $C(Me)-CH_2$ | Pyridin-2-yl |
| H | $CH_2-C(Me)_2$ | Pyridin-2-yl |
| H | $CH_2-CH_2$ | Pyrimidin-2-yl |

TABLE 6

| R^c | E | G |
|---|---|---|
| H | CH$_2$—CH$_2$ | Pyrazin-2-yl |
| H | CH$_2$—CH$_2$ | Pyridazin-3-yl |
| H | CH$_2$—C(Me)$_2$ | Pyridin-3-yl |
| F | CH(Me) | (2-OMe)Phenyl |
| Me | CH$_2$—CH$_2$ | Pyridin-3-yl |
| OMe | CH$_2$—CH$_2$ | Phenyl |
| F | CH$_2$ | Pyridin-4-yl |
| Me | CH$_2$ | Phenyl |
| OMe | CH$_2$ | Pyridin-3-yl |
| F | CH$_2$—CH$_2$ | Pyridin-2-yl |
| CN | CH$_2$—CH$_2$ | Pyridin-2-yl |
| F | CH$_2$—CH$_2$ | Pyridin-2-yl |

Examples of Typical Compounds 3

[Formula 21]

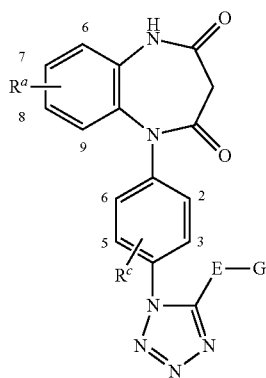

(In the formula, R$^a$, R$^C$, E, and G are as mentioned in Tables 7 to 9.)

TABLE 7

| R$^a$ | R$^c$ | E | G |
|---|---|---|---|
| 7-OMe | H | CH$_2$ | (2-OMe)Phenyl |
| 6-OMe | H | CH$_2$ | (2-OH)Phenyl |
| 6,7-OMe | H | CH$_2$—CH$_2$ | Pyridin-3-yl |
| 7-Me | H | CH$_2$—CH$_2$ | Phenyl |
| 7-Et | H | CH$_2$ | Pyridin-4-yl |
| 7-Pr | H | CH$_2$ | Phenyl |
| 7-iPr | H | CH$_2$ | Pyridin-3-yl |
| 7-tBu | H | CH$_2$—CH$_2$ | Cyclohexyl |
| 7-CN | H | CH$_2$—CH$_2$ | Pyridin-4-yl |
| 7-CF$_3$ | H | CH$_2$ | Pyridin-2-yl |
| 7-OCF$_3$ | H | CH$_2$—CH$_2$ | Pyridin-2-yl |

TABLE 8

| R$^a$ | R$^c$ | E | G |
|---|---|---|---|
| 7,8-OMe | H | CH$_2$ | Imidazol-1-yl |
| 6,7-Me | H | CH$_2$—CH$_2$ | Imidazol-1-yl |
| 6,7-Cl | H | CH$_2$—CH$_2$ | (2-OMe)Phenyl |
| 7,8-Me | H | CH$_2$ | (2-OMe)Phenyl |
| 7,8-Et | H | CH$_2$—CH$_2$—CH$_2$ | Phenyl |
| 7-Cl | H | CH$_2$ | (6-F)Pyridin-2-yl |
| 6-OMe | H | CH$_2$—CH$_2$ | (6-F)Pyridin-2-yl |
| 6,7-OMe | H | C(Me)$_2$ | (2-OMe)Phenyl |
| 7-Me | H | C(Me)—CH$_2$ | Pyridin-2-yl |
| 7-Et | H | CH$_2$—C(Me)$_2$ | Pyridin-2-yl |
| 7-Pr | H | CH$_2$—C(Me)$_2$ | Pyridin-3-yl |

TABLE 9

| R$^a$ | R$^c$ | E | G |
|---|---|---|---|
| 7-iPr | 3-F | CH(Me) | (2-OMe)Phenyl |
| 7-tBu | 3-Me | CH$_2$—CH$_2$ | Pyridin-3-yl |
| 7-CN | 3-OMe | CH$_2$—CH$_2$ | Phenyl |
| 7-CF$_3$ | 3,5-F | CH$_2$ | Pyridin-4-yl |
| 7-OCF$_3$ | 3-NH$_2$ | CH$_2$ | Phenyl |
| 7,8-OMe | 3,6-F | CH$_2$ | Pyridin-3-yl |
| 6,7-Me | 3-OMe | CH$_2$—CH$_2$ | Pyridin-2-yl |
| 6,7-Et | 3-CN | CH$_2$—CH$_2$ | Pyridin-2-yl |
| 7,8-Me | 3-CF$_3$ | CH$_2$—CH$_2$ | Pyridin-2-yl |

Examples of Typical Compounds 4

[Formula 22]

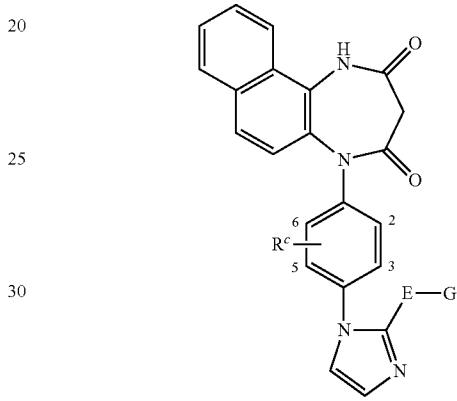

(In the formula, R$^C$, E, and G are as mentioned in Tables 10 to 12.)

TABLE 10

| R$^c$ | E | G |
|---|---|---|
| H | CH$_2$—CH$_2$ | Phenyl |
| H | CH$_2$ | (2-OMe)Phenyl |
| H | CH$_2$ | (2-OH)Phenyl |
| H | CH$_2$—CH$_2$ | Pyridin-2-yl |
| H | CH$_2$—CH$_2$ | Pyridin-3-yl |
| H | CH$_2$—CH$_2$ | (2-CF$_3$)Phenyl |
| H | CH$_2$—CH$_2$ | (2-F)Phenyl |
| H | CH$_2$—CH$_2$ | (2-OMe)Phenyl |
| H | CH$_2$ | Pyridin-4-yl |
| H | CH$_2$ | Phenyl |
| H | CH$_2$ | Pyridin-3-yl |
| H | CH$_2$ | Cyclohexyl |
| H | CH$_2$ | Pyridin-4-yl |

TABLE 11

| R$^c$ | E | G |
|---|---|---|
| H | CH$_2$ | Pyridin-2-yl |
| H | CH$_2$—CH$_2$ | Pyridin-2-yl |
| H | CH$_2$—CH$_2$ | (4-SO$_2$Me)Phenyl |
| H | CH$_2$—CH$_2$ | (4-F)Phenyl |
| H | CH$_2$—CH$_2$ | (4-CF$_3$)Phenyl |
| H | CH$_2$—CH$_2$ | (4-CONH$_2$)Phenyl |
| H | CH$_2$—CH$_2$—CH$_2$ | Phenyl |
| H | CH$_2$ | (6-F)Pyridin-2-yl |
| H | CH$_2$—CH$_2$ | (6-F)Pyridin-2-yl |
| H | C(Me)$_2$ | (2-OMe)Phenyl |

TABLE 11-continued

| $R^c$ | E | G |
|---|---|---|
| H | C(Me)—CH$_2$ | Pyridin-2-yl |
| H | CH$_2$—C(Me)$_2$ | Pyridin-2-yl |
| H | CH$_2$—CH$_2$ | Pyrimidin-2-yl |

TABLE 12

| $R^c$ | E | G |
|---|---|---|
| H | CH$_2$—CH$_2$ | Pyrazin-2-yl |
| H | CH$_2$—CH$_2$ | Pyridazin-3-yl |
| H | CH$_2$—C(Me)$_2$ | Pyridin-3-yl |
| 3-F | CH(Me) | (2-OMe)Phenyl |
| 3-Me | CH$_2$—CH$_2$ | Pyridin-3-yl |
| 3-OMe | CH$_2$—CH$_2$ | Phenyl |
| 3,5-F | CH$_2$ | Pyridin-4-yl |
| 3-NH$_2$ | CH$_2$ | Phenyl |
| 3,6-F | CH$_2$ | Pyridin-3-yl |
| 3-OMe | CH$_2$—CH$_2$ | Pyridin-2-yl |
| 3-CN | CH$_2$—CH$_2$ | Pyridin-2-yl |
| 3-CF$_3$ | CH$_2$—CH$_2$ | Pyridin-2-yl |

Examples of Typical Compounds 5

[Formula 23]

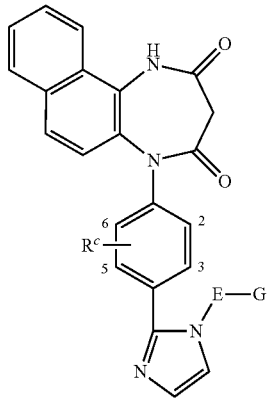

(In the formula, $R^C$, E, and G are as mentioned in Tables 13 to 15.)

TABLE 13

| $R^c$ | E | G |
|---|---|---|
| H | CH$_2$—CH$_2$ | Phenyl |
| H | CH$_2$ | (2-OMe)Phenyl |
| H | CH$_2$ | (2-OH)Phenyl |
| H | CH$_2$—CH$_2$ | Pyridin-3-yl |
| H | CH$_2$—CH$_2$ | Phenyl |
| H | CH$_2$ | Pyridin-4-yl |
| H | CH$_2$ | Phenyl |
| H | CH$_2$ | Pyridin-3-yl |
| H | CH$_2$—CH$_2$ | Cyclohexyl |
| H | CH$_2$—CH$_2$ | Pyridin-4-yl |
| H | CH$_2$ | Pyridin-2-yl |
| H | CH$_2$—CH$_2$ | Pyridin-2-yl |

TABLE 14

| $R^c$ | E | G |
|---|---|---|
| H | CH$_2$ | Imidazol-1-yl |
| H | CH$_2$—CH$_2$ | Imidazol-1-yl |
| H | CH$_2$—CH$_2$ | (2-OMe)Phenyl |
| H | CH$_2$ | (2-OMe)Phenyl |
| H | CH$_2$—CH$_2$—CH$_2$ | Phenyl |
| H | CH$_2$ | (6-F)Pyridin-2-yl |
| H | CH$_2$—CH$_2$ | (6-F)Pyridin-2-yl |
| H | C(Me)$_2$ | (2-OMe)Phenyl |
| H | C(Me)—CH$_2$ | Pyridin-2-yl |
| H | CH$_2$—C(Me)$_2$ | Pyridin-2-yl |
| H | CH$_2$—CH$_2$ | Pyrimidin-2-yl |
| H | CH$_2$—CH$_2$ | Pyrazin-2-yl |

TABLE 15

| $R^c$ | E | G |
|---|---|---|
| H | CH$_2$—CH$_2$ | Pyridazin-3-yl |
| H | CH$_2$—C(Me)$_2$ | Pyridin-3-yl |
| 3-F | CH(Me) | (2-OMe)Phenyl |
| 3-Me | CH$_2$—CH$_2$ | Pyridin-3-yl |
| 3-OMe | CH$_2$—CH$_2$ | Phenyl |
| 3,5-F | CH$_2$ | Pyridin-4-yl |
| 3-NH$_2$ | CH$_2$ | Phenyl |
| 3,6-F | CH$_2$ | Pyridin-3-yl |
| 3-OMe | CH$_2$—CH$_2$ | Pyridin-2-yl |
| 3-CN | CH$_2$—CH$_2$ | Pyridin-2-yl |
| 3-CF$_3$ | CH$_2$—CH$_2$ | Pyridin-2-yl |

Examples of Typical Compounds 6

[Formula 24]

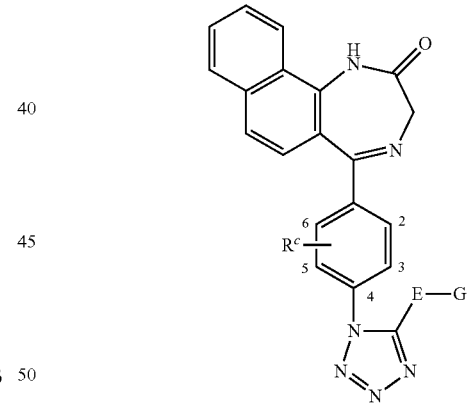

(In the formula, $R^C$, E, and G are as mentioned in Tables 16 to 18.)

TABLE 16

| $R^c$ | E | G |
|---|---|---|
| H | CH$_2$—CH$_2$ | Pyridin-2-yl |
| H | CH$_2$ | (2-OMe)Phenyl |
| H | CH$_2$ | (2-OH)Phenyl |
| H | CH$_2$—CH$_2$ | Pyridin-3-yl |
| H | CH$_2$—CH$_2$ | Phenyl |
| H | CH$_2$ | Pyridin-4-yl |
| H | CH$_2$ | Phenyl |
| H | CH$_2$ | Pyridin-3-yl |
| H | CH$_2$—CH$_2$ | Cyclohexyl |

TABLE 16-continued

| $R^c$ | E | G |
|---|---|---|
| H | CH$_2$—CH$_2$ | Pyridin-4-yl |
| H | CH$_2$ | Pyridin-2-yl |
| H | CH$_2$ | Imidazol-1-yl |

TABLE 17

| $R^c$ | E | G |
|---|---|---|
| H | CH$_2$—CH$_2$ | Imidazol-1-yl |
| H | CH$_2$—CH$_2$ | (2-OMe)Phenyl |
| H | CH$_2$ | (2-OMe)Phenyl |
| H | CH$_2$—CH$_2$—CH$_2$ | Phenyl |
| H | CH$_2$ | (6-F)Pyridin-2-yl |
| H | CH$_2$—CH$_2$ | (6-F)Pyridin-2-yl |
| H | C(Me)$_2$ | (2-OMe)Phenyl |
| H | C(Me)—CH$_2$ | Pyridin-2-yl |
| H | CH$_2$—C(Me)$_2$ | Pyridin-2-yl |
| H | CH$_2$—C(Me)$_2$ | Pyridin-3-yl |
| 3-F | CH(Me) | (2-OMe)Phenyl |
| 3-Me | CH$_2$—CH$_2$ | Pyridin-3-yl |

TABLE 18

| $R^c$ | E | G |
|---|---|---|
| 3-OMe | CH$_2$—CH$_2$ | Phenyl |
| 3,5-F | CH$_2$ | Pyridin-4-yl |
| 3-NH$_2$ | CH$_2$ | Phenyl |
| 3,6-F | CH$_2$ | Pyridin-3-yl |
| 3-OMe | CH$_2$—CH$_2$ | Pyridin-2-yl |
| 3-CN | CH$_2$—CH$_2$ | Pyridin-2-yl |
| 3-CF$_3$ | CH$_2$—CH$_2$ | Pyridin-2-yl |

Examples of Typical Compounds 7

[Formula 25]

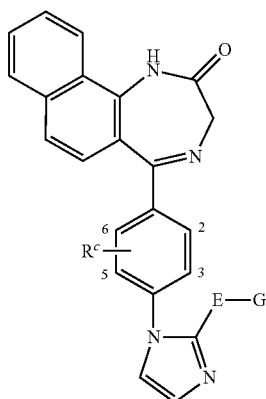

(In the formula, $R^C$, E, and G are as mentioned in Tables 19 to 21.)

TABLE 19

| $R^c$ | E | G |
|---|---|---|
| H | CH$_2$—CH$_2$ | Phenyl |
| H | CH$_2$ | (2-OMe)Phenyl |
| H | CH$_2$ | (2-OH)Phenyl |

TABLE 19-continued

| $R^c$ | E | G |
|---|---|---|
| H | CH$_2$—CH$_2$ | Pyridin-3-yl |
| H | CH$_2$—CH$_2$ | Phenyl |
| H | CH$_2$ | Pyridin-4-yl |
| H | CH$_2$ | Phenyl |
| H | CH$_2$ | Pyridin-3-yl |
| H | CH$_2$ | Cyclohexyl |
| H | CH$_2$—CH$_2$ | Pyridin-4-yl |
| H | CH$_2$ | Pyridin-2-yl |
| H | CH$_2$—CH$_2$ | Pyridin-2-yl |

TABLE 20

| $R^c$ | E | G |
|---|---|---|
| H | CH$_2$ | Imidazol-1-yl |
| H | CH$_2$—CH$_2$ | Imidazol-1-yl |
| H | CH$_2$—CH$_2$ | (2-OMe)Phenyl |
| H | CH$_2$ | (2-OMe)Phenyl |
| H | CH$_2$—CH$_2$—CH$_2$ | Phenyl |
| H | CH$_2$ | (6-F)Pyridin-2-yl |
| H | CH$_2$—CH$_2$ | (6-F)Pyridin-2-yl |
| H | C(Me)$_2$ | (2-OMe)Phenyl |
| H | C(Me)—CH$_2$ | Pyridin-2-yl |
| H | CH$_2$—C(Me)$_2$ | Pyridin-2-yl |
| H | CH$_2$—CH$_2$ | Pyrimidin-2-yl |
| H | CH$_2$—CH$_2$ | Pyrazin-2-yl |

TABLE 21

| $R^c$ | E | G |
|---|---|---|
| H | CH$_2$—CH$_2$ | Pyridazin-3-yl |
| H | CH$_2$—C(Me)$_2$ | Pyridin-3-yl |
| 3-F | CH(Me) | (2-OMe)Phenyl |
| 3-Me | CH$_2$—CH$_2$ | Pyridin-3-yl |
| 3-OMe | CH$_2$—CH$_2$ | Phenyl |
| 3,5-F | CH$_2$ | Pyridin-4-yl |
| 3-NH$_2$ | CH$_2$ | Phenyl |
| 3,6-F | CH$_2$ | Pyridin-3-yl |
| 3-OMe | CH$_2$—CH$_2$ | Pyridin-2-yl |
| 3-CN | CH$_2$—CH$_2$ | Pyridin-2-yl |
| 3-CF$_3$ | CH$_2$—CH$_2$ | Pyridin-2-yl |

Examples of Typical Compounds 8

[Formula 26]

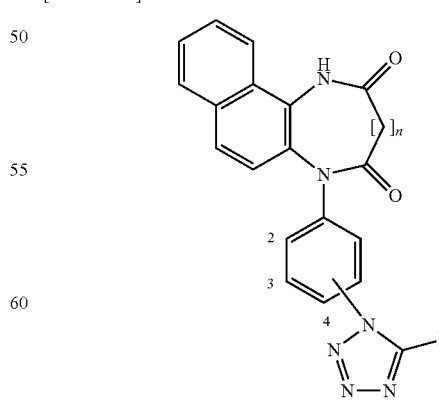

(In the formula, the substitution position of the tetrazole ring, E-G, n, and type of salt are as shown in Table 22.)

TABLE 22

| Substitution position of tetrazole ring | E-G | n | Salt |
|---|---|---|---|
| 3 | $CH_2CH_2$(2-Py) | 0 | |
| 4 | $CH_2CH_2$(6-methylpyridin-2-yl) | 1 | |
| 4 | $CH_2CH_2$(3-CN)Ph | 1 | |
| 4 | $CH_2CH_2$(3-$CONH_2$)Ph | 1 | |
| 4 | $CH_2CH_2$(2-methoxypyridin-3-yl) | 1 | |
| 4 | $CH_2$(2-$NMe_2$)Ph | 1 | MsOH |
| 4 | $CH_2C(Me)_2$(2-Py) | 1 | HCl |
| 4 | $CH_2CH_2$(3-methoxypyridin-2-yl) | 1 | HCl |
| 3 | $CH_2CH_2CH_2$(6-methylpyridin-2-yl) | 1 | |
| 3 | $CH_2CH_2CH_2$(3-CN)Ph | 1 | |
| 3 | $CH_2CH_2CH_2$(3-$CONH_2$)Ph | 1 | |
| 3 | $CH_2CH_2CH_2$(2-methoxypyridin-3-yl) | 1 | |
| 3 | $CH_2CH_2$(2-$NMe_2$)Ph | 1 | |
| 3 | $CH_2CH_2C(Me)_2$(2-Py) | 0 | |
| 3 | $CH_2CH_2CH_2$(3-methoxypyridin-2-yl) | 0 | |

Examples of Typical Compounds 9

Naphthalene Type

[Formula 27]

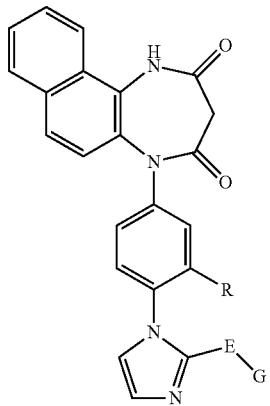

Indane Type

[Formula 28]

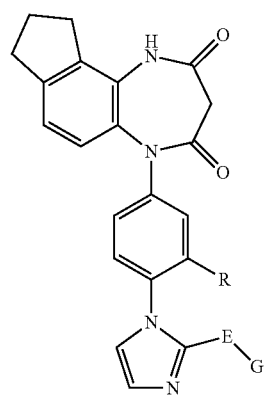

(In the formula, E-G, R, and type of salt are as mentioned in Tables 23 and 24.)

TABLE 23

| Naphthalene type or indane type | E-G | R | Salt |
|---|---|---|---|
| Naphthalene type | $CH_2CH_2$(3-F)Ph | H | HCl |
| Naphthalene type | $CH_2CH_2$(2-OMe)Ph | H | HCl |
| Naphthalene type | $CH_2CH_2$(4-F)Ph | H | HCl |
| Naphthalene type | $CH_2CH_2$(2-F)Ph | H | HCl |
| Naphthalene type | $CH_2CH_2$(4-$CF_3$)Ph | H | HCl |
| Naphthalene type | $CH_2CH_2$(2,6-Me)Ph | H | HCl |
| Naphthalene type | $CH_2CH_2$(3-$CF_3$)Ph | H | HCl |
| Naphthalene type | $CH_2CH_2$(3-OMe)Ph | H | HCl |
| Naphthalene type | $CH_2CH_2$(3-OH)Ph | H | HCl |
| Naphthalene type | $CH_2CH_2$(4-CN)Ph | H | |
| Naphthalene type | $CH_2CH_2$(4-$CONH_2$)Ph | H | |
| Naphthalene type | $CH_2CH_2$(2-CN)Ph | H | |
| Naphthalene type | $CH_2CH_2$(2-$CONH_2$)Ph | H | |
| Naphthalene type | $CH_2CH_2$(3-CN)Ph | H | |
| Naphthalene type | $CH_2CH_2$(3-$CONH_2$)Ph | H | |
| Naphthalene type | $CH_2CH_2$(3-$CONH_2$)Ph | H | HCl |
| Naphthalene type | $CH_2CH_2$(4-$SO_2$Me)Ph | H | HCl |
| Naphthalene type | $CH_2CH_2$(3-OMe,2-F)Ph | H | HCl |

TABLE 24

| Naphthalene type or indane type | E-G | R | Salt |
|---|---|---|---|
| Indane type | $CH_2CH_2$(3-OMe, 2-F)Ph | H | HCl |
| Naphthalene type | $CH_2CH_2$(3-thienyl) | H | HCl |
| Naphthalene type | $CH_2CH_2$(2-furanyl) | H | HCl |
| Indane type | $CH_2CH_2$(2-F)Ph | H | |
| Naphthalene type | $CH_2CH_2$(2-pyridyl) | H | 2HCl |
| Indane type | $CH_2CH_2$(3-F)Ph | H | HCl |
| Naphthalene type | $CH_2CH_2$(2-Ome,3-F)Ph | H | HCl |
| Naphthalene type | $CH_2CH_2$(3-F)Ph | F | |
| Naphthalene type | $CH_2CH_2$(2-OMe)Ph | OH | |
| Naphthalene type | $CH_2CH_2$(4-F)Ph | H | |
| Naphthalene type | $CH_2CH_2$(2-F)Ph | F | |
| Naphthalene type | $CH_2CH_2$(4-$CF_3$)Ph | OH | |
| Naphthalene type | $CH_2CH_2$(2,6-Me)Ph | H | |
| Naphthalene type | $CH_2CH_2$(3-$CF_3$)Ph | F | |
| Naphthalene type | $CH_2CH_2$(3-OMe)Ph | OH | |
| Naphthalene type | $CH_2CH_2$(3-OH)Ph | H | |
| Naphthalene type | $CH_2CH_2$(4-CN)Ph | F | |
| Indane type | $CH_2CH_2$(2,6-Me)Ph | H | |
| Indane type | $CH_2CH_2$(3-$CF_3$)Ph | F | |
| Indane type | $CH_2CH_2$(3-OMe)Ph | OH | |
| Indane type | $CH_2CH_2$(3-OH)Ph | H | |
| Indane type | $CH_2CH_2$(4-CN)Ph | F | |

Examples of Typical Compounds 10

[Formula 29]

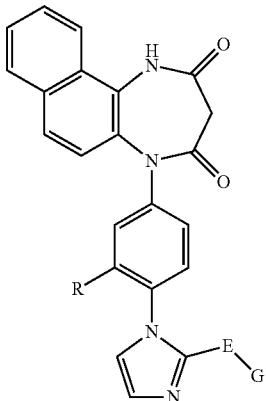

(In the formula, E-G, R, and type of salt are as mentioned in Table 25.)

TABLE 25

| E-G | R |
|---|---|
| bond—Ph | H |
| bond—(2-OMe)Ph | H |
| CH₂OPh | H |
| NH—(2-OMe)Ph | H |
| NH—Ph | H |
| CH₂SPh | F |
| CH₂NHPh | OH |
| bond—(2-F)Ph | F |
| bond—(2CF₃)Ph | OH |
| bond—(2Cl)Ph | F |
| bond—(2-Me)Ph | OH |
| bond—(2,6-Me)Ph | F |
| bond—(2,6-F)Ph | OH |
| bond—(2-OH)Ph | F |
| CH₂O(2-F)Ph | OH |
| NH—(2,6-Me)Ph | F |
| NH—(2CF₃)Ph | OH |
| bond—(3-F)Ph | F |

Examples of Typical Compounds 11

[Formula 30]

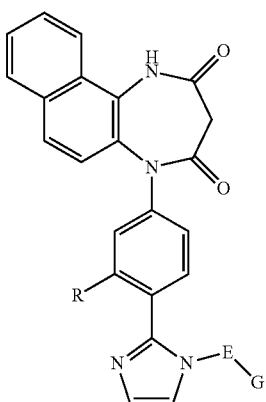

(In the formula, E-G, R, and type of salt are as mentioned in Table 26.)

TABLE 26

| E-G | R | Salt |
|---|---|---|
| CH₂CH₂Ph | H | HCl |
| CH₂(4-Cl)Ph | H | HCl |
| CH₂(2-OMe)Ph | H | |
| CH₂CH₂(3-OMe)Ph | H | |
| CH₂CH₂(3-OMe)Ph | H | HCl |
| CH₂CH₂(3-OH)Ph | H | |
| CH₂(2,4,6-Me)Ph | H | HCl |
| CH₂(2-CF₃)Ph | H | HCl |
| CH₂(2-CN)Ph | H | |
| CH₂(2-CONH₂)Ph | H | |
| CH₂(2-NH₂)Ph | H | |
| CH₂CH₂Ph | OMe | |
| CH₂CH₂Ph | OH | |
| CH₂(3-CN)Ph | H | |
| CH₂(3-CONH₂)Ph | H | |
| CH₂CH₂(3-OMe)Ph | F | |
| CH₂CH₂(3-OH)Ph | F | |
| CH₂CH₂(3-F)Ph | H | |
| CH₂CH₂(2-F)Ph | F | |
| CH₂CH₂(2-F)Ph | H | |

Examples of Typical Compounds 12

[Formula 31]

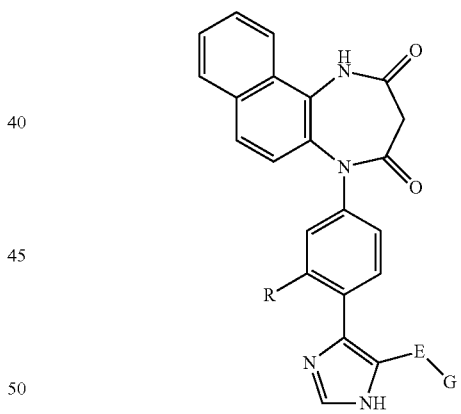

(In the formula, E-G, R, and type of salt are as mentioned in Table 27.)

TABLE 27

| E-G | R | Salt |
|---|---|---|
| bond—Ph | H | HCl |
| CH₂CH₂Ph | H | HCl |
| CH₂CH₂(2-F)Ph | H | |
| CH₂CH₂(3-F)Ph | F | |
| CH₂CH₂(2-OMe)Ph | F | |
| CH₂CH₂(3-OMe)Ph | F | |
| CH₂CH₂(2-OH)Ph | F | |
| CH₂CH₂(3-OH)Ph | F | |

Examples of Typical Compounds 13

[Formula 32]

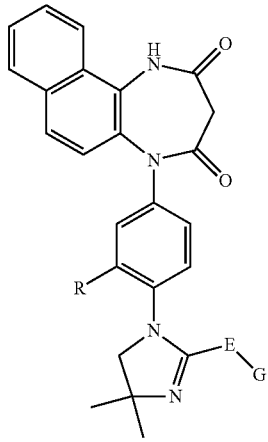

(In the formula, E-G, R, and type of salt are as mentioned in Table 28.)

TABLE 28

| E-G | R | Salt |
|---|---|---|
| $CH_2CH_2Ph$ | H | HCl |
| $CH_2CH_2$(2-F)Ph | H | |
| $CH_2CH_2$(3-F)Ph | F | |
| $CH_2CH_2$(2-OMe)Ph | F | |
| $CH_2CH_2$(3-OMe)Ph | F | |
| $CH_2CH_2$(2-OH)Ph | F | |
| $CH_2CH_2$(3-OH)Ph | F | |

Hereafter, the pharmacological efficacies of the compounds of the present invention will be described.

The P2X4 receptor antagonist activities of the compounds of the present invention were measured as follows.

The ATP receptor (human P2X4) was introduced into the 1321N1 cells, and the cells were used as a stable ATP receptor expression system. The P2X4-expressing 1321N1 cells were seeded on a 96-well plate, cultured under the conditions of 37° C. and 5% $CO_2$ for 24 hours, and used for calcium measurement. Fura-2 AM, which is a calcium fluorescent indicator, was dissolved in an extracellular fluid for calcium imaging, and the seeded cells were treated with the solution, and left standing at room temperature for 45 minutes so that Fura-2 AM was incorporated into the cells. For the measurement, a microplate reader, Fluostar Optima (BMG Labtech), was used. The light emitted from a xenon lamp was passed through 340 nm and 380 nm filters, respectively, and irradiated on the cells, fluorescences of 510 nm, $F_{340}$ and $F_{380}$, emitted from the cells were measured, and change of the ratio $F_{340}/F_{380}$ was used as an index of change of intracellular calcium level. The measurement was performed by adding ATP to each well at a final concentration of 1 μM, and observing the ATP-induced $Ca^{2+}$ response over time. In the measurement, a treatment with a test substance was performed 15 minutes before the addition of ATP, and the inhibitory activity of the test substance was calculated by comparison of the result with the result obtained in the absence of the test substance.

As clearly seen from the results for the compounds of Examples 84 and 85, the compounds of the present invention showed superior P2X4 receptor antagonist activity (Tables 29 to 31).

Further, analgesic activities of the compounds of the present invention (compounds of Examples 21 and 42) were measured by orally administering them to a mouse neuropathic pain model. As a result, it became clear that the compounds have superior analgesic activity (Example 86, FIG. 1).

Therefore, the diazepine derivatives represented by the aforementioned general formula (I) or (II), and pharmacologically acceptable salts thereof have a P2X4 receptor antagonist activity, and accordingly, it is considered that they are useful as prophylactic or therapeutic agents for pains of nociceptive pain, inflammatory pain, and neuropathic pain. More specifically, they are useful as prophylactic and therapeutic agents for pains accompanying various cancers, pains accompanying diabetic nerve damage, pains accompanying viral diseases such as herpes, arthrosis deformans, and the like. The prophylactic or therapeutic agent of the present invention may be used together with other medicaments if needed, and may be used together with, for example, opioid analgesics (morphine, fentanyl), sodium channel blockers (Novocain, lidocaine), NSAIDs (aspirin, ibuprofen), and the like. Further, when it is used for cancerous pain, it may be used together with, for example, anticancer agents such as anticancer chemotherapeutic agents.

The compounds of the present invention can be administered to a human by an appropriate administration method, such as oral administration or parenteral administration, but oral administration is preferred.

For manufacturing pharmaceutical preparations containing the compounds of the present invention, dosage forms such as tablets, granules, powders, capsules, suspensions, injections, and suppositories can be prepared by the methods usually used in the field of pharmaceutical manufacturing.

For manufacturing such preparations, in the case of tablets, for example, usual excipients, disintegrating agents, binders, lubricants, dyes, and the like are used. Examples of excipient include lactose, D-mannitol, crystalline cellulose, glucose, and the like, examples of disintegrating agent include starch, carboxymethylcellulose calcium (CMC-Ca), and the like, examples of lubricant include magnesium stearate, talc, and the like, and examples of binder include hydroxypropylcellulose (HPC), gelatin, polyvinylpyrrolidone (PVP), and the like. For manufacturing injection, solvents, stabilizers, dissolving aids, suspending agents, emulsifiers, soothing agents, buffering agents, preservatives, and the like are used.

As for the administration dose, the compounds of the present invention as the active ingredient can usually be administered to an adult in a daily dose of about 0.01 to 100 mg in the case of injection, or a daily dose of 1 to 2000 mg in the case of oral administration, but the dose may be increased or decreased depending on age, symptoms, and the like.

The compounds of the present invention include highly safe compounds such as those not showing the hERG potassium ion channel inhibitory activity, and they are also superior P2X4 receptor antagonists that can be made into easily-taken preparations for oral administration. Therefore, they are useful as prophylactic and therapeutic agents for nociceptive pain, inflammatory pain, and neuropathic pain.

Hereafter, the present invention will be explained in more detail with reference to examples. However, the present invention is not limited to these examples.

Example 1

5-[4-[5-(2-Methoxybenzyl)-1H-tetrazol-1-yl]phenyl]-1H-naphtho[1,2-b][1,4]diazepine-2,4(3H,5H)-dione

(1) tert-Butyl 4-(1-nitronaphthalen-2-yl-amino)phenylcarbamate

1-Nitro-2-naphthyl trifluoromethanesulfonate (20.26 g, 63.07 mmol), tert-butyl 4-aminophenylcarbamate (13.13 g, 63.07 mmol), triphenylphosphine (1.65 g, 6.31 mmol), tetrakis(triphenylphosphine)palladium(0) (3.64 g, 3.15 mmol), potassium carbonate (8.72 g, 63.07 mmol), and degassed dry toluene (600 mL) were mixed, and the mixture was refluxed by heating for 6 hours under a nitrogen atmosphere. The reaction mixture was left to cool, and then the insoluble matter was separated by filtration, and washed with ethyl acetate. The organic layer was washed with saturated aqueous sodium hydrogencarbonate, and dried over anhydrous sodium sulfate. The solvent was evaporated under reduced pressure, the residue was purified by silica gel column chromatography (hexane/ethyl acetate=4/1), and then the resultant was recrystallized from ethyl acetate/hexane to obtain the title compound (18.67 g, yield 78%) as yellow crystals.

$^1$H NMR (CDCl$_3$, 400 MHz) δ: 1.54 (9H, s), 6.53 (1H, s), 7.21 (2H, d, J=9 Hz), 7.21 (1H, d, J=9 Hz), 7.37 (1H, t, J=7 Hz), 7.44 (2H, d, J=9 Hz), 7.62 (1H, dt, J=1 Hz, 9 Hz), 7.68 (1H, d, J=7 Hz), 7.70 (1H, d, J=9 Hz), 8.61 (1H, d, J=9 Hz), 9.67 (1H, s)

(2) tert-Butyl 4-(1-amino-2-naphthylamino)phenylcarbamate tert-Butyl 4-(1-nitro-2-naphthylamino)phenylcarbamate (1.8.67 g, 49.21 mmol) was dissolved in tetrahydrofuran (180 mL) and methanol (180 mL), platinum oxide (360 mg) was added to the solution, and the resulting mixture was stirred at room temperature for 2 hours under a hydrogen atmosphere. The catalyst was separated by filtration, then the solvent was evaporated under reduced pressure, and the residue was washed with methanol to obtain the title compound (15.67 g, yield 91%) as grayish white crystals.

$^1$H NMR (DMSO-d$_6$, 400 MHz) δ: 1.45 (9H, s), 5.25 (2H, br s), 6.62 (2H, d, J=9 Hz), 7.0-7.3 (5H, m), 7.3-7.4 (2H, m), 7.72 (1H, d, J=8 Hz), 8.06 (1H, d, J=8 Hz), 8.90 (1H, br s)

(3) 5-(4-Aminophenyl)-1H-naphtho[1,2-b][1,4]diazepine-2,4(3H,5H)-dione tert-Butyl 4-(1-amino-2-naphthylamino)phenylcarbamate (3.00 g, 8.58 mmol), and sodium hydrogencarbonate (2.16 g, 25.7 mmol) were suspended in chloroform (60 mL), ethyl (chloroformyl)acetate (1.22 mL, 9.5 mmol) was added dropwise to the suspension over 1 minute with stirring under ice cooling. This reaction mixture was stirred for 1 hour under ice cooling, then water was added to the reaction mixture, the resulting mixture was stirred for 10 minutes, and the chloroform layer was dried over anhydrous sodium sulfate. The solvent was evaporated under reduced pressure to obtain a crude product of ethyl 3-[[2-[[4-[(tert-butoxycarbonyl)amino]phenyl]amino]-1-naphthyl]amino]-3-oxopropionate (4 g) as brown crystals. This crude product (4 g) was dissolved in dry tetrahydrofuran (172 mL), 60% sodium hydride (1.72 g, 42.9 mmol) was added to the solution over 1 minute with stirring under ice cooling, and the resulting mixture was stirred under ice cooling for 30 minutes, and then at room temperature for 3 hours. Saturated aqueous ammonium chloride was added to this reaction mixture with stirring under ice cooling, and the organic layer was dried over anhydrous sodium sulfate. The solvent was evaporated under reduced pressure to obtain a crude product of 5-(4-tert-butoxycarbonylaminophenyl)-1H-naphtho[1,2-b][1,4]diazepine-2,4(3H,5H)-dione (4 g) as pale brown crystals. This crude product (4 g) was suspended in dichloromethane (176 mL), trifluoroacetic acid (13.1 mL, 176 mL) was added dropwise to the suspension over 10 minutes with stirring under ice cooling, and then the resulting mixture was stirred under ice cooling for 1 hour, and then at room temperature for 16 hours. The solvent was evaporated at room temperature, saturated aqueous sodium hydrogencarbonate and ethyl acetate were added to the residue, and the mixture was stirred at room temperature for 2 hours. The deposited crystals were collected by filtration, and washed with water and then with ethyl acetate to obtain the title compound (1.23 g, yield 45%) as brown crystals.

$^1$H NMR (DMSO-d$_6$, 400 MHz) δ: 3.10 (1H, d, J=12 Hz), 3.61 (1H, d, J=12 Hz), 5.26 (2H, s), 6.58 (2H, d, J=9 Hz), 6.84 (2H, d, J=8 Hz), 7.04 (1H, d, J=9 Hz), 7.57 (1H, t, J=7 Hz), 7.6-7.7 (2H, m), 7.90 (1H, d, J=8 Hz), 8.22 (1H, d, J=8 Hz), 10.80 (1H, s)

(4) N-[4-(2,4-Dioxo-2,3-dihydro-1H-naphtho[1,2-b][1,4]diazepin-5(2H)-yl)phenyl]-2-(2 methoxyphenyl) acetamide 2-Methoxyphenylacetic acid (75 mg, 0.45 mmol) was treated with thionyl chloride, and thereby made into 2-methoxyphenylacetyl chloride, and the resultant and 5-(4-aminophenyl)-1H-naphtho[1,2-b][1,4]diazepine-2,4(3H,5H)-dione (95 mg, 0.3 mmol) were heated in pyridine to obtain the title compound (83 mg, yield 60%) as pale yellow crystals.

$^1$H NMR (DMSO-d$_6$, 400 MHz) δ: 3.14 (1H, d, J=12 Hz), 3.64 (2H, s), 3.69 (1H, d, J=12 Hz), 3.77 (3H, s), 6.90 (1H, t, J=7 Hz), 6.9-7.0 (2H, m), 7.15 (2H, d, J=8 Hz), 7.2-7.3 (2H, m), 7.59 (1H, t, J=8 Hz), 7.6-7.7 (4H, m), 7.91 (1H, d, J=8 Hz), 8.25 (1H, d, J=8 Hz), 10.17 (1H, s), 10.86 (1H, s)

(5) 5-[4-[5-(2-Methoxybenzyl)-1H-tetrazol-1-yl]phenyl]-1H-naphtho[1,2-b][1,4]diazepine-2,4(3H,5H)-dione Sodium azide (215 mg, 3.3 mmol), silicon tetrachloride (0.25 mL, 2.2 mmol), and dry acetonitrile (11 mL) were mixed, and the mixture was stirred at room temperature for 1 hour. To this suspension, 5-[4-[(2-Methoxyphenylacetyl)amino]phenyl]-1H-naphtho[1,2-b][1,4]diazepine-2,4(3H,5H)-dione (102 mg, 0.22 mmol) was added, and the resulting mixture was stirred at room temperature for 70 hours. To this reaction mixture, ice flakes, saturated aqueous sodium hydrogencarbonate, and ethyl acetate were added, and the resulting mixture was stirred for 10 minutes. The ethyl acetate layer was washed with saturated brine, and dried over anhydrous sodium sulfate. The solvent was evaporated under reduced pressure, and the residue was purified by silica gel column chromatography (methanol/chloroform=1/100) to obtain the title compound (18 mg, yield 17%) as pale yellow powder.

$^1$H NMR (DMSO-d$_6$, 400 MHz) δ: 3.20 (1H, d, J=12 Hz), 3.57 (3H, s), 3.77 (1H, d, J=12 Hz), 4.28 (2H, s), 6.86 (1H, t, J=7 Hz), 6.90 (1H, d, J=8 Hz), 6.97 (1H, d, J=9 Hz), 7.12 (1H, d, J=7 Hz), 7.25 (1H, t, J=7 Hz), 7.46 (2H, d, J=8 Hz), 7.6-7.7 (4H, m), 7.78 (1H, d, J=9 Hz), 7.97 (1H, d, J=8 Hz), 8.29 (1H, d, J=8 Hz), 10.96 (1H, s)

Example 2

5-[4-[5-(2-Hydroxybenzyl)-1H-tetrazol-1-yl]phenyl]-1H-naphtho[1,2-b][1,4]diazepine-2,4(3H,5H)-dione 5-[4-[5-(2-Methoxybenzyl)]-1H-tetrazol-1-yl]phenyl]-1H-naphtho[1,2-b][1,4]diazepine-2,4(3H,5H)-dione (18 mg, 0.037 mmol) was dissolved in dry dichloromethane (1.8 mL), a 1 M solution of boron tribromide in dichloromethane (0.18 mL) was added to the solution, and the mixture was stirred at room temperature for 16 hours. The solvent was evaporated, saturated aqueous sodium hydrogencarbonate was added to the residue, and the mixture was extracted with ethyl acetate. The ethyl acetate layer was washed with saturated brine, and dried over anhydrous sodium sulfate. The solvent was evaporated under reduced pressure, and the residue was recrystallized from ethyl acetate/hexane to obtain the title compound (9 mg, yield 54%) as slightly brown crystals.

$^1$H NMR (DMSO-$d_6$, 400 MHz) δ: 3.19 (1H, d, J=12 Hz), 3.77 (1H, d, J=12 Hz), 4.24 (2H, s), 6.7-6.8 (2H, m), 6.96 (1H, d, J=9 Hz), 7.00 (1H, d, J=7 Hz), 7.07 (1H, dd, J=1 Hz, 7 Hz), 7.45 (2H, d, J=9 Hz), 7.6-7.7 (4H, m), 7.78 (1H, d, J=9 Hz), 7.97 (1H, d, J=8 Hz), 8.29 (1H, d, J=9 Hz), 9.51 (1H, s), 10.96 (1H, s)

Example 3

5-[4-[5-[2-(Pyridin-3-yl)ethyl]-1H-tetrazol-1-yl]phenyl]-1H-naphtho[1,2-b][1,4]diazepine-2,4(3H, 5H)-dione hydrochloride (1) $N^1$-(1-Nitronaphthalen-2-yl)benzene-1,4-diamine 1-Nitro-2-naphthyl trifluoromethanesulfonate (1.61 g, 5 mmol), p-phenylenediamine (2.70 g, 25 mmol), triphenylphosphine (0.13 g, 0.5 mmol), tetrakis(triphenylphosphine)palladium(0) (0.29 g, 0.25 mmol), potassium carbonate (0.69 g, 5 mmol), and dry tetrahydrofuran (50 mL) were mixed, and the mixture was refluxed by heating for 4 hours under a nitrogen atmosphere. The reaction mixture was left to cool, then water was added to the mixture, the resulting mixture was extracted with ethyl acetate, and the insoluble matter was separated by filtration.

The ethyl acetate layer was washed with saturated brine, and dried over anhydrous sodium sulfate. The solvent was evaporated under reduced pressure, and the residue was purified by silica gel column chromatography (chloroform) to obtain the title compound (1.18 g, yield 84%) as red crystals.

$^1$H NMR (CDCl$_3$, 400 MHz) δ: 3.77 (2H, s), 6.7-6.8 (2H, m), 7.0-7.1 (2H, m), 7.13 (1H, d, J=9 Hz), 7.35 (1H, dt, J=1 Hz, 8 Hz), 7.61 (1H, ddd, J=1 Hz, 7 Hz, 8 Hz), 7.6-7.7 (2H, m), 8.71 (1H, d, J=9 Hz), 9.88 (1H, s)

(2) N-[4-(1-Nitronaphthalen-2-ylamino)phenyl]-3-(pyridin-3-yl)propanamide $N^1$-(1-Nitronaphthalen-2-yl)benzene-1,4-diamine (80 mg, 0.286 mmol) obtained above, 3-(3-pyridinyl)propionic acid (47 mg, 0.314 mmol), N,N,N',N'-tetramethyl-O-(7-azabenzotriazol-1-yl)uronium hexafluorophosphate (163 mg, 0.429 mmol), diisopropylethylamine (255 μL, 1.43 mmol), and dichloromethane (5 mL) were mixed, and the mixture was stirred at room temperature for 2 hours under a nitrogen atmosphere. To the reaction mixture, saturated aqueous sodium hydrogencarbonate was added, the resulting mixture was extracted with chloroform, and the organic layer was washed with saturated brine, and dried over anhydrous sodium sulfate. The solvent was evaporated under reduced pressure, and the residue was purified by silica gel chromatography (methanol/chloroform=2/100) to obtain the title compound (116 mg, yield 99%) as reddish brown oil.

$^1$H NMR (CDCl$_3$, 400 MHz) δ: 2.71 (2H, t, J=7 Hz), 3.09 (2H, t, J=7 Hz), 7.2-7.3 (4H, m), 7.38 (1H, t, J=9 Hz), 7.55 (2H, d, J=9 Hz), 7.6-7.7 (2H, m), 7.71 (3H, t, J=9 Hz), 8.49 (2H, d, J=2 Hz), 8.58 (1H, d, J=9 Hz), 9.59 (1H, s)

(3) 1-Nitro-N-[4-[5-[2-(pyridin-3-yl)ethyl]-1H-tetrazol-1-yl]phenyl]naphthalen-2-amine Sodium azide (278 mg, 4.29 mmol) was suspended in acetonitrile (2 mL), silicon tetrachloride (327 μL, 2.86 mmol) was added to the suspension, and the mixture was stirred at room temperature for 1 hour under a nitrogen atmosphere. To this reaction mixture, N-[4-(1-nitronaphthalen-2-ylamino)phenyl]-3-(pyridin-3-yl)propanamide (116 mg, 0.286 mmol) suspended in acetonitrile (4 mL) was added with stirring, and the resulting mixture was stirred with heating at 80° C. for 18 hours. The reaction mixture was left to cool to room temperature, then saturated aqueous sodium hydrogencarbonate was added to the reaction mixture with stirring under ice cooling, the resulting mixture was extracted with chloroform, and the organic layer was washed with saturated brine, and dried over anhydrous sodium sulfate. The solvent was evaporated under reduced pressure, and the residue was purified by silica gel chromatography (methanol/ethyl acetate=5/100) to obtain the title compound (94 mg, yield 76%) as reddish brown oil.

$^1$H NMR (CDCl$_3$, 400 MHz) δ: 3.22 (4H, s), 7.2-7.3 (3H, m), 7.36 (2H, d, J=9 Hz), 7.4-7.5 (3H, m), 7.67 (1H, d, J=7 Hz), 7.79 (1H, d, J=9 Hz), 7.89 (1H, d, J=9 Hz), 8.38 (1H, d, J=9 Hz), 8.40 (1H, d, J=2 Hz), 8.45 (1H, dd, J=2.5 Hz), 8.97 (1H, s)

(4) $N^2$-[4-[5-[2-(Pyridin-3-yl)ethyl]-1H-tetrazol-1-yl]phenyl]naphthalene-1,2-diamine 1-Nitro-N-[4-[5-[2-(pyridin-3-yl)ethyl]-1H-tetrazol-1-yl]phenyl]naphthalen-2-amine (94 mg, 0.216 mmol) obtained above was dissolved in tetrahydrofuran (1 mL) and methanol (1 mL), 10% palladium carbon (90 mg) was added to the solution, and the resulting mixture was stirred at room temperature for 30 minutes under a hydrogen atmosphere. The catalyst was separated by filtration, then the solvent was evaporated under reduced pressure, and the residue was purified by silica gel chromatography (methanol/chloroform=1/100) to obtain the title compound (75 mg, yield 86%) as pale yellow oil.

$^1$H NMR (CDCl$_3$, 400 MHz) δ: 3.15 (4H, s), 5.66 (1H, s), 6.74 (2H, d, J=9 Hz), 7.01 (2H, d, J=9 Hz), 7.1-7.5 (7H, m), 7.8-7.9 (2H, m), 8.38 (1H, d, J=2 Hz), 8.45 (1H, dd, J=2 Hz, 5 Hz)

(5) Ethyl 3-oxo-3-[2-[4-[5-[2-(pyridin-3-yl)ethyl]-1H-tetrazol-1-yl]phenylamino]naphthalen-1-ylamino]propionate $N^2$-[4-[5-[2-(Pyridin-3-yl)ethyl]-1H-tetrazol-1-yl]phenyl]naphthalene-1,2-diamine (75 mg, 0.185 mmol) obtained above, and triethylamine (77 μL, 0.555 mmol) were dissolved in dichloromethane (2 mL), and ethyl (chloroformyl)acetate (35 μL, 0.277 mmol) was added dropwise to the mixture with stirring under ice cooling. This reaction mixture was stirred at room temperature for 1 hour. To the reaction mixture, saturated aqueous sodium hydrogencarbonate was added, the resulting mixture was extracted with chloroform, and the organic layer was washed with saturated brine, and dried over anhydrous sodium sulfate. The solvent was evaporated under reduced pressure, and the residue was purified by silica gel chromatography (methanol/chloroform=1/100) to obtain the title compound (38 mg, yield 40%) as pale yellow oil.

$^1$H NMR (CDCl$_3$, 400 MHz) δ: 1.37 (3H, t, J=7 Hz), 3.17 (4H, s), 3.68 (2H, s), 4.34 (2H, q, J=7 Hz), 7.0-7.2 (6H, m), 7.4-7.6 (4H, m), 7.81 (1H, d, J=9 Hz), 7.85 (1H, d, J=9 Hz), 7.98 (1H, d, J=9 Hz), 8.37 (1H, d, J=2 Hz), 8.46 (1H, dd, J=2 Hz, 5 Hz), 9.72 (1H, s)

(6) 5-[4-[5-[2-(Pyridin-3-yl)ethyl]-1H-tetrazol-1-yl]phenyl]-1H-naphtho[1,2-b][1,4]diazepine-2,4(3H,5H)-dione Ethyl 3-oxo-3-[2-[4-[5-[2-(pyridin-3-yl)ethyl]-1H-tetrazol-1-yl]phenylamino]naphthalen-1-ylamino]propionate (38 mg, 0.0741 mmol) obtained above was dissolved in dry tetrahydrofuran (1 mL), 60% sodium hydride (9.7 mg, 0.244 mmol) was added to the solution with stirring under ice cooling, and the mixture was stirred under ice cooling for 10 minutes, and then at room temperature for 1 hour. To this reaction mixture, saturated aqueous ammonium chloride was added with stirring under ice cooling, the resulting mixture was extracted with chloroform, and the organic layer was washed with saturated brine, and dried over anhydrous sodium sulfate. The solvent was evaporated under reduced pressure, and the residue was purified by silica gel chromatography (methanol/chloroform=5/100) to obtain the title compound (34 mg, yield 97%) as a slightly brown amorphous substance.

$^1$H NMR (DMSO-d$_6$, 400 MHz) δ: 3.09 (2H, t, J=7 Hz), 3.20 (1H, d, J=12 Hz), 3.3-3.4 (2H, m), 3.78 (1H, d, J=12 Hz), 7.06 (1H, d, J=9 Hz), 7.2-7.3 (1H, m), 7.49 (2H, d, J=9 Hz), 7.6-7.8 (6H, m), 7.95 (1H, d, J=7 Hz), 8.29 (1H, d, J=9 Hz), 8.39 (2H, dd, J=2 Hz, 5 Hz), 10.97 (1H, s)

(7) 5-[4-[5-[2-(Pyridin-3-yl)ethyl]-1H-tetrazol-1-yl]phenyl]-1H-naphtho[1,2-b][1,4]diazepine-2,4(3H,5H)-dione hydrochloride 5-[4-[5-(Pyridin-3-ylethyl)-1H-tetrazol-1-yl]phenyl]-1H-naphtho[1,2-b][1,4]diazepine-2,4(3H,5H)-dione (34 mg, 0.073 mmol) obtained above was dissolved in methanol (1 mL), a 2 M solution of hydrogen chloride in methanol (1 mL) was added to the solution, and the solvent was evaporated under reduced pressure. The residue was concentrated from water under reduced pressure, and then dried at 60° C. for 3 hours under reduced pressure to obtain the title compound (28 mg, yield 75%) as a slightly brown amorphous substance.

$^1$H NMR (DMSO-d$_6$, 400 MHz) δ: 3.20 (1H, d, J=12 Hz), 3.3-3.4 (4H, m), 3.78 (1H, d, J=12 Hz), 7.05 (1H, d, J=9 Hz), 7.51 (2H, d, J=9 Hz), 7.63 (1H, t, J=7 Hz), 7.6-7.7 (4H, m), 7.82 (1H, t, J=7 Hz), 7.95 (1H, d, J=9 Hz), 8.31 (2H, t, J=7 Hz), 8.69 (1H, d, J=5 Hz), 8.78 (1H, s), 10.97 (1H, s)

Example 4

5-[4-(5-Phenethyl-1H-tetrazol-1-yl)phenyl]-1H-naphtho[1,2-b][1,4]diazepine-2,4(3H,5H)-dione By using N$^1$-(1-nitronaphthalen-2-yl)benzene-1,4-diamine (60 mg, 0.215 mmol) obtained in Example 3, (1), and 3-phenylpropionic acid (35 mg, 0.233 mmol), the title compound was obtained as pale yellow powder in the same manner as that of Example 3.

$^1$H NMR (DMSO-d$_6$, 400 MHz) δ: 3.05 (2H, t, J=8 Hz), 3.21 (1H, d, J=12 Hz), 3.24 (2H, t, J=8 Hz), 3.77 (1H, d, J=12 Hz), 7.04 (1H, d, J=9 Hz), 7.1-7.3 (5H, m), 7.47 (2H, d, J=9 Hz), 7.6-7.7 (4H, m), 7.75 (1H, d, J=9 Hz), 7.95 (1H, d, J=7 Hz), 8.29 (1H, d, J=9 Hz), 10.97 (1H, s)

Example 5

5-[4-[5-(Pyridin-4-ylmethyl)-1H-tetrazol-1-yl]phenyl]-1H-naphtho[1,2-b][1,4]diazepine-2,4(3H,5H)-dione By using N$^1$-(1-nitronaphthalen-2-yl)benzene-1,4-diamine (60 mg, 0.215 mmol) obtained in Example 3, (1), and 2-(pyridin-4-yl)acetic acid hydrochloride (41 mg, 0.233 mmol), the title compound was obtained as pale yellow powder in the same manner as that of Example 3.

$^1$H NMR (DMSO-d$_6$, 400 MHz) δ: 3.20 (1H, d, J=12 Hz), 3.77 (1H, d, J=12 Hz), 4.46 (2H, s), 6.95 (1H, d, J=9 Hz), 7.19 (2H, d, J=5 Hz), 7.47 (2H, d, J=9 Hz), 7.5-7.8 (4H, m), 7.77 (1H, d, J=9 Hz), 7.97 (1H, d, J=8 Hz), 8.29 (1H, d, J=9 Hz), 8.47 (2H, d, J=5 Hz), 10.97 (1H, s)

Example 6

5-[4-(5-Benzyl-1H-tetrazol-1-yl)phenyl]-1H-naphtho[1,2-b][1,4]diazepine-2,4(3H,5H)-dione N$^1$-(1-Nitronaphthalen-2-yl)benzene-1,4-diamine (60 mg, 0.215 mmol) obtained in Example 3, (1), phenylacetyl chloride (34 μL, 0.257 mmol), triethylamine (90 μL, 0.645 mmol), and dichloromethane (2 mL) were mixed, and the mixture was stirred at room temperature for 3 hours under a nitrogen atmosphere. To the reaction mixture, saturated aqueous sodium hydrogencarbonate was added, the resulting mixture was extracted with chloroform, and the organic layer was washed with saturated brine, and dried over anhydrous sodium sulfate. The solvent was evaporated under reduced pressure, and the residue was purified by silica gel chromatography (chloroform) to obtain reddish brown powder (98 mg, yield 100%). The resulting product was treated in the same manner as that of Example 3, (3), (4), (5), and (6) to obtain the title compound as pale red powder.

$^1$H NMR (DMSO-d$_6$, 400 MHz) δ: 3.20 (1H, d, J=12 Hz), 3.76 (1H, d, J=12 Hz), 4.40 (2H, s), 6.95 (1H, d, J=9 Hz), 7.0-7.1 (2H, m), 7.2-7.3 (3H, m), 7.45 (2H, d, J=9 Hz), 7.6-7.7 (4H, m), 7.78 (1H, d, J=9 Hz), 7.97 (1H, d, J=8 Hz), 8.29 (1H, d, J=8 Hz), 10.96 (1H, s)

Example 7

5-[4-[5-(Pyridin-3-ylmethyl)-1H-tetrazol-1-yl]phenyl]-1H-naphtho[1,2-b][1,4]diazepine-2,4(3H,5H)-dione By using $N^1$-(1-nitronaphthalen-2-yl)benzene-1,4-diamine (57 mg, 0.204 mmol) obtained in Example 3, (1), and 2-(pyridin-3-yl)acetic acid (31 mg, 0.226 mmol), the title compound was obtained as pale yellow powder in the same manner as that of Example 3, (3), (4), (5), and (6).

$^1$H NMR (DMSO-$d_6$, 400 MHz) δ: 3.20 (1H, d, J=12 Hz), 3.77 (1H, d, J=12 Hz), 4.45 (2H, s), 6.99 (1H, d, J=9 Hz), 7.31 (1H, dd, J=4 Hz, 8 Hz), 7.48 (2H, d, J=9 Hz), 7.6-7.8 (6H, m), 7.97 (1H, d, J=8 Hz), 8.29 (1H, d, J=8 Hz), 8.40 (1H, d, J=2 Hz), 8.47 (1H, dd, J=2 Hz, 4 Hz), 10.96 (1H, s)

Example 8

7-Methoxy-1-[4-[5-(2-methoxybenzyl)-1H-tetrazol-1-yl]phenyl]-1H-benzo[b][1,4]diazepine-2,4(3H,5H)-dione By using N-(4-methoxy-2-nitrobenzen-1-yl)-benzene-1,4-diamine (100 mg, 0.39 mmol), and 2-methoxyphenylacetic acid (64 mg, 0.47 mmol), the title compound was obtained as pale yellow crystals in the same manner as that of Example 3, (3), (4), (5), and (6).

$^1$H NMR (DMSO-$d_6$, 400 MHz) δ: 3.10 (1H, br s), 3.56 (3H, s), 3.70 (1H, br s), 3.77 (3H, s), 4.25 (2H, s), 6.7-6.9 (5H, m), 7.11 (1H, d, J=7 Hz), 7.22 (1H, d, J=8 Hz), 7.38 (2H, d, J=9 Hz), 7.63 (2H, d, J=8 Hz), 10.57 (1H, br s)

Example 9

5-[6-[5-(2-Methoxybenzyl)-1H-tetrazol-1-yl]pyridin-3-yl]-1H-naphtho[1,2-b][1,4]diazepine-2,4(3H,5H)-dione

(1) 2-(2-Methoxyphenyl)-N-(5-nitropyridin-2-yl)acetamide

2-Methoxyphenylacetic acid (3.99 g, 24 mmol), ethyl acetate (40 mL), and thionyl chloride (3.46 mL, 48 mmol) were mixed, and the mixture was refluxed by heating for 4 hours. The solvent was evaporated under reduced pressure, and the residue was concentrated twice from dry tetrahydrofuran (10 mL) under reduced pressure to obtain brown oil. This 2-methoxyphenylacetyl chloride was dissolved in dry tetrahydrofuran (20 mL), the solution was added dropwise to a solution of 2-amino-5-nitropyridine (2.78 g, 20 mmol) in dry pyridine (20 mL) at room temperature over 10 minutes with stirring, and then the resulting mixture was stirred at room temperature for 19 hours. This reaction mixture was poured into cold water (160 mL), and the precipitates were ground, after stirring of the mixture for 1 hour, collected by filtration, and washed several times with water to obtain yellowish brown crystals. The crystals were dissolved in ethyl acetate, and the solution was washed with saturated aqueous sodium hydrogencarbonate, and then with saturated brine, and dried over anhydrous sodium sulfate. The solvent was evaporated under reduced pressure, and the residue was recrystallized from ethyl acetate/hexane to obtain the title compound (3.93 g, yield 73%) as pale brown crystals.

$^1$H NMR (CDCl$_3$, 400 MHz) δ: 3.79 (2H, s), 3.97 (3H, s), 6.9-7.1 (2H, m), 7.3-7.4 (2H, m), 8.36 (1H, d, J=9 Hz), 8.44 (1H, dd, J=2 Hz, 9 Hz), 8.85 (1H, brs), 9.08 (1H, d, J=2 Hz)

(2) 2-[5-(2-Methoxybenzyl)-1H-tetrazol-1-yl]-5-nitropyridine

Sodium azide (3.90 g, 60 mmol), silicon tetrachloride (4.6 mL, 40 mmol), and dry acetonitrile (16 mL) were mixed, and the mixture was stirred at room temperature for 1 hour and 30 minutes. To this suspension, 2-(2-methoxyphenyl)-N-(5-nitropyridin-2-yl)acetamide (1.09 g, 4 mmol), and dry acetonitrile (4 mL) were added, and the resulting mixture was stirred at room temperature for 23 hours. This reaction mixture was poured into a mixture of saturated aqueous sodium hydrogencarbonate (200 mL) and ice, and the resulting mixture was stirred for 1 hour. The mixture was extracted with ethyl acetate, and the organic layer was washed with saturated brine, and dried over anhydrous sodium sulfate. The solvent was evaporated under reduced pressure, and the residue was recrystallized from ethyl acetate/hexane to obtain the title compound (1.08 g, yield 86%) as yellow crystals.

$^1$H NMR (CDCl$_3$, 400 MHz) δ: 3.70 (3H, s), 4.77 (2H, s), 6.8-6.9 (2H, m), 7.08 (1H, d, J=6 Hz), 7.24 (1H, t, J=9 Hz), 8.26 (1H, d, J=9 Hz), 8.74 (1H, dd, J=3 Hz, 9 Hz), 9.36 (1H, d, J=3 Hz)

(3) 6-[5-(2-Methoxybenzyl)-1H-tetrazol-1-yl]pyridin-3-amine

2-[5-(2-Methoxybenzyl)-1H-tetrazol-1-yl]-5-nitropyridine (1.08 g, 3.45 mmol) was dissolved in tetrahydrofuran (10 mL) and methanol (2 mL), platinum oxide (11 mg) was added to the solution, and the mixture was stirred at room temperature for 16 hours under a hydrogen atmosphere. The solvent was evaporated under reduced pressure, and the residue was purified by silica gel column chromatography (chloroform/methanol=50/1) to obtain the title compound (0.93 g, yield 95%) as grayish white crystals.

$^1$H NMR (CDCl$_2$, 400 MHz) δ: 3.66 (3H, s), 4.01 (2H, bs), 4.56 (2H, s), 6.80 (1H, d, J=8 Hz), 6.84 (1H, dt, J=1 Hz, 8 Hz), 7.08 (1H, d, J=8 Hz), 7.13 (1H, dd, J=3 Hz, 8 Hz), 7.20 (1H, dt, J=2 Hz, 8 Hz), 7.52 (1H, d, J=9 Hz), 7.96 (1H, d, J=3 Hz)

(4) 6-[5-(2-Methoxybenzyl)-1H-tetrazol-1-yl]-N-(1-nitronaphthalen-2-yl)pyridin-3-amine 6-[5-(2-Methoxybenzyl)-1H-tetrazol-1-yl]pyridin-3-amine (907 mg, 3.2 mmol), 1-nitro-2-naphthyl trifluoromethanesulfonate (1028 mg, 3.2 mmol), triphenylphosphine (85 mg, 0.32 mmol), tetrakis(triphenylphosphine)palladium(0) (185 mg, 0.16 mmol), potassium carbonate (442 mg, 3.2 mmol), and dry tetrahydrofuran (16 mL) were mixed, and the mixture was refluxed by heating for 6 hours under a nitrogen atmosphere. The reaction mixture was left to cool, then water was added to the reaction mixture, the resulting mixture was extracted with ethyl acetate, and the organic layer was washed with saturated brine, and dried over anhydrous sodium sulfate. The solvent was evaporated under reduced pressure, and the residue was washed with acetone, and then with hexane to obtain the title compound (1.23 g, yield 85%) as pale yellow crystals.

$^1$H NMR (DMSO-$d_6$, 400 MHz) δ: 3.61 (3H, s), 4.47 (2H, s), 6.87 (1H, t, J=8 Hz), 6.94 (1H, d, J=8 Hz), 7.13 (1H, d, J=7 Hz), 7.25 (1H, t, J=7 Hz), 7.5-7.7 (2H, m), 7.71 (1H, t,

J=8 Hz), 7.7-7.9 (3H, m), 8.05 (1H, d, J=8 Hz), 8.16 (11H, d, J=9 Hz), 8.43 (1H, d, J=1 Hz), 9.23 (1H, s)

(5) 5-[6-[5-(2-Methoxybenzyl)-1H-tetrazol-1-yl] pyridin-3-yl]-1H-naphtho[1,2-b][1,4]diazepine-2,4 (3H,5H)-dione By using 6-[5-(2-methoxybenzyl)-1H-tetrazol-1-yl]-N-(1-nitronaphthalen-2-yl)pyridin-3-amine (1.23 g, 2.71 mmol), $N^2$-[6-[5-(2-methoxybenzyl)-1H-tetrazol-1-yl]pyridin-3-yl]naphthalene-1,2-diamine was obtained as brown oil in the same manner as that of Example 1, (3). This product was dissolved in chloroform (5.4 mL), 0.5 M aqueous sodium carbonate was added to the solution, and ethyl (chloroformyl)acetate (0.41 mL, 3.2 mmol) was added dropwise to the mixture over 1 minute with stirring under ice cooling. This mixture was stirred at room temperature for 1 hour, and then the chloroform layer was washed with saturated brine, and dried over anhydrous sodium sulfate. The solvent was evaporated under reduced pressure to obtain a crude product of ethyl 3-[2-[6-[5-(2-methoxybenzyl)-1H-tetrazol-1-yl]pyridin-3-ylamino]naphthalen-1-ylamino]-3-oxopropionate (1.8 g) as dark brown oil.

This product was dissolved in dry tetrahydrofuran (14 mL), 60% sodium hydride (216 mg, 5.4 mmol) was added to the solution over 1 minute with stirring under ice cooling, and the resulting mixture was stirred for 1 hour under ice cooling. To this reaction mixture, saturated aqueous ammonium chloride was added, the resulting mixture was extracted with tetrahydrofuran and ethyl acetate, and the organic layer was washed with saturated brine, and dried over anhydrous sodium sulfate. The solvent was evaporated under reduced pressure, and the residue was purified by silica gel column chromatography (methanol/chloroform=1/50), and the eluted substance was recrystallized from ethyl acetate/hexane to obtain the title compound (0.56 g, yield 42%) as brown crystals.

$^1$H NMR (CDCl$_3$, 400 MHz) δ: 3.65 (3H, s), 3.6-3.7 (2H, m), 4.68 (2H, s), 6.81 (1H, d, J=8 Hz), 6.86 (1H, t, J=8 Hz), 6.96 (1H, d, J=9 Hz), 7.11 (1H, d, J=7 Hz), 7.22 (1H, t, J=8 Hz), 7.6-7.7 (2H, m), 7.75 (1H, t, J=8 Hz), 7.8-8.0 (2H, m), 7.97 (1H, d, J=9 Hz), 8.13 (1H, d, J=9 Hz), 8.48 (1H, s), 8.74 (1H, s)

Example 10

5-[4-[5-(2-Cyclohexylethyl)-1H-tetrazol-1-yl]phenyl]-1H-naphtho[1,2-b][1,4]diazepine-2,4(3H,5H)-dione By using $N^1$-(1-nitronaphthalen-2-yl)benzene-1,4-diamine (60 mg, 0.215 mol) obtained in Example 3, (1), and 3-cyclohexylpropionic acid (41 μL, 0.233 mmol), the title compound was obtained as slightly brown powder in the same manner as that of Example 3, (3), (4), (5), and (6).

$^1$H NMR (DMSO-d$_6$, 400 MHz) δ: 0.8-0.9 (2H, m), 1.0-1.3 (4H, m), 1.5-1.7 (7H, m), 2.93 (2H, t, J=8 Hz), 3.21 (1H, d, J=12 Hz), 3.78 (1H, d, J=12 Hz), 7.03 (1H, d, J=9 Hz), 7.52 (2H, d, J=9 Hz), 7.6-7.8 (5H, m), 7.95 (1H, d, J=8 Hz), 8.30 (1H, d, J=8 Hz), 10.97 (1H, s)

Example 11

5-[6-[5-(2-Hydroxybenzyl)]-1H-tetrazol-1-yl]pyridin-3-yl]-1H-naphtho[1,2-b][1,4]diazepine-2,4(3H, 5H)-dione By using 5-[6-[5-(2-methoxybenzyl)]-1H-tetrazol-1-yl] pyridin-3-yl]-1H-naphtho[1,2-b][1,4]diazepine-2,4(3H, 5H)-dione (98 mg, 0.2 mmol), the title compound was obtained as slightly red crystals (41 mg, yield 43%) in the same manner as that of Example 2.

$^1$H NMR (CDCl$_3$, 400 MHz) δ: 3.6-3.8 (2H, m), 4.66 (1H, d, J=14 Hz), 4.71 (1H, d, J=14 Hz), 6.8-6.9 (2H, m), 7.00 (1H, d, J=9 Hz), 7.17 (1H, t, J=7 Hz), 7.34 (1H, d, J=7 Hz), 7.6-7.8 (3H, m), 7.9-8.0 (2H, m), 7.99 (1H, d, J=9 Hz), 8.0-8.2 (2H, m), 8.47 (1H, br s), 8.59 (1H, s)

Example 12

5-[4-[5-[2-(Pyridin-4-yl)ethyl]-1H-tetrazol-1-yl] phenyl]-1H-naphtho[1,2-b][1,4]diazepine-2,4(3H, 5H)-dione hydrochloride By using $N^1$-(1-nitronaphthalen-2-yl)benzene-1,4-diamine (80 mg, 0.286 mol) obtained in Example 3, (1), and 3-(4-pyridinyl)propionic acid (47 mg, 0.314 mmol), the title compound was obtained as white crystals in the same manner as that of Example 3, (3), (4), (5), and (6).

$^1$H NMR (DMSO-d$_6$, 400 MHz) δ: 3.20 (1H, d, J=12 Hz), 3.3-3.4 (4H, m), 3.79 (1H, d, J=12 Hz), 7.05 (1H, d, J=9 Hz), 7.51 (2H, d, J=9 Hz), 7.6-7.8 (7H, m), 7.95 (1H, d, J=7 Hz), 8.30 (1H, d, J=7 Hz), 8.65 (2H, s), 10.97 (1H, s)

Example 13

5-[4-[5-(Pyridin-2-ylmethyl)-1H-tetrazol-1-yl]phenyl]-1H-naphtho[1,2-b][1,4]diazepine-2,4(3H,5H)-dione By using $N^1$-(1-nitronaphthalen-2-yl)benzene-1,4-diamine (60 mg, 0.215 mmol) obtained in Example 3, (1), and 2-(pyridin-2-yl)acetic acid hydrochloride (41 mg, 0.233 mmol), the title compound was obtained as brown powder in the same manner as that of Example 3, (3), (4), (5), and (6).

$^1$H NMR (DMSO-d$_6$, 400 MHz) δ: 3.18 (1H, d, J=12 Hz), 3.75 (1H, d, J=12 Hz), 4.61 (2H, s), 6.87 (1H, d, J=9 Hz), 7.25 (1H, dd, J=5 Hz, 7 Hz), 7.32 (1H, d, J=8 Hz), 7.40 (2H, d, J=9 Hz), 7.6-7.8 (6H, m), 7.96 (1H, d, J=8 Hz), 8.28 (1H, d, J=8 Hz), 8.37 (1H, d, J=5 Hz), 10.95 (1H, s)

Example 14

5-[4-[5-[2-(Pyridin-2-yl)ethyl]-1H-tetrazol-1-yl] phenyl]-1H-naphtho[1,2-b][1,4]diazepine-2,4(3H, 5H)-dione hydrochloride By using $N^1$-(1-nitronaphthalen-2-yl)benzene-1,4-diamine (170 mg, 0.608 mol) obtained in Example 3, (1), and 3-(2-pyridinyl)propionic acid (101 mg, 0.668 mmol), the title compound was obtained as a slightly brown amorphous substance in the same manner as that of Example 3, (3), (4), (5), and (6).

$^1$H NMR (DMSO-d$_6$, 400 MHz) δ: 3.20 (1H, d, J=11 Hz), 3.3-3.4 (4H, m), 3.78 (1H, d, J=11 Hz), 7.05 (1H, d, J=9 Hz), 7.52 (3H, d, J=9 Hz), 7.6-7.8 (6H, m), 7.95 (2H, d, J=7 Hz), 8.29 (1H, d, J=7 Hz), 8.57 (1H, s), 10.99 (1H, s)

Example 15

5-[4-[5-[(1H-Imidazol-1-yl)methyl]-1H-tetrazol-1-yl]phenyl]-1H-naphtho[1,2-b][1,4]diazepine-2,4(3H, 5H)-dione (1) 2-Chloro-N-[4-(1-nitronaphthalen-2-ylamino) phenyl]acetamide By using $N^1$-(1-nitronaphthalen-2-yl)benzene-1,4-diamine (100 mg, 0.358 mmol) obtained in Example 3, (1), and chloroacetyl chloride (43 μL, 0.537 mmol), the title compound was obtained as reddish brown solid (112 mg, yield 88%) in the same manner as that of Example 6, (1).

$^1$H NMR (CDCl$_3$, 400 MHz) δ: 4.23 (2H, s), 7.2-7.3 (3H, m), 7.40 (1H, t, J=8 Hz), 7.6-7.7 (3H, m), 7.71 (1H, d, J=8 Hz), 7.75 (1H, d, J=9 Hz), 8.29 (1H, br s), 8.56 (1H, d, J=9 Hz), 9.54 (1H, s)

(2) 2-(1H-Imidazol-1-yl)-N-[4-(1-nitronaphthalen-2-ylamino)phenyl]acetamide

2-Chloro-N-[4-(1-nitronaphthalen-2-ylamino)phenyl]acetamide (112 mg, 0.315 mmol), imidazole (26 mg, 0.378 mmol), cesium carbonate (154 mg, 0.473 mmol), and acetonitrile (3 mL) were mixed, and the mixture was stirred at room temperature for 2 hours under a nitrogen atmosphere. To the reaction mixture, distilled water was added, the resulting mixture was extracted with chloroform, and the organic layer was dried over anhydrous sodium sulfate. The solvent was evaporated under reduced pressure, and the residue was purified by silica gel chromatography (methanol/chloroform=1/10) to obtain the title compound (122 mg, yield 100%) as reddish brown solid.

$^1$H NMR (CDCl$_3$, 400 MHz) δ: 4.85 (2H, s), 7.11 (2H, d, J=12 Hz), 7.2-7.3 (3H, m), 7.39 (1H, t, J=8 Hz), 7.51 (2H, d, J=9 Hz), 7.6-7.8 (4H, m), 8.54 (1H, d, J=8 Hz), 9.50 (1H, s)

(3) 5-[4-[5-[(1H-Imidazol-1-yl)methyl]-1H-tetrazol-1-yl]phenyl]-1H-naphtho[1,2-b][1,4]diazepine-2,4(3H,5H)-dione By using 2-(1H-imidazol-1-yl)-N-[4-(1-nitronaphthalen-2-ylamino)phenyl]acetamide (122 mg, 0.314 mmol) obtained above, the title compound was obtained as a slightly brown amorphous substance in the same manner as that of Example 3, (3), (4), (5), and (6).

$^1$H NMR (DMSO-d$_6$, 400 MHz) δ: 3.21 (1H, d, J=12 Hz), 3.78 (1H, d, J=12 Hz), 5.76 (2H, s), 6.89 (1H, s), 7.05 (1H, d, J=9 Hz), 7.10 (1H, s), 7.50 (2H, d, J=9 Hz), 7.6-7.8 (6H, m), 7.97 (1H, d, J=8 Hz), 8.29 (1H, d, J=9 Hz), 10.98 (1H, s)

Example 16

5-[4-[5-[2-(1H-Imidazol-1-yl)ethyl]-1H-tetrazol-1-yl]phenyl]-1H-naphtho[1,2-b][1,4]diazepine-2,4(3H,5H)-dione By using N$^1$-(1-nitronaphthalen-2-yl)benzene-1,4-diamine (300 mg, 1.07 mmol) obtained in Example 3, (1), and 3-(imidazol-1-yl)propionic acid (165 mg, 1.20 mmol), the title compound was obtained as pale yellow crystals in the same manner as that of Example 3, (3), (4), (5), and (6).

$^1$H NMR (DMSO-ds, 400 MHz) δ: 3.21 (1H, d, J=12 Hz), 3.63 (2H, t, J=6 Hz), 3.79 (1H, t, J=12 Hz), 4.73 (2H, t, J=6 Hz), 7.05 (1H, d, J=9 Hz), 7.53 (2H, d, J=8 Hz), 7.6-7.9 (7H, m), 7.95 (1H, d, J=8 Hz), 8.30 (1H, d, J=8 Hz), 9.21 (1H, s), 11.0 (1H, s)

Example 17

5-[4-[5-[2-(Pyridin-2-yl)ethyl]-1H-tetrazol-1-yl]phenyl]-1H-naphtho[1,2-e][1,4]diazepin-2(3H)-one dihydrochloride (1) 5-(4-Bromophenyl)-1H-naphtho[1,2-e][1,4]diazepin-2(3H)-one By using 1-nitro-2-naphthaldehyde, and 1-bromo-4-iodobenzene, the title compound was obtained in the same manner as that of the method described in WO2008/023847.

$^1$H NMR (DMSO-de, 400 MHz) δ: 3.80 (1H, d, J=9 Hz), 4.58 (1H, d, J=9 Hz), 7.26 (1H, d, J=8 Hz), 7.48 (2H, d, J=8 Hz), 7.6-7.8 (5H, m), 8.01 (1H, d, J=8 Hz), 8.36 (1H, d, J=9 Hz), 10.85 (1H, br s)

(2) 5-(4-Aminophenyl)-1H-naphtho[1,2-e][1,4]diazepin-2(3H)-one 5-(4-Bromophenyl)-1H-naphtho[1,2-e][1,4]diazepin-2(3H)-one (380 mg, 1.04 mmol), benzophenone imine (349 mg, 2.08 mmol), sodium tert-butoxide (200 mg, 2.08 mmol), palladium(II) acetate (23 mg, 0.104 mmol), and 4,5-bis(diphenylphosphino)-9,9-dimethylxanthene (60 mg, 0.208 mmol) were dissolved in anhydrous dioxane (5 mL), and the solution was stirred at 110° C. for 16 hours. The reaction mixture was left to cool, and then poured into water, and the resulting mixture was extracted with chloroform. The organic layer was washed with saturated brine, and dried over anhydrous sodium sulfate. The solvent was evaporated under reduced pressure, and the residue was purified by silica gel column chromatography (chloroform/methanol=100/1) to obtain the title compound (154 mg, yield 49%).

$^1$H NMR (DMSO-d$_6$, 400 MHz) δ: 3.67 (1H, d, J=10 Hz), 4.42 (1H, d, J=10 Hz), 5.57 (2H, s), 6.54 (2H, d, J=8 Hz), 7.24 (2H, d, J=8 Hz), 7.33 (1H, d, J=9 Hz), 7.6-7.8 (3H, m), 7.9-8.1 (1H, m), 8.3-8.4 (1H, m), 10.67 (1H, br s)

(3) N-[4-(2-Oxo-2,3-dihydro-1H-naphtho[1,2-e][1,4]diazepin-5-yl)phenyl]-3-(pyridin-2-yl)propanamide 5-(4-Aminophenyl)-1H-naphtho[1,2-e][1,4]diazepin-2(3H)-one (400 mg, 1.33 mmol) was dissolved in anhydrous DMF (15 mL) by heating. The reaction mixture was left to cool to room temperature, then 3-pyridin-2-yl-propanoic acid (221 mg, 1.46 mmol), and 1-(3-dimethylaminopropyl)-3-ethylcarbodiimide hydrochloride (382 mg, 1.99 mmol) were added to the mixture, and the resulting mixture was stirred at room temperature for 16 hours. To the reaction mixture, saturated aqueous sodium hydrogencarbonate was added, the resulting mixture was extracted with ethyl acetate, and the organic layer was dried over anhydrous sodium sulfate. The solvent was evaporated under reduced pressure, chloroform was added to the residue, and the deposited crystals were collected by filtration, and washed with chloroform and hexane to obtain the title compound (408 mg, yield 71%) as grayish white crystals.

$^1$H NMR (DMSO-dc, 400 MHz) δ: 2.79 (2H, t, J=7 Hz), 3.06 (2H, t, J=7 Hz), 3.76 (1H, d, J=10 Hz), 4.53 (1H, d, J=10 Hz), 7.19 (1H, dd, J=2 Hz, 5 Hz), 7.27 (1H, d, J=6 Hz), 7.29 (1H, d, J=4 Hz), 7.47 (2H, d, J=9 Hz), 7.6-7.8 (6H, m), 7.9-8.1 (1H, m), 8.35 (1H, d, J=9 Hz), 8.35 (1H, d, J=9 Hz), 8.47 (1H, d, J=4 Hz), 10.18 (1H, s), 10.80 (1H, s)

(4) N-[4-[1-(4-Methoxybenzyl)-2-oxo-2,3-dihydro-1H-naphtho[1,2-e][1,4]diazepin-5-yl]phenyl]-3-(pyridin-2-yl)propanamide N-[4-(2-Oxo-2, 3-dihydro-1H-naphtho[1,2-e][1,4]diazepin-5-yl)phenyl]-3-(pyridin-2-yl)propanamide (100 mg, 0.230 mmol) was dissolved in anhydrous DMF (1.5 mL) by heating, and the solution was left to cool to room temperature. Potassium carbonate (95 mg, 0.69 mmol), and 4-methoxybenzyl chloride (33 μL, 0.242 mmol) were added to the solution, and the mixture was stirred at room temperature for 16 hours. To the reaction mixture, water was added, and the resulting mixture was extracted with ethyl acetate. The organic layer was dried over anhydrous sodium sulfate, and the solvent was evaporated under reduced pressure. The residue was purified by silica gel column chromatography (chloroform/methanol=9/1) to obtain the title compound (124 mg, yield 97%) as a pale yellow amorphous substance.

$^1$H NMR (CDCl$_3$, 400 MHz) δ: 2.8-3.0 (2H, m), 3.2-3.3 (2H, m), 3.55 (3H, s), 3.80 (1H, d, J=10 Hz), 4.43 (1H, d, J=14 Hz), 4.85 (1H, d, J=10 Hz), 5.93 (1H, d, J=14 Hz), 6.39 (2H, d, J=9 Hz), 6.64 (2H, d, J=9 Hz), 7.13 (2H, dd, J=1 Hz, 8 Hz), 7.1-7.2 (1H, m), 7.2-7.3 (2H, m), 7.46 (2H, d, J=8 Hz), 7.6-7.8 (4H, m), 7.93 (1H, d, J=8 Hz), 8.17 (1H, d, J=8 Hz), 8.61 (1H, d, J=5 Hz), 9.75 (1H, br s)

(5) 1-(4-Methoxybenzyl)-5-[4 [5-[2-(pyridin-2-yl) ethyl]-1H-tetrazol-1-yl]phenyl]-1H-naphtho[1,2-e] [1,4]diazepin-2(3H)-one Sodium azide (218 mg, 3.35 mmol) was suspended in acetonitrile (3 mL), silicon chloride (257 μL, 2.24 mmol) was added to the suspension under a nitrogen atmosphere, and the mixture was stirred at room temperature for 1 hour. A solution of N-[4-[1-(4-methoxybenzyl)-2-oxo-2,3-dihydro-1H-naphtho[1,2-e][1,4]diazepin-5-yl]phenyl]-3-(pyridin-2-yl)propanamide (124 mg, 0.224 mmol) in acetonitrile (1 mL) was added to the mixture, and the resulting mixture was refluxed by heating for 9 hours. The reaction mixture was left to cool to room temperature, then saturated aqueous sodium hydrogencarbonate was added to the mixture, and the resulting mixture was extracted with chloroform. The insoluble matter was separated by filtration, then the organic layer was dried over anhydrous sodium sulfate, and the solvent was evaporated under reduced pressure. The residue was purified by silica gel column chromatography (chloroform/methanol=19/1) to obtain the title compound (25 mg, yield 19%) as a pale yellow amorphous substance.

$^1$H NMR (CDCl$_3$, 400 MHz) δ: 3.43 (4H, s), 3.52 (3H, s), 3.86 (1H, d, J=10 Hz), 4.43 (1H, d, J=14 Hz), 4.95 (1H, d, J=10 Hz), 5.99 (1H, d, J=14 Hz), 6.41 (2H, d, J=9 Hz), 6.64 (2H, d, J=8 Hz), 7.1-7.4 (7H, m), 7.59 (1H, dt, J=2 Hz, 8 Hz), 7.6-7.8 (3H, m), 7.97 (1H, d, J=8 Hz), 8.20 (1H, d, J=8 Hz), 8.4-8.5 (1H, m)

(6) 5-[4-[5-[2-(Pyridin-2-yl)ethyl]-1H-tetrazol-1-yl] phenyl]-1H-naphtho[1,2-e][1,4]diazepin-2 (3H)-one 1-(4-Methoxybenzyl)-5-[4-[5-[2-(pyridin-2-yl)ethyl]-1H-tetrazol-1-yl]phenyl]-1H-naphtho[1,2-e][1,4]diazepin-2 (3H)-one (25 mg, 0.043 mmol) was dissolved in anisole (0.5 mL), and aluminum chloride (23 mg, 0.172 mmol) was added to the solution. The resulting mixture was stirred at 85° C. for 2 hours, and left to cool to room temperature. To the reaction mixture, saturated aqueous sodium hydrogencarbonate was added, and the resulting mixture was extracted with chloroform. The organic layer was dried over anhydrous sodium sulfate, and the solvent was evaporated under reduced pressure. The residue was purified by silica gel column chromatography (chloroform/methanol=19/1) and amino-silica gel column chromatography (chloroform) to obtain the title compound (15 mg, yield 76%) as white crystals.

$^1$H NMR (DMSO-d$_6$, 400 MHz) δ: 2.8-3.2 (4H, m), 3.88 (1H, br s), 4.63 (1H, br s), 7.17 (1H, dd, J=2 Hz, 5 Hz), 7.25 (1H, d, J=8 Hz), 7.34 (1H, d, J=8 Hz), 7.66 (1H, dt, J=2 Hz, 8 Hz), 7.6-7.8 (6H, m), 7.78 (1H, t, J=8 Hz), 8.0-8.1 (1H, m), 8.3-8.4 (2H, m), 10.92 (1H, br s)

(7) 5-[4-[5-[2-(Pyridin-2-yl)ethyl]-1H-tetrazol-1-yl] phenyl]-1H-naphtho[1,2-e][1,4]diazepin-2(3H)-one dihydrochloride 5-[4-s[5-[2-(Pyridin-2-yl)ethyl]-1H-tetrazol-1-yl]phenyl]-1H-naphtho[1,2-e][1,4]diazepin-2(3H)-one (28 mg, 0.061 mmol) was dissolved in ethyl acetate (1 mL), a 4 M solution of hydrogen chloride in ethyl acetate (100 μL) was added to the solution, and the resulting mixture was stirred at room temperature for 0.5 hour. The deposited crystals were collected by filtration, washed with ethyl acetate, and then air-dried to obtain the title compound (24 mg, yield 74%) as yellow crystals.

$^1$H NMR (DMSO-d$_6$, 400 MHz) δ: 3.0-3.8 (4H, m), 3.90 (1H, br s), 4.64 (1H, br s), 7.33 (1H, d, J=9 Hz), 7.6-7.9 (9H, m), 8.0-8.1 (1H, m), 8.22 (1H, br s), 8.40 (1H, d, J=9 Hz), 8.67 (1H, d, J=5 Hz), 10.96 (1H, s)

Example 18

5-[4-[5-(2-Methoxyphenethyl) 1H-tetrazol-1-yl] phenyl]-1H-naphtho[1,2-b][1,4]diazepine-2,4(3H, 5H)-dione By using N$^1$-(1-nitronaphthalen-2-yl)benzene-1,4-diamine (80 mg, 0.286 mol) obtained in Example 3, (1), and 3-(2-methoxyphenyl)propionic acid (56 mg, 0.314 mmol), the title compound was obtained in the same manner as that of Example 3, (3), (4), (5), and (6) as a slightly brown amorphous substance.

$^1$H NMR (DMSO-d$_6$, 400 MHz) δ: 2.95 (2H, t, J=8 Hz), 3.1-3.2 (3H, m), 3.64 (3H, s), 3.78 (1H, d, J=12 Hz), 6.80 (1H, t, J=8 Hz), 6.87 (1H, d, J=8 Hz), 6.98 (1H, dd, J=2 Hz, 5 Hz), 7.03 (1H, d, J=9 Hz), 7.17 (1H, t, J=8 Hz), 7.47 (2H, d, J=9 Hz), 7.55 (2H, d, J=9 Hz), 7.6-7.7 (2H, m), 7.76 (1H, d, J=9 Hz), 7.95 (1H, d, J=8 Hz), 8.29 (1H, d, J=9 Hz), 10.98 (1H, s)

Example 19

5-[4-[5-(2-Methoxybenzyl)-1H-tetrazol-1-yl]phenyl]-1H-naphtho[1,2-e][1,4]diazepin-2(3H)-one (1) 2-(2-Methoxyphenyl)-N-[4-(2-oxo-2,3-dihydro-1H-naphtho[1,2-e][1,4]diazepin-5-yl)phenyl]acetamide 5-(4-Aminophenyl)-1H-naphtho[1,2-e][1,4]diazepin-2 (3H)-one (151 mg, 0.5 mmol), 2-methoxyphenylacetic acid (100 mg, 0.6 mmol), HATU (228 mg, 0.6 mmol), diisopropylethylamine (0.1 mL, 0.6 mmol), and dry dimethylformamide (5 mL) were mixed, and the mixture was stirred at room temperature for 16 hours. To this reaction mixture, water was added, the resulting mixture was extracted with ethyl acetate, and the organic layer was washed with saturated aqueous sodium hydrogencarbonate, and then with saturated brine, and dried over anhydrous sodium sulfate. The solvent was evaporated under reduced pressure, and the residue was washed with chloroform, and then with hexane to obtain the title compound (116 mg) as pale yellow crystals. This washing solution was concentrated under reduced pressure, and the residue was purified by silica gel column chromatography (chloroform/methanol=50/1) to obtain the title compound (63 mg) as white crystals (total 179 mg, yield 80%).

$^1$H NMR (DMSO-d$_6$, 400 MHz) δ: 3.66 (2H, s), 3.7-3.8 (4H, m), 4.54 (1H, d, J=10 Hz), 6.90 (1H, t, J=7 Hz), 6.98 (1H, d, J=8 Hz), 7.2-7.3 (3H, m), 7.49 (2H, d, J=8 Hz), 7.6-7.8 (5H, m), 8.01 (1H, d, J=6 Hz), 8.36 (1H, d, J=7 Hz), 10.26 (1H, s), 10.81 (1H, s)

(2) 5-[4-[5-(2-Methoxybenzyl)-1H-tetrazol-1-yl]phenyl]-1,3-dihydronaphtho[1,2-e][1,4]diazepin-2-one By using 2-(2-methoxyphenyl)-N-[4-(2-oxo-2,3-dihydro 1H-naphtho[1,2-e][1,4]diazepin-5-yl)phenyl]acetamide (179 mg, 0.4 mmol), the title compound (3 mg, yield 2%) was obtained as pale brown powder in the same manner as that of Example 1, (5).

$^1$H NMR (CDCl$_3$, 400 MHz) δ: 3.67 (3H, s), 4.28 (2H, s), 6.80 (1H, d, J=8 Hz), 6.89 (1H, t, J=7 Hz), 7.08 (1H, d, J=7 Hz), 7.2-7.3 (1H, m), 7.44 (2H, d, J=8 Hz), 7.6-7.8 (6H, m), 7.9-8.0 (1H, m), 8.1-8.2 (1H, m), 8.31 (1H, s)

Example 20

5-[4-[5-(3-Phenylpropyl)-1H-tetrazol-1-yl]phenyl]-1H-naphtho[1,2-b][1,4]diazepine-2,4(3H,5H)-dione By using N$^1$-(1-nitronaphthalen-2-yl)benzene-1,4-diamine (60 mg, 0.215 mmol) obtained in Example 3, (1), and 4-phenylbutyric acid (39 mg, 0.236 mmol), the title compound was obtained as a pale yellow amorphous substance in the same manner as that of Example 3.

$^1$H NMR (DMSO-d$_6$, 400 MHz) δ: 2.01 (2H, quint, J=8 Hz), 2.63 (2H, t, J=8 Hz), 2.91 (2H, t, J=8 Hz), 3.21 (1H, d, J=12 Hz), 3.79 (1H, d, J=12 Hz), 7.02 (1H, d, J=9 Hz), 7.13 (2H, d, J=7 Hz), 7.16 (1H, d, J=7 Hz), 7.2-7.3 (2H, m), 7.49 (2H, d, J=9 Hz), 7.6-7.7 (1H, m), 7.7-7.8 (4H, m), 7.96 (1H, d, J=8 Hz), 8.30 (1H, d, J=9 Hz), 11.00 (1H, s)

Example 21

5-[4-(2-Phenethyl-1H-imidazol-1-yl)phenyl]-1H-naphtho[1,2-b][1,4]diazepine-2,4(3H,5H)-dione hydrochloride (1) N-[4-(1-Nitronaphthalen-2-ylamino]phenyl]-3-phenylpropanethioamide By using N$^1$-(1-nitronaphthalen-2-yl)benzene-1,4-diamine (300 mg, 1.07 mmol) obtained in Example 3, (1), and 3-phenylpropionic acid (177 mg, 1.20 mmol), a crude product of N-[4-(1-nitronaphthalen-2-ylamino)phenyl]-3-phenylpropanamide was obtained as orange powder in the same manner as that of Example 3, (2). The resulting crude product was dissolved in toluene (5 mL) and THF (5 mL), 2,4-bis(4-methoxyphenyl)-1,3-dithia-2,4-diphosphetane-2,4-disulfide (433 mg, 1.07 mmol) was added to the solution, and the mixture was stirred with heating at 100° C. for 16 hours with. The reaction mixture was left to cool to room temperature, then saturated aqueous sodium hydrogencarbonate was added to the reaction mixture with stirring under ice cooling, the resulting mixture was extracted with chloroform, and the organic layer was washed with saturated brine, and dried over anhydrous sodium sulfate. The solvent was evaporated under reduced pressure, and the residue was purified by silica gel chromatography (methanol/chloroform=1/100) to obtain the title compound (290 mg, yield 63%) as reddish brown oil.

$^1$H NMR (CDCl$_3$, 400 MHz) δ: 3.13 (2H, t, J=7 Hz), 3.22 (2H, t, J=7 Hz), 7.20-7.45 (9H, m), 7.49 (2H, d, J=8 Hz), 7.63 (1H, d, J=7 Hz), 7.73 (1H, d, J=8 Hz), 7.77 (1H, d, J=9 Hz), 8.30 (1H, br s), 8.51 (1H, d, J=9 Hz), 9.41 (1H, br s)

(2) (Z)—N'-(2,2-Diethoxyethyl)-N-4-[(1-nitronaphthalen-2-ylamino)phenyl]-3-phenylpropanimidamide N-[4-(1-Nitronaphthalen-2-ylamino)phenyl]-3-phenylpropanethioamide (190 mg, 0.44 mmol) obtained above was dissolved in ethanol (1 mL) and THF (1 mL), aminoacetal (640 μL, 4.44 mmol) was added to the solution, and the resulting mixture was stirred with heating at 90° C. for 16 hours. The reaction mixture was left to cool to room temperature, then saturated aqueous sodium hydrogencarbonate was added to the reaction mixture with stirring under ice cooling, the resulting mixture was extracted with chloroform, and the organic layer was washed with saturated brine, and dried over anhydrous sodium sulfate. The solvent was evaporated under reduced pressure, and the residue was purified by silica gel chromatography (methanol/chloroform=1/100) to obtain the title compound (290 mg, yield 63%) as reddish brown oil.

$^1$H NMR (CDCl$_3$, 400 MHz) δ: 1.24 (6H, t, J=7 Hz), 2.58 (2H, t, J=7 Hz), 2.78 (2H, t, J=7 Hz), 3.4-3.6 (4H, m), 3.6-3.8 (2H, m), 4.5-4.7 (2H, m), 6.71 (2H, d, J=8 Hz), 7.0-7.4 (9H, m), 7.61 (1H, t, J=8 Hz), 7.68 (1H, d, J=9 Hz), 7.69 (1H, d, J=9 Hz), 8.68 (1H, d, J=9 Hz), 9.89 (1H, br s)

(3) 1-Nitro-N-[4-(2-phenethyl-1H-imidazol-1-yl)phenyl]naphthalen-2-amine (Z)—N'-(2,2-Diethoxyethyl)-N-4-[(1-nitronaphthalen-2-ylamino)phenyl]-3-phenylpropanimidamide (230 mg, 0.44 mmol) obtained above was dissolved in toluene (10 mL) and THF (1 mL), 10-camphorsulfonic acid (204 mg, 0.88 mmol) was added to the solution, and the resulting mixture was stirred with heating at 110° C. for 16 hours. The reaction mixture was left to cool to room temperature, then saturated aqueous sodium hydrogencarbonate was added to the reaction mixture with stirring under ice cooling, the resulting mixture was extracted with chloroform, and the organic layer was washed with saturated brine, and dried over anhydrous sodium sulfate. The solvent was evaporated under reduced pressure, and the residue was purified by silica gel chromatography (methanol/chloroform=1/100) to obtain the title compound (191 mg, yield 100%) as reddish brown oil.

$^1$H NMR (CDCl$_3$, 400 MHz) δ: 2.9-3.0 (2H, m), 3.0-3.2 (2H, m), 6.97 (1H, d, J=1 Hz), 7.0-7.3 (10H, m), 7.4-7.5 (2H, m), 7.65 (1H, dt, J=2 Hz, 7 Hz), 7.75 (1H, d, J=9 Hz), 7.82 (1H, d, J=9 Hz), 8.45 (1H, d, J=9 Hz), 9.25 (1H, br s)

(4) N$^2$-[4-[2-Phenethyl-1H-imidazol-1-yl)phenyl]naphthalene-1,2-diamine

By using 1-nitro-N-[4-(2-phenethyl-1H-imidazol-1-yl)phenyl]naphthalen-2-amine (240 mg, 0.55 mmol) obtained above, the title compound (222 mg, yield 100%) was obtained as a slightly brown amorphous substance in the same manner as that of Example 3, (4).

¹H NMR (CDCl₃, 400 MHz) δ: 2.8-3.0 (2H, m), 3.0-3.1 (2H, m), 4.29 (2H, br s), 5.57 (1H, br s), 6.67 (2H, d, J=9 Hz), 6.8-7.0 (31H, m), 7.0-7.4 (8H, m), 7.4-7.6 (2H, m), 7.7-7.9 (2H, m)

(5) Ethyl 3-oxo-3-[2-[4-(2-phenethyl-1H-imidazol-1-yl)phenylamino]naphthalen-1-ylamino]propionate By using N²-[4-[2-phenethyl-1H-imidazol-1-yl]phenyl]naphthalene-1,2-diamine (222 mg, 0.55 mmol) obtained above, the title compound (207 mg, yield 73%) was obtained as a slightly brown amorphous substance in the same manner as that of Example 3, (5).
¹H NMR (CDCl₃, 400 MHz): δ: 1.35 (3H, t, J=7 Hz), 2.80-2.95 (2H, m), 2.95-3.10 (2H, m), 3.67 (2H, s), 4.32 (2H, q, J=7 Hz), 6.8-7.3 (11H, m), 7.42 (1H, t, J=7 Hz), 7.55 (1H, t, J=7 Hz), 7.61 (1H, d, J=9 Hz), 7.76 (1H, d, J=9), 7.81 (1H, d, J=8 Hz), 7.94 (1H, d, J=8 Hz), 9.66 (1H, br s)

(6) 5-[4-(2-Phenethyl-1H-imidazol-1-yl)phenyl]-1H-naphtho[1,2-b][1,4]diazepine-2,4(3H,5H)-dione By using ethyl 3-oxo-3-[2-[4-(2-phenethyl-1H-imidazol-1-yl)phenylamino]naphthalen-1-ylamino]propionate (207 mg, 0.40 mmol) obtained above, the title compound (23 mg, yield 12%) was obtained as pale yellow crystals in the same manner as that of Example 3, (6).
¹H NMR (CDCl₃, 400 MHz) δ: 2.9-3.0 (2H, m), 3.0-3.1 (2H, m), 3.64 (2H, s), 6.9-7.4 (12H, m), 7.6-7.7 (2H, m), 7.72 (1H, t, J=7 Hz), 7.88 (1H, d, J=8 Hz), 8.12 (1H, d, J=8 Hz), 8.92 (1H, br s)

(7) 5-[4-(2-Phenethyl-1H-imidazol-1-yl)phenyl]-1H-naphtho[1,2-b][1,4]diazepine-2,4(3H,5H)-dione hydrochloride By using 5-[4-(2-phenethyl-1H-imidazol-1-yl)phenyl]-1H-naphtho[1,2-b][1,4]diazepine-2,4(3H,5H)-dione (207 mg, 0.40 mmol) obtained above, the title compound (25 mg, yield 100%) was obtained as pale yellow crystals in the same manner as that of Example 3, (7).
¹H NMR (DMSO-d₆, 400 MHz) δ: 2.97 (2H, br s), 3.1-3.3 (3H, m), 3.78 (1H, d, J=12 Hz), 6.9-7.1 (3H, m), 7.1-7.3 (3H, m), 7.4-7.6 (4H, m), 7.63 (1H, t, J=8 Hz), 7.70 (1H, t, J=8 Hz), 7.76 (1H, d, J=9 Hz), 7.83 (1H, s), 7.92 (1H, s), 7.96 (1H, d, J=8 Hz), 8.30 (1H, d, J=8 Hz), 11.0 (1H, br s)

Example 22

5-[4-(1-Phenethyl-1H-imidazol-2-yl)phenyl]-1H-naphtho[1,2-b][1,4]diazepine-2,4(3H,5H)-dione hydrochloride (1) 2-(4-Nitrophenyl)-1-phenethyl-1H-imidazole 2-(4-Nitrophenyl)-1H-imidazole [Heterocycles, 76, 507 (2008)](0.89 g, 4.7 mmol), (2-bromoethyl)benzene (1.74 g, 9.4 mmol), potassium carbonate (0.97 g, 7.05 mmol), and dimethylformamide (9 mL) were mixed, and the mixture was stirred at 120° C. for 24 hours. To this reaction mixture, ice flakes were added, the resulting mixture was extracted with ethyl acetate, and the organic layer was washed twice with water, and then with saturated brine, and dried over anhydrous sodium sulfate. The solvent was evaporated under reduced pressure, and the residue was purified by silica gel column chromatography (methanol/chloroform=1/100) to obtain the title compound (0.37 g, yield 27%) as yellow oil.
¹H NMR (CDCl₃, 400 MHz) δ: 3.03 (2H, t, J=7 Hz), 4.28 (2H, t, J=7 Hz), 6.9-7.0 (2H, m), 7.06 (1H, d, J=1 Hz), 7.19 (1H, d, J=1 Hz), 7.2-7.3 (3H, m), 7.4-7.5 (2H, m), 8.1-8.3 (2H, m)

(2) 4-(1-Phenethyl-1H-imidazol-2-yl)aniline 2-(4-Nitrophenyl)-1-phenethyl-1H-imidazole (390 mg, 1.33 mmol) obtained above was dissolved in methanol (4 mL), platinum oxide (4 mg) was added to the solution, and the resulting mixture was stirred at room temperature for 17 hours under a hydrogen atmosphere. The solvent was evaporated under reduced pressure, and the residue was purified by silica gel column chromatography (methanol/chloroform=1/50) to obtain the title compound (274 mg, yield 78%) as brown oil.
¹H NMR (CDCl₂, 400 MHz) δ: 2.99 (2H, dd, J=7 Hz, 8 Hz), 3.80 (2H, bs), 4.18 (2H, dd, J=7 Hz, 8 Hz), 6.6-6.7 (2H, m), 6.88 (1H, d, J=1 Hz), 7.0-7.1 (2H, m), 7.06 (1H, d, J=1 Hz), 7.2-7.3 (5H, m)

(3) 1-Nitro-N-[4-(1-phenethyl-1H-imidazol-2-yl)phenyl]naphthalen-2-amine

By using 4-(1-phenethyl-1H-imidazol-2-yl)aniline (274 mg, 1.04 mmol) obtained above, and 1-nitro-2-naphthyl trifluoromethanesulfonate (321 mg, 1 mmol), the title compound (280 mg, yield 64%) was obtained in the same manner as that of Example 9, (4) as red crystals.
¹H NMR (CDCl₃, 400 MHz) δ: 3.03 (2H, t, J=7 Hz), 4.26 (2H, t, J=7 Hz), 6.9-7.1 (3H, m), 7.14 (1H, d, J=1 Hz), 7.2-7.3 (5H, m), 7.3-7.5 (4H, m), 7.63 (1H, t, J=7 Hz), 7.73 (1H, d, J=8 Hz), 7.79 (1H, d, J=9 Hz), 8.49 (1H, d, J=9 Hz), 9.41 (1H, s)

(4) Ethyl 3-oxo-3-[2-[4-(1-phenethyl-1H-imidazol-2-yl)phenylamino]naphthalen-1-ylamino]propionate 1-Nitro-N-[4-(1-phenethyl-1H-imidazol-2-yl)phenyl]naphthalen-2-amine (102 mg, 0.23 mmol) obtained above was dissolved in tetrahydrofuran (5 mL), methanol (5 mL) and platinum oxide (2 mg) were added to the solution, and the mixture was stirred at room temperature for 20 hours under a hydrogen atmosphere. The catalyst was separated by filtration, and then the solvent was evaporated under reduced pressure to obtain brown oil. This N²-[4-(1-phenethyl-1H-imidazol-2-yl)phenyl]naphthalene-1,2-diamine was dissolved in chloroform (5 mL), and 0.5 M aqueous sodium carbonate (0.5 mL) was added to the solution. To this mixture, ethyl (chloroformyl)acetate (0.04 mL, 0.32 mmol) was added with stirring under ice cooling, and the mixture was stirred at room temperature for 2 hours. The chloroform layer was washed with saturated brine, and dried over anhydrous sodium sulfate. The solvent was evaporated under reduced pressure, and the residue was purified by silica gel column chromatography (methanol/chloroform=1/50) to obtain the title compound (69 mg, yield 55%) as pale yellow oil.
¹H NMR (CDCl₃, 400 MHz) δ: 1.30 (3H, t, J=7 Hz), 2.95 (2H, t, J=7 Hz), 3.62 (2H, s), 4.16 (2H, t, J=7 Hz), 4.26 (2H, q, J=7 Hz), 6.8-6.9 (4H, m), 6.9-7.0 (2H, m), 7.05 (2H, d, J=8 Hz), 7.11 (1H, d, J=1 Hz), 7.2-7.3 (3H, m), 7.38 (1H, t, J=8 Hz), 7.50 (1H, t, J=7 Hz), 7.58 (1H, d, J=9 Hz), 7.72 (1H, d, J=9 Hz), 7.79 (1H, d, J=8 Hz), 7.99 (1H, d, J=8 Hz), 10.61 (1H, s)

(5) 5 [4-(1-Phenethyl-1H-imidazol-2-yl)phenyl]-1H-naphtho[1,2-b][1,4]diazepine-2,4(3H,5H)-dione By using ethyl 3-oxo-3-[2-[4-(1-phenethyl-1H-imidazol-2-yl)phenylamino]naphthalen-1-ylamino]propionate (69 mg, 0.13 mmol) obtained above, the title compound was obtained in the same manner as that of Example 3, (6) (20 mg, yield 32%) as white oil.

$^1$H NMR (CDCl$_3$, 400 MHz) δ: 3.01 (2H, t, J=7 Hz), 3.63 (2H, s), 4.24 (2H, t, J=7 Hz), 6.98 (4H, d, J=9 Hz), 7.13 (1H, d, J=1 Hz), 7.2-7.3 (5H, m), 7.37 (2H, d, J=8 Hz), 7.5-7.6 (2H, m), 7.69 (1H, t, J=7 Hz), 7.86 (1H, d, J=8 Hz), 8.17 (1H, d, J=8 Hz), 9.36 (1H, s)

(6) 5-[4-(1-Phenethyl-1H-imidazol-2-yl)phenyl]-1H-naphtho[1,2-b][1,4]diazepine-2,4(3H,5H)-dione hydrochloride 5-[4-(1-Phenethyl-1H-imidazol-2-yl)phenyl]-1H-naphtho[1,2-b][1,4]diazepine-2,4(3H,5H)-dione (20 mg, 0.042 mmol) obtained above was dissolved in chloroform (2 mL), a 4 M solution of hydrogen chloride in ethyl acetate (0.05 mL) was added to the solution, and the solvent was evaporated under reduced pressure. The residue was washed with ethyl acetate, and concentrated from water under reduced pressure to obtain the title compound (18 mg, yield 83%) as a slightly brown amorphous substance.

$^1$H NMR (CDCl$_3$, 400 MHz) δ: 3.05 (2H, s), 3.60 (2H, q, J=12 Hz), 4.44 (2H, s), 6.85 (2H, s), 6.96 (11H, d, J=8 Hz), 7.2-7.4 (9H, m), 7.6-7.7 (2H, m), 7.72 (1H, t, J=8 Hz), 7.87 (1H, d, J=8 Hz), 8.20 (1H, d, J=8 Hz), 9.20 (1H, s)

Example 23

5-[4-[1-(4-Chlorobenzyl)-1H-imidazol-2-yl]phenyl]-1H-naphtho[1,2-b][1,4]diazepine-2,4(3H,5H)-dione hydrochloride

(1) 1-(4-Chlorobenzyl)-2-(4-nitrophenyl)-1H-imidazole

By using 2-(4-nitrophenyl)-1H-imidazole [Heterocycles, 76, 507 (2008)](378 mg, 2 mmol), and 4-chlorobenzyl bromide (616 mg, 3 mmol), the title compound (320 mg, yield 51%) was obtained as yellow crystals in the same manner as that of Example 22, (1).

$^1$H NMR (CDCl$_3$, 400 MHz) δ: 5.26 (2H, s), 7.01 (2H, d, J=8 Hz), 7.06 (1H, d, J=1 Hz), 7.27 (1H, d, J=1 Hz), 7.35 (2H, d, J=8 Hz), 7.73 (2H, d, J=9 Hz), 8.26 (2H, d, J=9 Hz)

(2) N-[4-[1-(4-Chlorobenzyl)-1H-imidazol-2-yl]phenyl]-1-nitronaphthalen-2-amine 1-(4-Chlorobenzyl)-2-(4-nitrophenyl)-1H-imidazole (320 mg, 1.02 mmol) obtained above was dissolved in methanol (32 mL), platinum oxide (3 mg) was added to the solution, and the mixture was stirred at room temperature for 17 hours under a hydrogen atmosphere. The catalyst was separated by filtration, and then the solvent was evaporated under reduced pressure to obtain a brown amorphous substance. By using this 4-[1-(4-chlorobenzyl)-1H-imidazol-2-yl]aniline, and 1-nitro-2-naphthyl trifluoromethanesulfonate (321 mg, 1 mmol), the title compound (243 mg, yield 53%) was obtained as a red amorphous substance in the same manner as that of Example 9, (4).

$^1$H NMR (CDCl$_3$, 400 MHz) δ: 5.23 (2H, s), 6.98 (1H, d, J=1 Hz), 7.03 (2H, d, J=8 Hz), 7.21 (1H, d, J=1 Hz), 7.29 (2H, d, J=9 Hz), 7.34 (2H, d, J=8 Hz), 7.4-7.5 (2H, m), 7.56 (2H, d, J=9 Hz), 7.6-7.7 (2H, m), 7.73 (1H, d, J=8 Hz), 7.79 (1H, d, J=9 Hz), 8.47 (1H, d, J=9 Hz), 9.35 (1H, s)

(3) N$^2$-[4-[1-(4-Chlorobenzyl)-1H-imidazol-2-yl]phenyl]naphthalene-1,2-diamine By using N-[4 [1-(4-chlorobenzyl)-1H-imidazol-2-yl]phenyl]-1-nitronaphthalen-2-amine (243 mg, 0.53 mmol) obtained above, the title compound (157 mg, yield 70%) was obtained as pale brown crystals in the same manner as that of Example 22, (2).

$^1$H NMR (CDCl$_3$, 400 MHz) δ: 4.38 (2H, s), 5.17 (2H, s), 5.43 (1H, s), 6.69 (2H, d, J=9 Hz), 6.90 (1H, d, J=1 Hz), 7.00 (2H, d, J=8 Hz), 7.15 (1H, d, J=1 Hz), 7.2-7.4 (6H, m), 7.4-7.5 (2H, m), 7.8-7.9 (2H, m)

(4) Ethyl 3-[[2-[[4-[1-(4-chlorobenzyl)-1H-imidazol-2-yl]phenyl]amino]naphthalen-1-yl]amino]-3-oxopropionate By using N$^2$-[4-[1-(4-chlorobenzyl)-1H-imidazol-2-yl]phenyl]naphthalene-1,2-diamine (157 mg, 0.37 mmol) obtained above, and ethyl (chloroformyl)acetate (0.06 mL, 0.47 mmol), the title compound (152 mg, yield 76%) was obtained as pale yellow oil in the same manner as that of Example 22, (4).

$^1$H NMR (CDCl$_3$, 400 MHz) δ: 1.28 (3H, t, J=7 Hz), 3.61 (2H, s), 4.24 (2H, q, J=7 Hz), 5.09 (2H, s), 6.8-6.9 (4H, m), 6.93 (2H, d, J=8 Hz), 7.1-7.2 (3H, m), 7.2-7.3 (2H, m), 7.36 (1H, t, J=8 Hz), 7.48 (1H, t, J=8 Hz), 7.54 (1H, d, J=9 Hz), 7.69 (1H, d, J=9 Hz), 7.76 (1H, d, J=8 Hz), 7.97 (1H, d, J=8 Hz), 10.59 (1H, s)

(5) 5-[4-[1-(4-Chlorobenzyl)-1H-imidazol-2-yl]phenyl]-1H-naphtho[1,2-b][1,4]diazepine-2,4(3H,5H)-dione By using ethyl 3-[[2-[[4-[1-(4-chlorobenzyl)-1H-imidazol-2-yl]phenyl]amino]naphthalen-1-yl]amino]-3-oxopropionate (152 mg, 0.28 mmol) obtained above, the title compound (44 mg, yield 32%) was obtained as grayish white crystals in the same manner as that of Example 3, (6).

$^1$H NMR (DMSO-d$_6$, 400 MHz) δ: 3.16 (1H, d, J=12 Hz), 3.73 (1H, d, J=12 Hz), 5.38 (2H, s), 6.95 (1H, d, J=9 Hz), 7.03 (2H, d, J=9 Hz), 7.09 (1H, d, J=1 Hz), 7.27 (2H, d, J=9 Hz), 7.3-7.4 (3H, m), 7.6-7.8 (5H, m), 7.93 (1H, d, J=8 Hz), 8.27 (1H, d, J=9 Hz), 10.94 (1H, s)

(6) 5-[4-[1-(4-Chlorobenzyl)-1H-imidazol-2-yl]phenyl]-1H-naphtho[1,2-b][1,4]diazepine-2,4(3H,5H)-dione hydrochloride By using 5-[4-[1-(4-chlorobenzyl)-1H-imidazol-2-yl]phenyl]-1H-naphtho[1,2-b][1,4]diazepine-2,4(3H,5H)-dione (36 mg, 0.073 mmol) obtained above, the title compound (37 mg, yield 96%) was obtained as slightly brown powder in the same manner as that of Example 22, (6).

$^1$H NMR (DMSO-d$_6$, 400 MHz) δ: 3.18 (1H, d, J=12 Hz), 3.76 (1H, d, J=12 Hz), 5.46 (2H, s), 6.93 (1H, d, J=9 Hz), 7.12 (2H, d, J=8 Hz), 7.40 (4H, d, J=8 Hz), 7.5-7.8 (71H, m), 7.95 (1H, d, J=8 Hz), 8.29 (1H, d, J=9 Hz), 10.97 (1H, s)

Example 24

5-[4 [1-(2-Methoxybenzyl)-1H-imidazol-2-yl]phenyl]-1H-naphtho[1,2-b][1,4]diazepine-2,4(3H,5H)-dione By using ethyl 3-[[2-[[4 [1-(2-methoxybenzyl)-1H-imidazol-2-yl]phenyl]amino]naphthalen-1-yl]amino]-3-oxopropionate (255 mg, 0.48 mmol) obtained by using 2-(4-nitrophenyl)-1H-imidazole [Heterocycles, 76, 507 (2008)], and 2-methoxybenzyl chloride in the same manner as that of Example 23, (1), (2), (3), and (4), the title compound (4 mg, yield 2%) was obtained as pale brown powder in the same manner as that of Example 3, (6).

$^1$H NMR (CDCl$_3$, 400 MHz) δ: 3.61 (2H, s), 3.80 (3H, s), 5.22 (2H, s), 6.8-6.9 (4H, m), 6.98 (1H, s), 6.99 (1H, d, J=9 Hz), 7.18 (1H, s), 7.2-7.3 (2H, m), 7.6-7.7 (5H, m), 7.86 (1H, d, J=8 Hz), 8.08 (1H, d, J=9 Hz), 8.68 (1H, s)

Example 25

5-[4 [1-(3-Methoxyphenethyl)-1H-imidazol-2-yl]phenyl]-1H-naphtho[1,2-b][1,4]diazepine-2,4(3H,5H)-dione By using ethyl 3-oxo-3-[2-[4-[1-(3-methoxyphenethyl)-1H-imidazol-2-yl)phenylamino]naphthalen-1-ylamino]propionate (80 mg, 0.15 mmol) obtained by using 2-(4-nitrophenyl)-1H-imidazole [Heterocycles, 76, 507 (2008)], and 1-(2-bromoethyl)-3-methoxybenzene in the same manner as that of Example 22, (1), (2), (3), and (4), the title compound (25 mg, yield 33%) was obtained as grayish white powder in the same manner as that of Example 3, (6).

$^1$H NMR (CDCl$_3$, 400 MHz) δ: 2.98 (2H, t, J=7 Hz), 3.62 (2H, s), 3.71 (3H, s), 4.25 (2H, t, J=7 Hz), 6.47 (1H, s), 6.58 (1H, d, J=7 Hz), 6.74 (1H, d, J=8 Hz), 6.98 (1H, s), 6.99 (1H, d, J=7 Hz), 7.1-7.2 (2H, m), 7.28 (2H, d, J=8 Hz), 7.38 (2H, d, J=8 Hz), 7.60 (1H, d, J=8 Hz), 7.61 (1H, t, J=7 Hz), 7.70 (1H, t, J=8 Hz), 7.87 (1H, d, J=8 Hz), 8.10 (1H, d, J=8 Hz), 8.73 (1H, s)

Example 26

5-[4-[1-(3-Methoxyphenethyl)-1H-imidazol-2-yl]phenyl]-1H-naphtho[1,2-b][1,4]diazepine-2,4(3H,5H)-dione hydrochloride By using 5-[4-[1-(3-methoxyphenethyl)-1H-imidazol-2-yl]phenyl]-1H-naphtho[1,2-b][1,4]diazepine-2,4(3H,5H)-dione (25 mg, 0.05 mmol) obtained in Example 25, the title compound (23 mg, yield 86%) was obtained as brown powder in the same manner as that of Example 22, (6).

$^1$H NMR (DMSO-d$_6$, 400 MHz) δ: 3.03 (2H, t, J=7 Hz), 3.20 (1H, d, J=12 Hz), 3.63 (3H, s), 3.79 (1H, d, J=12 Hz), 4.43 (2H, t, J=7 Hz), 6.53 (1H, d, J=7 Hz), 6.54 (1H, s), 6.75 (1H, d, J=9 Hz), 6.98 (1H, d, J=9 Hz), 7.11 (1H, t, J=8 Hz), 7.4-7.5 (4H, m), 7.64 (1H, t, J=8 Hz), 7.71 (1H, t, J=8 Hz), 7.77 (1H, d, J=9 Hz), 7.82 (1H, s), 7.96 (1H, d, J=8 Hz), 8.30 (1H, d, J=9 Hz), 11.01 (1H, s)

Example 27

5-[4-[1-(3-Hydroxyphenethyl)-1H-imidazol-2-yl]phenyl]-1H-naphtho[1,2-b][1,4]diazepine-2,4(3H,5H)-dione By using 5-[4-[1-(3-methoxyphenethyl)-1H-imidazol-2-yl]phenyl]-1H-naphtho[1,2-b][1,4]diazepine-2,4(3H,5H)-dione (12 mg, 0.024 mmol) obtained in Example 26, the title compound was obtained as white powder in the same manner as that of Example 2 (6 mg, yield 50%).

$^1$H NMR (CDCl$_3$, 400 MHz) δ: 2.7-2.9 (2H, m), 3.49 (1H, br s), 3.65 (2H, s), 4.1-4.3 (2H, m), 6.08 (1H, s), 6.43 (1H, d, J=7 Hz), 6.67 (1H, dd, J=2, 7 Hz), 7.0-7.1 (3H, m), 7.12 (1H, d, J=1 Hz), 7.2-7.3 (2H, m), 7.38 (2H, d, J=8 Hz), 7.6-7.7 (2H, m), 7.72 (1H, t, J=7 Hz), 7.88 (1H, d, J=8 Hz), 8.11 (1H, d, J=8 Hz), 8.61 (1H, s)

Example 28

5-[4-[1-(2,4,6-Trimethylbenzyl)-1H-imidazol-2-yl]phenyl]-1H-naphtho[1,2-b][1,4]diazepine-2,4(3H,5H)-dione hydrochloride (1) 5-[4-[1-(2,4,6-Trimethylbenzyl)-1H-imidazol-2-yl]phenyl]-1H-naphtho[1,2-b][1,4]diazepine-2,4(3H,5H)-dione By using ethyl 3-[[2-[[4-[1-(2,4,6-trimethylbenzyl)-1H-imidazol-2-yl]phenyl]amino]naphthalen-1-yl]amino]-3-oxopropionate (40 mg, 0.073 mmol) obtained by using 2-(4-nitrophenyl)-1H-imidazole [Heterocycles, 76, 507 (2008)], and 2,4,6-trimethylbenzyl chloride in the same manner as that of Example 23, (1), (2), (3), and (4), the title compound (16 mg, yield 44%) was obtained as pale brown powder in the same manner as that of Example 3, (6).

$^1$H NMR (CDCl$_3$, 400 MHz) δ: 2.15 (6H, s), 2.29 (3H, s), 3.64 (2H, s), 5.16 (2H, s), 6.48 (1H, s), 6.89 (2H, s), 7.0-7.1 (2H, m), 7.40 (2H, d, J=8 Hz), 7.6-7.7 (2H, m), 7.71 (1H, t, J=8 Hz), 7.78 (2H, d, J=8 Hz), 7.88 (1H, d, J=8 Hz), 8.06 (1H, d, J=8 Hz), 8.17 (1H, s)

(2) 5-[4-[1-(2,4,6-Trimethylbenzyl)-1H-imidazol-2-yl]phenyl]-1H-naphtho[1,2-b][1,4]diazepine-2,4(3H,5H)-dione hydrochloride By using 5-[4-[1-(2,4,6-trimethylbenzyl)-1H-imidazol-2-yl]phenyl]-1H-naphtho[1,2-b][1,4]diazepine-2,4(3H,5H)-dione (16 mg, 0.032 mmol) obtained above, the title compound (17 mg, yield 100%) was obtained as slightly brown crystals in the same manner as that of Example 22, (6).

$^1$H NMR (DMSO-d$_6$, 400 MHz) δ: 2.10 (6H, s), 2.23 (3H, s), 3.21 (1H, d, J=12 Hz), 3.79 (1H, d, J=12 Hz), 5.3-5.4 (2H, m), 6.93 (2H, s), 7.01 (1H, d, J=9 Hz), 7.08 (1H, s), 7.53 (2H, d, J=8 Hz), 7.63 (1H, t, J=7 Hz), 7.70 (2H, t, J=7 Hz), 7.77 (1H, d, J=9 Hz), 7.91 (2H, d, J=8 Hz), 7.96 (1H, d, J=8 Hz), 8.30 (1H, d, J=9 Hz), 10.99 (1H, s)

Example 29

4-[3-[5-[2-(Pyridin-2-yl)ethyl]-1H-tetrazol-1-yl]phenyl]-benzo[f]quinoxaline-2,3 (1H,4H)-dione hydrochloride (1) N-[3-[(1-Nitronaphthalen-2-yl)amino]phenyl]-3-(pyridin-2-yl)propanamide N-(1-Nitronaphthalen-2-yl)-benzene-1,3-diamine (300 mg, 0.790 mmol), 3-(pyridin-2-yl)propionic acid (131 mg, 0.869 mmol), and 1-ethyl-3-(3-dimethylaminopropyl)carbodiimide hydrochloride (197 mg, 1.027 mmol) were mixed with acetonitrile (8 mL), and the mixture was stirred at room temperature for 2 days under a nitrogen atmosphere. The solvent was evaporated under reduced pressure, saturated aqueous citric acid was added to the residue, and the resulting mixture was extracted with chloroform. The organic layer was washed with saturated brine, and dried over anhydrous sodium sulfate. The solvent was evaporated under reduced pressure, and the residue was purified by silica gel chromatography (methanol/chloroform=1/100) to obtain the title compound (325 mg, yield 99%) as reddish brown oil.

$^1$H NMR (CDCl$_3$, 400 MHz) δ: 2.88 (2H, t, J=7 Hz), 3.23 (2H, t, J=7 Hz), 6.97 (1H, d, J=8 Hz), 7.2-7.4 (6H, m), 7.6-7.8 (5H, m), 8.5-8.6 (2H, m), 9.49 (1H, s), 9.80 (1H, s)

(2) 1-Nitro-N-[3-[5-[2-(pyridin-2-yl)ethyl]-1H-tetrazol-1-yl]phenyl]naphthalen-2-amine By using N-[3-[(1-nitronaphthalen-2-yl)amino]phenyl]-3-(pyridin-2-yl)propanamide (325 mg, 0.790 mol) obtained above, the title compound was obtained as reddish brown oil in the same manner as that of Example 3, (3).

$^1$H NMR (CDCl$_3$, 400 MHz) δ: 3.41 (4H, s), 7.0-7.1 (1H, m), 7.13 (1H, d, J=8 Hz), 7.2-7.3 (2H, m), 7.4-7.5 (3H, m), 7.55 (2H, dd, J=8 Hz), 7.66 (1H, t, J=8 Hz), 7.76 (1H, d, J=8 Hz), 7.82 (1H, d, J=9 Hz), 8.38 (2H, d, J=9 Hz), 9.05 (1H, s)

(3) N-[3-[5-[2-(Pyridin-2-yl)ethyl]-1H-tetrazol-1-yl]phenyl]naphthalene 1,2-diamine By using 1-nitro-N-[3-[5-[2-(pyridin-2-yl)ethyl]-1H-tetrazol-1-yl]phenyl]naphthalen-2-amine (351 mg, 0.803 mol) obtained above, the title compound was obtained as a reddish brown amorphous substance in the same manner as that of Example 3, (4).

$^1$H NMR (CDCl$_3$, 400 MHz) δ: 3.39 (4H, s), 3.48 (2H, s), 5.82 (1H, s), 6.63 (1H, s), 6.77 (1H, d, J=7 Hz), 6.84 (1H, d, J=8 Hz), 7.16 (1H, t, J=6 Hz), 7.2-7.3 (4H, m), 7.4-7.5 (2H, m), 7.65 (1H, t, J=8 Hz), 7.7-7.8 (2H, m), 8.45 (1H, s)

(4) Ethyl 2-oxo-2-[[2-[[3-[5-[2-(pyridin-2-yl)ethyl]-1H-tetrazol-1-yl]phenyl]amino]naphthalen-1-yl]amino]acetate N-[3-[5-[2-(Pyridin-2-yl)ethyl]-1H-tetrazol-1-yl]phenyl]naphthalene-1,2-diamine (106.7 mg, 0.261 mol) obtained above, and sodium carbonate (27.66 mg, 0.271 mmol) were dissolved in dichloromethane (2 mL) and water (0.5 mL), and ethyl chloroglyoxylate (32 μL, 0.288 mmol) was added dropwise to the solution with stirring under ice cooling. This reaction mixture was stirred overnight at room temperature. To the reaction mixture, saturated aqueous sodium hydrogencarbonate was added, the resulting mixture was extracted with chloroform, and the organic layer was washed with saturated brine, and dried over anhydrous sodium sulfate. The solvent was evaporated under reduced pressure, and the residue was purified by silica gel chromatography (ethyl acetate/hexane=1/1) to obtain the title compound (128 mg, yield 96%) as pale yellow oil.

(5) 4-[3-[5-[2-(Pyridin-2-yl)ethyl]-1H-tetrazol-1-yl]phenyl]-benzo[f]quinoxaline-2,3(1H,4H)-dione By using ethyl 2-oxo-2-[[2-[[3-[5-[2-(pyridin-2-yl)ethyl]-1H-tetrazol-1-yl]phenyl]amino]naphthalen-1-yl]amino]acetate (128 mg, 0.252 mol) obtained above, the title compound (32.4 mg, yield 28%) was obtained as gray solid in the same manner as that of Example 3, (6).

(6) 4-[3-[5-[2-(Pyridin-2-yl)ethyl]-1H-tetrazol-1-yl]phenyl]-benzo[f]quinoxaline-2,3(1H,4H)-dione hydrochloride By using 4-[3-[5-[2-(pyridin-2-yl)ethyl]-1H-tetrazol-1-yl]phenyl]-benzo[f]quinoxaline-2,3(1H,4H)-dione (32.4 mg, 0.0702 mmol) obtained above, the title compound (31.4 mg) was obtained as slightly brown crystals in the same manner as that of Example 3, (7).

$^1$H NMR (DMSO-d$_6$, 400 MHz) δ: 3.4-3.5 (4H, m), 6.72 (1H, d, J=9 Hz), 7.4-7.8 (6H, m), 7.9-8.0 (4H, m), 8.0-8.2 (1H, m), 8.62 (1H, d, J=2 Hz), 8.69 (1H, d, J=8 Hz), 12.39 (1H, s)

Example 30

5-[4-[5-[2-(6-Methylpyridin-2-ylethyl)-1H-tetrazol-1-yl]-phenyl]-1H-naphtho[1,2-b][1,4]diazepine-2,4(3H,5H)-dione hydrochloride (1) 5-[4-[5-[2-(6-Methylpyridin-2-yl)ethyl]-1H-tetrazol 1-yl]-phenyl]-1H-naphtho[1,2-b][1,4]diazepine-2,4(3H,5H)-dione By using ethyl 3-[[2-[[4-[5-[2-(6-methylpyridin-2-yl)ethyl]-1H-tetrazol-2-yl]phenyl]amino]naphthalen-1-yl]amino]-3-oxopropionate (105 mg, 0.197 mmol) obtained by using N$^1$-(1-nitronaphthalen-2-yl)benzene-1,4-diamine obtained in Example 3, (1), and 3-(6-methylpyridin-2-yl)propionic acid in the same manner as that of Example 3, (2), (3), (4), and (5), the title compound (72 mg, yield 74%) was obtained as pale yellow oil in the same manner as that of Example 3, (6).

$^1$H NMR (DMSO-d$_6$, 400 MHz): δ: 2.32 (3H, s), 3.2-3.3 (3H, m), 3.3-3.4 (2H, m), 3.78 (1H, d, J=12 Hz), 7.02 (2H, d, J=8 Hz), 7.05 (1H, d, J=10 Hz), 7.5-7.6 (3H, m), 7.62 (1H, t, J=7 Hz), 7.7-7.8 (4H, m), 7.95 (1H, d, J=8 Hz), 8.30 (1H, d, J=11 Hz), 10.98 (1H, s)

(2) 5-[4-[5-[2-(6-Methylpyridin-2-ylethyl)-1H-tetrazol-1-yl]-phenyl]-1H-naphtho[1,2-b][1,4]diazepine-2,4(3H,5H)-dione hydrochloride By using 5-[4-[5-[2-(6-methylpyridin-2-yl)ethyl]-1H-tetrazol-1-yl]-phenyl]-1H-naphtho[1,2-b][1,4]diazepine-2,4 (3H,5H)-dione (72 mg, 0.146 mmol) obtained above, the title compound (65 mg, yield 85%) was obtained as a slightly brown amorphous substance in the same manner as that of Example 3, (7).

$^1$H NMR (DMSO-d$_6$, 400 MHz) δ: 2.68 (3H, s), 3.21 (1H, d, J=12 Hz), 3.51 (4H, t, J=6 Hz), 3.79 (1H, d, J=12 Hz), 7.06 (1H, d, J=8 Hz), 7.53 (2H, d, J=8 Hz), 7.6-7.8 (7H, in), 7.96 (1H, d, J=8 Hz), 8.2-8.3 (2H, m), 10.99 (1H, s)

Example 31

5-[4-[(2-(3-Fluorophenyl)ethyl)-1H-imidazol-1-yl] phenyl]-1H-naphtho[1,2-b][1,4]diazepine-2,4(3H, 5H)-dione hydrochloride (1) 5-[4-[(2-(3-Fluorophenyl)ethyl)-1H-imidazol-1-yl]phenyl]-1H-naphtho[1,2-b][1,4]diazepine-2,4(3H, 5H)-dione By using ethyl 3-[[2-[[4-[2-(3-fluorophenylethyl)-1H-imidazol-1-yl]phenyl]amino]naphthalen-1-yl]amino]-3- oxopropionate (34 mg, 0.0644 mmol) obtained by using N¹-(1-nitronaphthalen-2-yl)benzene-1,4-diamine obtained in Example 3, (1), and 3-(2-fluorophenyl)propionic acid in the same manner as that of Example 3, (2), (4), (5), Example 21, (1), (2), and (3), the title compound (14 mg, yield 44%) was obtained as pale yellow oil in the same manner as that of Example 3, (6).

$^1$H NMR (DMSO-$d_6$, 400 MHz) δ: 2.95 (4H, s), 3.18 (1H, d, J=12 Hz), 3.74 (1H, d, J=12 Hz), 6.9-7.1 (5H, m), 7.25 (1H, dt, J=7 Hz, 8 Hz), 7.3-7.5 (5H, m), 7.6-7.8 (3H, m), 7.94 (1H, d, J=7 Hz), 8.28 (1H, d, J=9 Hz), 10.95 (1H, s)

(2) 5-[4-[(2-(3-Fluorophenyl)ethyl)-1H-imidazol-1-yl]phenyl]-1H-naphtho[1,2-b][1,4]diazepine-2,4(3H,5H)-dione hydrochloride By using 5-[4-[(2-(3-fluorophenyl)ethyl)-1H-imidazol-1-yl]phenyl]-1H-naphtho[1,2-b][1,4]diazepine-2,4(3H,5H)-dione (14 mg, 0.0285 mmol) obtained above, the title compound (9 mg, yield 65%) was obtained as a slightly brown amorphous substance in the same manner as that of Example 3, (7).

$^1$H NMR (DMSO-$d_6$, 400 MHz) δ: 2.96 (2H, t, J=7 Hz), 3.2-3.3 (3H, m), 3.78 (1H, d, J=12 Hz), 6.85 (1H, d, J=7 Hz), 6.91 (1H, d, J=10 Hz), 7.0-7.1 (2H, m), 7.28 (1H, dt, J=6 Hz, 7 Hz), 7.48 (2H, d, J=8 Hz), 7.54 (2H, d, J=8 Hz), 7.6-7.8 (3H, m), 7.82 (1H, s), 7.9-8.0 (2H, m), 8.30 (1H, d, J=9 Hz), 10.99 (1H, s)

Example 32

5-[4-[(2-(2-Methoxyphenyl)ethyl)-1H-imidazol-1-yl]phenyl]-1H-naphtho[1,2-b][1,4]diazepine-2,4(3H,5H)-dione hydrochloride

(1) 5-[4-[(2-(2-Methoxyphenyl)ethyl)-1H-imidazol-1-yl]phenyl]-1H-naphtho[1,2-b][1,4]diazepine-2,4(3H,5H)-dione By using ethyl 3-[[2-[[4-[2-(2-methoxyphenylethyl)-1H-imidazol-1-yl]phenyl]amino]naphthalen-1-yl]amino]-3-oxopropionate (99 mg, 0.180 mmol) obtained by using N¹-(1-nitronaphthalen-2-yl)benzene-1,4-diamine obtained in Example 3, (1), and 3-(2-methoxyphenyl)propionic acid in the same manner as that of Example 3, (2), (4), (5), Example 21, (1), (2), and (3), the title compound (27 mg, yield 31%) was obtained as colorless oil in the same manner as that of Example 3, (6).

$^1$H NMR (DMSO-$d_6$, 400 MHz) δ: 2.85 (4H, s), 3.18 (1H, d, J=12 Hz), 3.67 (3H, s), 3.75 (1H, d, J=12 Hz), 6.79 (1H, t, J=7 Hz), 6.88 (1H, d, J=8 Hz), 6.9-7.0 (2H, m), 7.02 (1H, d, J=9 Hz), 7.15 (1H, t, J=8 Hz), 7.28 (1H, d, J=1 Hz), 7.35 (4H, s), 7.61 (1H, t, J=8 Hz), 7.68 (1H, t, J=7 Hz), 7.74 (1H, d, J=9 Hz), 7.94 (1H, d, J=8 Hz), 8.28 (1H, d, J=8 Hz), 10.96 (1H, s)

(2) 5-[4-[(2-(2-Methoxyphenyl)ethyl)-1H-imidazol-1-yl]phenyl]-1H-naphtho[1,2-b][1,4]diazepine-2,4(3H,5H)-dione hydrochloride By using 5-[4-[(2-(2-methoxyphenyl)ethyl)-1H-imidazol-1-yl]phenyl]-1H-naphtho[1,2-b][1,4]diazepine-2,4(3H,5H)-dione (24 mg, 0.0481 mmol) obtained above, the title compound (15 mg, yield 57%) was obtained as a white amorphous substance in the same manner as that of Example 3, (7).

$^1$H NMR (DMSO-$d_6$, 400 MHz) δ: 2.89 (2H, t, J=7 Hz), 3.15 (2H, t, J=7 Hz), 3.20 (1H, d, J=12 Hz), 3.59 (3H, s), 3.78 (1H, d, J=12 Hz), 6.81 (1H, t, J=7 Hz), 6.8-6.9 (2H, m), 6.99 (1H, d, J=9 Hz), 7.20 (1H, t, J=8 Hz), 7.39 (2H, d, J=8 Hz), 7.46 (2H, d, J=8 Hz), 7.63 (1H, d, J=8 Hz), 7.70 (1H, t, J=8 Hz), 7.76 (1H, d, J=9 Hz), 7.82 (1H, d, J=2 Hz), 7.87 (1H, d, J=2 Hz), 7.95 (1H, d, J=8 Hz), 8.30 (1H, d, J=8 Hz), 10.99 (1H, s)

Example 33

5-[4-[(2-(4-Fluorophenyl)ethyl)-1H-imidazol-1-yl]phenyl]-1H-naphtho[1,2-b][1,4]diazepine-2,4(3H,5H)-dione hydrochloride

(1) 5-[4-[(2-(4-Fluorophenyl)ethyl)-1H-imidazol-1-yl]phenyl]-1H-naphtho[1,2-b][1,4]diazepine-2,4(3H,5H)-dione By using ethyl 3-[[2-[[4-[2-(4-fluorophenylethyl)-1H-imidazol-1-yl]phenyl]amino]naphthalen-1-yl]amino]-3-oxopropionate (141 mg, 0.263 mmol) obtained by using N¹-(1-nitronaphthalen-2-yl)benzene-1,4-diamine obtained in Example 3, (1), and 3-(4-fluorophenyl)propionic acid in the same manner as that of Example 3, (2), (4), (5), Example 21, (1), (2), and (3), the title compound (39 mg, yield 22%) was obtained as pale yellow oil in the same manner as that of Example 3, (6).

$^1$H NMR (DMSO-$d_6$, 400 MHz) δ: 2.91 (4H, s), 3.18 (1H, d, J=12 Hz), 3.75 (1H, d, J=12 Hz), 7.0-7.2 (6H, m), 7.3-7.4 (5H, m), 7.61 (1H, t, J=8 Hz), 7.68 (1H, t, J=8 Hz), 7.74 (1H, d, J=9 z), 7.94 (1H, d, J=8 Hz), 8.28 (1H, d, J=9 Hz), 10.96 (1H, s)

(2) 5-[4-[(2-(4-Fluorophenyl)ethyl)-1H-imidazol-1-yl]phenyl]-1H-naphtho[1,2-b][1,4]diazepine-2,4(3H,5H)-dione hydrochloride By using 5-[4-[(2-(4-fluorophenyl)ethyl)-1H-imidazol-1-yl]phenyl]-1H-naphtho[1,2-b][1,4]diazepine-2,4(3H,5H)-dione (39 mg, 0.0784 mmol) obtained above, the title compound (32 mg, yield 77%) was obtained as a slightly brown amorphous substance in the same manner as that of Example 3, (7).

$^1$H NMR (DMSO-$d_6$, 400 MHz) δ: 2.93 (2H, t, J=7 Hz), 3.1-3.2 (3H, m), 3.78 (1H, d, J=12 Hz), 7.01 (1H, d, J=7 Hz), 7.06 (4H, d, J=7 Hz), 7.48 (2H, d, J=9 Hz), 7.55 (2H, d, J=9 Hz), 7.63 (1H, t, J=7 Hz), 7.70 (1H, t, J=9 Hz), 7.76 (1H, d, J=9 Hz), 7.82 (1H, d, J=2 Hz), 7.92 (1H, d, J=2 Hz), 7.96 (1H, d, J=8 Hz), 8.30 (1H, d, J=8 Hz), 10.98 (1H, s)

Example 34

5-[4-[(2-(2-Fluorophenyl)ethyl)-1H-imidazol-1-yl]phenyl]-1H-naphtho[1,2-b][1,4]diazepine-2,4(3H,5H)-dione hydrochloride

(1) 5-[4-[(2-(2-Fluorophenyl)ethyl)-1H-imidazol-1-yl]phenyl]-1H-naphtho[1,2-b][1,4]diazepine-2,4(3H,5H)-dione By using ethyl 3-[[2-[[4-[2-(2-fluorophenylethyl)-1H-imidazol-1-yl]phenyl]amino]naphthalen-1-yl]amino]-3-oxopropionate (147 mg, 0.275 mmol) obtained by using N¹-(1-nitronaphthalen-2-yl)benzene-1,4-diamine obtained in Example 3, (1), and 3-(2-fluorophenyl)propionic acid in the same manner as that of Example 3, (2), (4), (5), Example 21, (1), (2), and (3), the title compound (59 mg, yield 44%) was obtained as a pale yellow amorphous substance in the same manner as that of Example 3, (6).

$^1$H NMR (DMSO-$d_6$, 400 MHz) δ: 2.93 (4H, s), 3.18 (1H, d, J=12 Hz), 3.75 (1H, d, J=12 Hz), 7.0-7.3 (6H, m), 7.36 (3H, d, J=9 Hz), 7.42 (2H, d, J=9 Hz), 7.61 (1H, t, J=8 Hz), 7.68 (1H, t, J=8 Hz), 7.75 (1H, d, J=9 Hz), 7.95 (1H, d, J=8 Hz), 8.28 (1H, d, J=8 Hz), 10.94 (1H, s)

(2) 5-[4-[(2-(2-Fluorophenyl)ethyl)-1H-imidazol-1-yl]phenyl]-1H-naphtho[1,2-b][1,4]diazepine-2,4(3H,5H)-dione hydrochloride By using 5-[4-[(2-(2-fluorophenyl)ethyl)-1H-imidazol-1-yl]phenyl]-1H-naphtho[1,2-b][1,4]diazepine-2,4(3H,5H)-dione (59 mg, 0.121 mmol) obtained above, the title compound (43 mg, yield 68%) was obtained as a slightly brown amorphous substance in the same manner as that of Example 3, (7).

$^1$H NMR (DMSO-$d_6$, 400 MHz) δ: 2.95 (2H, t, J=7 Hz), 3.1-3.2 (3H, m), 3.78 (1H, d, J=12 Hz), 6.99 (1H, d, J=9 Hz), 7.0-7.1 (3H, m), 7.2-7.3 (1H, m), 7.46 (2H, d, J=9 Hz), 7.50 (2H, d, J=9 Hz), 7.63 (1H, t, J=8 Hz), 7.70 (1H, t, J=8 Hz), 7.7-7.8 (2H, m), 7.90 (1H, s), 7.97 (1H, d, J=8 Hz), 8.30 (1H, d, J=9 Hz), 10.97 (1H, s)

Example 35

5-[4-[1-[2-(Trifluoromethyl)benzyl]-1H-imidazol-2-yl]phenyl]-1H-naphtho[1,2-b][1,4]diazepine-2,4(3H, 5H)-dione hydrochloride (1) 5-[4-[1-[2-(Trifluoromethyl)benzyl]-1H-imidazol-2-yl]phenyl]-1H-naphtho[1,2-b][1,4]diazepine-2,4(3H,5H)-dione By using ethyl 3-[[2-[[4-[1-[2-(trifluoromethyl)benzyl]-1H-imidazol-2-yl]phenyl]amino]naphthalen-1-yl]amino]-3-oxopropionate (260 mg, 0.454 mmol) obtained by using 2-(4-nitrophenyl)-11H-imidazole [Heterocycles, 76, 507 (2008)], and 2-(trifluoromethyl)benzyl bromide in the same manner as that of Example 23, (1), (2), (3), and (4), the title compound (91 mg, yield 38%) was obtained as pale yellow crystals in the same manner as that of Example 3, (6).

$^1$H NMR (DMSO-$d_6$, 400 MHz) δ: 3.14 (1H, d, J=12 Hz), 3.70 (1H, d, J=12 Hz), 5.56 (2H, s), 6.75 (1H, d, J=7 Hz), 6.86 (1H, d, J=9 Hz), 7.15 (1H, d, J=1 Hz), 7.23 (2H, d, J=9 Hz), 7.37 (1H, d, J=1 Hz), 7.5-7.7 (7H, m), 7.78 (1H, d, J=8 Hz), 7.93 (1H, d, J=8 Hz), 8.25 (1H, d, J=8 Hz), 10.91 (1H, s)

(2) 5-[4-[1-[2-(Trifluoromethyl)benzyl]-1H-imidazol-2-yl]phenyl]-1H-naphtho[1,2-b][1,4]diazepine-2,4(3H,5H)-dione hydrochloride By using 5-[4-[1-[2-(trifluoromethyl)benzyl]-1H-imidazol-2-yl]phenyl]-1H-naphtho[1,2-b][1,4]diazepine-2,4(3H,5H)-dione (91 mg, 0.173 mmol) obtained above, the title compound (83 mg, yield 85%) was obtained as a pale yellow amorphous substance in the same manner as that of Example 3, (7).

$^1$H NMR (DMSO-$d_6$, 400 MHz) δ: 3.17 (1H, d, J=12 Hz), 3.74 (1H, d, J=12 Hz), 5.68 (2H, s), 6.77 (1H, d, J=9 Hz), 7.13 (1H, d, J=8 Hz), 7.43 (2H, d, J=9 Hz), 7.6-7.8 (7H, m), 7.8-8.0 (4H, m), 8.28 (1H, d, J=8 Hz), 10.95 (1H, s)

Example 36

5-[4-[2-[4-(Trifluoromethyl)phenylethyl]-1H-imidazol-1-yl]phenyl]-1H-naphtho[1,2-b][1,4]diazepine-2, 4(3H,5H)-dione hydrochloride (1) 5-[4-[2-[4-(Trifluoromethyl)phenylethyl]-1H-imidazol-1-yl]phenyl]-1H-naphtho[1,2-b][1,4]diazepine-2,4(3H,5H)-dione By using ethyl 3-[[2-[[4-[2-[4-(trifluoromethyl)phenylethyl]-1H-imidazol-1-yl]phenyl]amino]naphthalen-1-yl]amino]-3-oxopropionate (253 mg, 0.431 mmol) obtained by using N$^1$-(1-nitronaphthalen-2-yl)benzene-1,4-diamine obtained in Example 3, (1), and 3-(4-(trifluoromethyl)phenyl)propionic acid in the same manner as that of Example 3, (2), (4), (5), Example 21, (1), (2), and (3), the title compound (92 mg, yield 40%) was obtained as colorless oil in the same manner as that of Example 3, (6).

$^1$H NMR (DMSO-$d_6$, 400 MHz) δ: 2.9-3.1 (4H, m), 3.19 (1H, d, J=12 Hz), 3.75 (1H, d, J=12 Hz), 6.99 (1H, d, J=2 Hz), 7.02 (1H, d, J=9 Hz), 7.2-7.3 (7H, m), 7.56 (2H, d, J=8 Hz), 7.61 (1H, t, J=8 Hz), 7.68 (1H, dt, J=2 Hz, 8 Hz), 7.74 (1H, d, J=9 Hz), 7.93 (1H, d, J=8 Hz), 8.28 (1H, d, J=9 Hz)

(2) 5-[4-[2-[4-(Trifluoromethyl)phenylethyl]-1H-imidazol-1-yl]phenyl]-1H-naphtho[1,2-b][1,4]diazepine-2,4(3H,5H)-dione hydrochloride By using 5-[4-[1-[4-(trifluoromethyl)phenylethyl]-1H-imidazol-1-yl]phenyl]-1H-naphtho[1,2-b][1,4]diazepine-2, 4(3H,5H)-dione (23 mg, 0.0421 mmol) obtained above, the title compound (14 mg, yield 57%) was obtained as a white amorphous substance in the same manner as that of Example 3, (7).

$^1$H NMR (DMSO-$d_6$, 400 MHz) δ: 3.04 (2H, t, J=7 Hz), 3.2-3.3 (3H, m), 3.78 (1H, d, J=12 Hz), 7.01 (1H, d, J=9 Hz), 7.26 (2H, d, J=8 Hz), 7.45 (2H, d, J=9 Hz), 7.52 (2H, d, J=9 Hz), 7.6-7.8 (6H, m), 7.89 (1H, s), 7.95 (1H, d, J=8 Hz), 8.30 (1H, d, J=8 Hz), 10.97 (1H, s)

Example 37

5-[4-[2-(2,6-Dimethylphenylethyl)-1H-imidazol-1-yl]phenyl]-1H-naphtho[1,2-b][1,4]diazepine-2,4(3H, 5H)-dione hydrochloride (1) 5-[4-[2-(2,6-Dimethylphenylethyl) 1H-imidazol-1-yl]phenyl]-1H-naphtho[1,2-b][1,4]diazepine-2,4 (3H,5H)-dione By using ethyl 3-[[2-[[4-[2-(2,6-dimethylphenylethyl)-1H-imidazol-1-yl]phenyl]amino]naphthalen-1-yl]amino]-3-oxopropionate (128 mg, 0.233 mmol) obtained by using N$^1$-(1-nitronaphthalen-2-yl)benzene-1,4-diamine obtained in Example 3, (1), and 3-(2,6-dimethylphenyl)propionic acid in the same manner as that of Example 3, (2), (4), (5), Example 21, (1), (2), and (3), the title compound (48 mg, yield 41%) was obtained as colorless oil in the same manner as that of Example 3, (6).

$^1$H NMR (DMSO-$d_6$, 400 MHz) δ: 2.07 (6H, s), 2.79 (4H, s), 3.18 (1H, d, J=12 Hz), 3.75 (1H, d, J=12 Hz), 6.9-7.0 (3H, m), 7.0-7.1 (2H, m), 7.34 (3H, d, J=9 Hz), 7.40 (2H, d, J=9 Hz), 7.62 (1H, t, J=7 Hz), 7.69 (1H, t, J=8 Hz), 7.79 (1H, d, J=9 Hz), 7.97 (1H, d, J=7 Hz), 8.28 (1H, d, J=8 Hz), 10.95 (1H, s)

(2) 5-[4-[2-(2,6-Dimethylphenylethyl)-1H-imidazol-1-yl]phenyl]-1H-naphtho[1,2-b][1,4]diazepine-2,4(3H,5H)-dione hydrochloride By using 5-[4-[2-(2,6-dimethylphenylethyl)-1H-imidazol-1-yl]phenyl]-1H-naphtho[1,2-b][1,4]diazepine-2,4(3H,5H)-dione (48 mg, 0.0956 mmol) obtained above, the title compound (40 mg, yield 78%) was obtained as a slightly brown amorphous substance in the same manner as that of Example 3, (7).

$^1$H NMR (DMSO-d$_6$, 400 MHz) δ: 2.03 (6H, s), 2.84 (2H, t, J=8 Hz), 3.03 (2H, t, J=8 Hz), 3.20 (1H, d, J=12 Hz), 3.78 (1H, d, J=12 Hz), 6.9-7.0 (4H, m), 7.47 (2H, d, J=7 Hz), 7.6-7.8 (4H, m), 7.82 (1H, d, J=9 Hz), 7.88 (1H, s), 7.9-8.0 (2H, m), 8.30 (1H, d, J=8 Hz), 10.97 (1H, s)

Example 38

5-[4-[2-[3-(Trifluoromethyl)phenylethyl]-1H-imidazol-1-yl]phenyl]-1H-naphtho[1,2-b][1,4]diazepine-2,4(3H,5H)-dione hydrochloride

(1) 5-[4-[2-[3-(Trifluoromethyl)phenylethyl]-1H-imidazol-1-yl]phenyl]-1H-naphtho[1,2-b][1,4]diazepine-2,4(3H,5H)-dione By using ethyl 3-[[2-[[4-[2-[3-(trifluoromethyl)phenylethyl]-1H-imidazol-1-yl]phenyl]amino]naphthalen-1-yl]amino]-3-oxopropionate (420 mg, 0.717 mmol) obtained by using N$^1$-(1-nitronaphthalen-2-yl)benzene-1,4-diamine obtained in Example 3, (1), and 3-(3-(trifluoromethyl)phenyl)propionic acid in the same manner as that of Example 3, (2), (4), (5), Example 21, (1), (2), and (3), the title compound (45 mg, yield 12%) was obtained as slightly brown oil in the same manner as that of Example 3, (6).

$^1$H NMR (DMSO-d$_6$, 400 MHz): δ: 2.9-3.1 (4H, m), 3.18 (1H, d, J=12 Hz), 3.74 (1H, d, J=12 Hz), 7.0-7.1 (2H, m), 7.3-7.5 (9H, m), 7.61 (1H, t, J=7 Hz), 7.7-7.8 (2H, m), 7.93 (1H, d, J=8 Hz), 8.28 (1H, d, J=9 Hz), 10.93 (1H, s)

(2) 5-[4-[2-[3-(Trifluoromethyl)phenylethyl]-1H-imidazol-1-yl]phenyl]-1H-naphtho[1,2-b][1,4]diazepine-2,4(3H,5H)-dione hydrochloride By using 5-[4-[3-(trifluoromethyl)phenylethyl]-1H-imidazol-1-yl]phenyl]-1H-naphtho[1,2-b][1,4]diazepine-2,4(3H,5H)-dione (45 mg, 0.0834 mmol) obtained above, the title compound (42 mg, yield 88%) was obtained as a slightly brown amorphous substance in the same manner as that of Example 3, (7).

$^1$H NMR (DMSO-d$_6$, 400 MHz) δ: 3.08 (2H, t, J=7 Hz), 3.2-3.3 (3H, m), 3.78 (1H, d, J=12 Hz), 7.00 (1H, d, J=9 Hz), 7.36 (1H, d, J=8 Hz), 7.4-7.6 (7H, m), 7.6-7.8 (3H, m), 7.82 (1H, s), 7.9-8.0 (2H, m), 8.30 (1H, d, J=9 Hz), 10.97 (1H, s)

Example 39

5-[4-[5-[2-(Pyridin-2-yl)ethyl]-1H-tetrazol-1-yl]phenyl]-1H-naphtho[1,2-e][1,4]diazepin-2(3H)-one dihydrochloride 5-[4-[5-[2-(Pyridin-2-yl)ethyl]-1H-tetrazol-1-yl]phenyl]-1H-naphtho[1,2-e][1,4]diazepin-2(3H)-one (28 mg, 0.061 mmol) obtained in Example 17 was dissolved in ethyl acetate (1 mL), a 4 M solution of hydrogen chloride in ethyl acetate (100 μL) was added to the solution, and the resulting mixture was stirred at room temperature for 0.5 hour. The deposited crystals were collected by filtration, washed with ethyl acetate, and then air-dried to obtain the title compound (24 mg, yield 74%) as yellow crystals.

$^1$H NMR (DMSO-d$_6$, 400 MHz) δ: 2.5-3.5 (2H, m), 3.90 (1H, br s), 4.64 (1H, br s), 7.33 (1H, d, J=9 Hz), 7.6-7.9 (9H, m), 8.0-8.1 (1H, m), 8.22 (1H, br s), 8.40 (1H, d, J=9 Hz), 8.67 (1H, d, J=5 Hz), 10.96 (1H, s)

Example 40

5-[4-(5-Phenethyl-1H-tetrazol-1-yl)phenyl]-1H-naphtho[1,2-e][1,4]diazepin-2(3H)-one By using 5-(4-aminophenyl)-1H-naphtho[1,2-e][1,4]diazepin-2(3H)-one obtained in Example 17, (2), the title compound was obtained as a pale yellow amorphous substance in the same manner as that of Example 17, (3), (4), (5), and (6).

$^1$H NMR (DMSO-d$_6$, 400 MHz) δ: 3.04 (2H, t, J=8 Hz), 3.24 (2H, t, J=8 Hz), 3.88 (1H, br s), 4.62 (1H, br s), 7.1-7.3 (5H, m), 7.32 (1H, d, J=9 Hz), 7.59 (2H, d, J=9 Hz), 7.6-7.8 (5H, m), 8.0-8.1 (1H, m), 8.3-8.4 (1H, m), 10.92 (1H, s)

Example 41

5-[4-(2-Phenethyl-1H-imidazol-1-yl)phenyl]-1H-naphtho[1,2-e][1,4]diazepin-2(3H)-one dihydrochloride

(1) 5-[4-(2-Phenethyl-1H-imidazol 1-yl)phenyl]-1H-naphtho[1,2-e][1,4]diazepin-2(3H)-one With reference to information described in a reference [J. Am. Chem. Soc, 134, 9796 (2012)], 5-(4-Aminophenyl)-1H-naphtho[1,2-e][1,4]diazepin-2(3H)-one (50 mg, 0.160 mmol) obtained in Example 17, (2) was dissolved in anhydrous DMF (2.5 mL), 3-phenylproionaldehyde (64 mg, 0.486 mmol), and ammonium hydrogencarbonate (64 mg, 0.480 mmol) were added to the solution, and the resulting mixture was stirred at room temperature for 0.5 hour. 8.8 M aqueous glyoxal (55 μL, 0.48 mmol) was added to the mixture, and the resulting mixture was stirred at room temperature for 16 hours. To the reaction mixture, water was added, the resulting mixture was extracted with chloroform, and the organic layer was dried over anhydrous sodium sulfate. The solvent was evaporated under reduced pressure, and the residue was purified by silica gel chromatography (methanol/chloroform=3/100) to obtain the title compound (8 mg) as yellow oil.

$^1$H NMR (CDCl$_3$, 400 MHz) δ: 2.95 (2H, t, J=8 Hz), 3.06 (2H, t, J=8 Hz), 3.97 (1H, br s), 4.87 (1H, br s), 6.98 (1H, d, J=1 Hz), 7.05 (2H, d, J=7 Hz), 7.1-7.3 (5H, m), 7.33 (1H, d, J=8 Hz), 7.6-7.8 (5H, m), 7.94 (1H, m), 8.27 (1H, d, J=8 Hz), 9.49 (1H, s)

(2) 5-[4-(2-Phenethyl-1H-imidazol-1-yl)phenyl]-1H-naphtho[1,2-e][1,4]diazepin-2(3H)-one dihydrochloride By using 5-[4-(2-phenethyl-1H-imidazol-1-yl)phenyl]-1H-naphtho[1,2-e][1,4]diazepin-2(3H)-one obtained above, the title compound was obtained as a yellow amorphous substance in the same manner as that of Example 39.

$^1$H NMR (DMSO-d$_6$, 400 MHz) δ: 2.95 (2H, t, J=8 Hz), 3.21 (2H, t, J=8 Hz), 3.88 (1H, br s), 4.63 (1H, br s), 7.02 (2H, d, J=7 Hz), 7.1-7.3 (4H, m), 7.47 (2H, d, J=8 Hz), 7.7-7.8 (5H, m), 7.85 (1H, d, J=2 Hz), 7.90 (1H, d, J=2 Hz), 8.0-8.1 (1H, m), 8.39 (1H, d, J=9 Hz), 10.96 (1H, s)

Example 42

5-[4-[2-(3-Methoxyphenethyl)-1H-imidazol-1-yl] phenyl]-1H-naphtho[1,2-b][1,4]diazepine-2,4(3H, 5H)-dione hydrochloride (1) 5-[4-[2-(3-Methoxyphenethyl)-1H-imidazol-1-yl]phenyl]-1H-naphtho[1,2-b][1,4]diazepine-2,4(3H, 5H)-dione By using $N^1$-(1-nitronaphthalen-2-yl)benzene-1,4-diamine obtained in Example 3, (1), and 3-(3-(methoxy)phenyl)propionic acid, the title compound (109 mg, yield 26%) was obtained as white crystals in the same manner as that of Example 3, (2), (4), (5), (6), Example 21, (1), (2), and (3).

$^1$H NMR (CDCl$_3$, 400 MHz) δ: 1.5-1.6 (4H, m), 2.9-3.0 (2H, m), 3.0-3.1 (2H, m), 3.64 (2H, s), 3.72 (3H, s), 6.58 (1H, s), 6.64 (1H, d, J=3 Hz), 6.71 (1H, dd, J=2 Hz, 3 Hz), 6.97 (1H, s), 7.03 (1H, d, J=4 Hz), 7.0-7.2 (4H, m), 7.3-7.4 (2H, m), 7.6-7.7 (2H, m), 7.72 (1H, t, J=3 Hz), 7.88 (1H, d, J=3 Hz), 8.11 (1H, br s)

(2) 5-[4-[2-(3-Methoxyphenethyl)-1H-imidazol-1-yl]phenyl]-1H-naphtho[1,2-b][1,4]diazepine-2,4(3H, 5H)-dione hydrochloride The title compound (19 mg, yield 37%) was obtained as brown crystals in the same manner as that of Example 3, (7).

$^1$H NMR (DMSO-d$_6$, 400 MHz) δ: 2.92 (2H, t, J=8 Hz), 3.1-3.2 (3H, m), 3.64 (3H, s), 3.76 (1H, s), 6.5-6.6 (2H, m), 6.75 (1H, d, J=8 Hz), 6.99 (1H, d, J=9 Hz), 7.13 (1H, t, J=8 Hz), 7.46 (4H, s), 7.62 (1H, t, J=7 Hz), 7.69 (1H, t, J=7 Hz), 7.74 (1H, d, J=9 Hz), 7.83 (1H, d, J=2 Hz), 7.90 (1H, d, J=2 Hz), 7.95 (1H, d, J=8 Hz), 8.29 (1H, d, 8 Hz), 10.97 (1H, br s)

Example 43

5-[4-[2-(3-Hydroxyphenethyl)-1H-imidazol-1-yl] phenyl]-1H-naphtho[1,2-b][1,4]diazepine-2,4(3H, 5H)-dione hydrochloride (1) 5-[4-[2-(3-Hydroxyphenethyl)-1H-imidazol-1-yl] phenyl]-1H-naphtho[1,2-b][1,4]diazepine-2,4(3H, 5H)-dione By using 5-[4-[2-(3-methoxyphenethyl)-1H-imidazol-1-yl]phenyl]-1H-naphtho[1,2-b][1,4]diazepine-2,4(3H,5H)-dione obtained above, the title compound (97 mg, yield 88%) was obtained as a slightly brown amorphous substance in the same manner as that of Example 2.

$^1$H NMR (CDCl$_3$, 400 MHz) δ: 2.6-2.9 (2H, m), 2.95 (2H, t, J=3 Hz), 3.49 (1H, br s), 3.66 (2H, s), 6.23 (1H, s), 6.50 (1H, d, J=3 Hz), 6.65 (1H, d, J=3 Hz), 7.0-7.2 (5H, m), 7.34 (2H, d, J=3 Hz), 7.6-7.7 (2H, m), 7.74 (1H, t, J=3 Hz), 7.89 (1H, d, J=3 Hz), 8.13 (1H, br s), 8.63 (1H, br s)

(2) 5-[4-[2-(3-Hydroxyphenethyl)-1H-imidazol-1-yl] phenyl]-1H-naphtho[1,2-b][1,4]diazepine-2,4(3H, 5H)-dione hydrochloride By using 5-[4-[2-(3-hydroxyphenethyl)-1H-imidazol-1-yl]phenyl]-1H-naphtho[1,2-b][1,4]diazepine-2,4(3H,5H)-dione obtained above, the title compound (57 mg, yield 55%) was obtained as a pale yellow amorphous substance in the same manner as that of Example 3, (7).

$^1$H NMR (DMSO-d$_6$, 400 MHz) δ: 2.84 (2H, t, J=8 Hz), 3.0-3.2 (311H, m), 3.77 (1H, d, J=12 Hz), 6.40 (1H, d, J=8 Hz), 6.41 (1H, s), 6.59 (1H, d, J=8 Hz), 6.9-7.1 (2H, m), 7.49 (2H, q, J=9 Hz), 7.61 (1H, t, J=7 Hz), 7.69 (1H, t, J=7 Hz), 7.75 (1H, d, J=9 Hz), 7.81 (1H, s), 7.9-8.0 (2H, m), 8.29 (1H, d, 9 Hz), 9.36 (1H, br s), 10.97 (1H, br s)

Example 44

3-[2-[1-[4-(2,4-Dioxo-3,4-dihydro-1H-naphtho[1,2-b][1,4]diazepin-5(2H)-yl)phenyl]-1H-tetrazol-5-yl] ethyl]benzonitrile By using $N^1$-(1-nitronaphthalen-2-yl)benzene-1,4-diamine (1.0 g, 3.58 mmol) obtained in Example 3, (1), and 3-(3-cyanophenyl)propionic acid (735 mg, 4.30 mmol), the title compound was obtained as a pale yellow amorphous substance in the same manner as that of Example 3, (1), (2), (3), (4), (5), and (6).

$^1$H NMR (DMSO-d$_6$, 400 MHz) δ: 3.1-3.2 (3H, m), 3.2-3.3 (2H, m), 3.77 (1H, d, J=12 Hz), 7.03 (1H, d, J=9 Hz), 7.4-7.8 (11H, m), 7.94 (1H, d, J=8 Hz), 8.28 (1H, d, J=8 Hz), 10.97 (1H, br s)

Example 45

3-[2-[1-[4-(2,4-Dioxo-3,4-dihydro-1H-naphtho[1,2-b][1,4]diazepin-5(2H)-yl)phenyl]-1H-tetrazol-5-yl] ethyl]benzamide To 3-[2-[1-[4-(2,4-dioxo-3,4-dihydro-1H-naphtho[1,2-b] [1,4]diazepin-5(2H)-yl)phenyl]-1H-tetrazol-5-yl]ethyl]benzonitrile (536 mg, 1.07 mmol) obtained in Example 44, 105% polyphosphoric acid (5 mL) was added, and the mixture was stirred at 115° C. for 1.5 hours. The reaction mixture was left to cool, then diluted with chloroform, and neutralized by using 1 M aqueous sodium hydroxide. The organic layer was dried over anhydrous sodium sulfate, then the solvent was evaporated under reduced pressure, and the residue was purified by silica gel column chromatography (chloroform/methanol=100/3) to obtain the title compound (402 mg, yield 73%) as a pale yellow amorphous substance.

$^1$H NMR (DMSO-d$_6$, 400 MHz) δ: 3.11 (2H, t, J=8 Hz), 3.19 (1H, d, J=12 Hz), 3.2-3.3 (2H, m), 3.76 (1H, d, J=12 Hz), 7.03 (1H, d, J=9 Hz), 7.2-7.4 (3H, m), 7.47 (2H, d, J=9 Hz), 7.5-7.7 (6H, m), 7.74 (1H, d, J=9 Hz), 7.90 (1H, br s), 7.94 (1H, d, J=8 Hz), 8.28 (1H, d, J=9 Hz), 10.96 (1H, br s)

Example 46

5-[4-[5-[2-(2-Methoxypyridin-3-yl)ethyl]-1H-tetrazol-1-yl]phenyl]-1H-naphtho[1,2-b][1,4]diazepine-2, 4(3H,5H)-dione By using $N^1$-(1-nitronaphthalen-2-yl)benzene-1,4-diamine (100 mg, 0.36 mmol) obtained in Example 3, (1), and 3-(2-methoxypyridin-3-yl)propionic acid (78 mg, 0.43 mmol), the title compound was obtained as a pale yellow amorphous substance in the same manner as that of Example 3, (2), (3), (4), (5), and (6).

$^1$H NMR (DMSO-d$_6$, 400 MHz) δ: 2.95 (2H, t, J=7 Hz), 3.20 (1H, d, J=12 Hz), 3.24 (2H, t, J=7 Hz), 3.74 (3H, s), 3.78 (1H, d, J=12 Hz), 6.86 (1H, dd, J=5 Hz, 7 Hz), 7.07 (1H, d, J=9 Hz), 7.43 (1H, d, J=7 Hz), 7.49 (2H, d, J=8 Hz), 7.6-7.7 (3H, m), 7.69 (1H, t, J=7 Hz), 7.76 (1H, d, J=9 Hz), 7.96 (1H, d, J=8 Hz), 7.99 (1H, dd, J=1 Hz, 5 Hz), 8.29 (1H, d, J=8 Hz), 10.97 (1H, s)

Example 47

5-[4-[5-[2-(Dimethylamino)benzyl]-1H-tetrazol-1-yl]phenyl]-1H-naphtho[1,2-b][1,4]diazepine-2,4(3H,5H)-dione mesylate (1) 5-[4-[5-[2-(Dimethylamino)benzyl]-1H-tetrazol-1-yl]phenyl]-1H-naphtho[1,2-b][1,4]diazepine-2,4(3H,5H)-dione By using $N^1$-(1-nitronaphthalen-2-yl)benzene-1,4-diamine (60 mg, 0.22 mmol) obtained in Example 3, (1), and 2-[2-(dimethylamino)phenyl]acetic acid (42 mg, 0.24 mmol), the title compound was obtained in the same manner as that of Example 3, (2), (3), (4), (5), and (6).

$^1$H NMR (DMSO-$d_6$, 400 MHz) δ: 2.38 (6H, s), 3.18 (1H, d, J=12 Hz), 3.74 (1H, d, J=12 Hz), 4.43 (2H, s), 6.86 (1H, d, J=9 Hz), 6.95 (1H, t, J=7 Hz), 7.03 (1H, d, J=8 Hz), 7.08 (1H, d, J=8 Hz), 7.22 (1H, t, J=7 Hz), 7.38 (2H, d, J=9 Hz), 7.57 (2H, d, J=9 Hz), 7.62 (1H, t, J=8 Hz), 7.69 (1H, t, J=7 Hz), 7.77 (1H, d, J=9 Hz), 7.97 (1H, d, J=8 Hz), 8.27 (1H, d, J=8 Hz), 10.94 (1H, s)

(2) 5-[4-[5-[2-(Dimethylamino)benzyl]-1H-tetrazol-1-yl]phenyl]-1H-naphtho[1,2-b][1,4]diazepine-2,4(3H,5H)-dione mesylate 5-[4-[5-[2-(Dimethylamino)benzyl]-1H-tetrazol-1-yl]phenyl]-1H-naphtho[1,2-b][1,4]diazepine-2,4(3H,5H)-dione (33.3 mg, 0.066 mmol) obtained above was dissolved in methanol, a 0.5 M solution of methanesulfonic acid in ethyl acetate (132 μM, 0.066 mmol) was added to the solution, and the solvent was evaporated under reduced pressure to obtain the title compound as a slightly brown amorphous substance.

$^1$H NMR (DMSO-$d_6$, 400 MHz) δ: 2.32 (3H, s), 2.5-2.7 (6H, m), 3.19 (1H, d, J=12 Hz), 3.76 (1H, d, J=12 Hz), 4.50 (2H, s), 6.91 (1H, d, J=9 Hz), 7.15 (2H, br s), 7.34 (2H, br s), 7.44 (1H, d, J=8 Hz), 7.6-7.7 (4H, m), 7.77 (1H, d, J=9 Hz), 7.97 (1H, d, J=8 Hz), 8.28 (1H, d, J=8 Hz), 10.96 (1H, s)

Example 48

4-[2-[1-[4-(2,4-Dioxo-3,4-dihydro-1H-naphtho[1,2-b][1,4]diazepin-5(2H)-yl)phenyl]-1H-imidazol-2-yl]ethyl]benzonitrile By using $N^1$-(1-nitronaphthalen-2-yl)benzene-1,4-diamine (100 mg, 0.36 mmol) obtained in Example 3, (1), and 3-(4-cyanophenyl)propionic acid (75 mg, 0.43 mmol), the title compound was obtained as a slightly brown amorphous substance in the same manner as that of Example 3, (2), (4), (5), (6), Example 21, (1), (2), and (3).

$^1$H NMR (DMSO-$d_6$, 400 MHz) δ: 2.9-3.0 (4H, m), 3.19 (1H, dd, J=1 Hz, 12 Hz), 3.75 (1H, d, J=12 Hz), 7.02 (2H, d, J=9 Hz), 7.31 (2H, d, J=8 Hz), 7.37 (3H, d, J=9 Hz), 7.43 (2H, d, J=9 Hz), 7.62 (1H, t, J=7 Hz), 7.68 (3H, d, J=8 Hz), 7.74 (1H, d, J=9 Hz), 7.94 (1H, d, J=7 Hz), 8.28 (1H, d, J=9 Hz), 10.95 (1H, s)

Example 49

4-[2-[1-[4-(2,4-Dioxo-3,4-dihydro-1H-naphtho[1,2-b][1,4]diazepin-5(2H)-yl)phenyl]-1H-imidazol-2-yl]ethyl]benzamide 4-[2-[1-[4-(2,4-Dioxo-3,4-dihydro-1H-naphtho[1,2-b][1,4]diazepin-5(2H)-yl)phenyl]-1H-imidazol-2-yl]ethyl]benzonitrile (12 mg, 0.023 mmol) obtained in Example 48, and 105% polyphosphoric acid (0.14 ml) were mixed, and the mixture was stirred with heating at 115° C. for 1 hour under a nitrogen atmosphere. The reaction mixture was left to cool, then saturated aqueous sodium hydrogencarbonate was added to the reaction mixture, the resulting mixture was extracted with chloroform, and the organic layer was dried over sodium sulfate. The solvent was evaporated under reduced pressure, and the residue was purified by silica gel column chromatography (chloroform/methanol=20/1) to obtain the title compound (7 mg, yield 61%) as a slightly brown amorphous substance.

$^1$H NMR (DMSO-$d_6$, 400 MHz) δ: 2.9-3.0 (4H, m), 3.18 (1H, d, J=12 Hz), 3.75 (1H, d, J=12 Hz), 6.98 (1H, d, J=1 Hz), 7.02 (1H, d, J=9 Hz), 7.16 (2H, d, J=8 Hz), 7.23 (1H, s), 7.32 (1H, d, J=1 Hz), 7.36 (2H, d, J=9 Hz), 7.42 (2H, d, J=9 Hz), 7.61 (1H, t, J=7 Hz), 7.68 (1H, t, J=8 Hz), 7.7-7.8 (3H, m), 7.85 (1H, s), 7.94 (1H, d, J=8 Hz), 8.28 (1H, d, J=9 Hz), 10.94 (1H, s)

Example 50

5-[4-(2-Phenyl-1H-imidazol-1-yl)phenyl]-1H-naphtho[1,2-b][1,4]diazepine-2,4(3H,5H)-dione (1) 1-(4-Nitrophenyl)-2-phenyl-1H-imidazole 2-Phenyl-1H-imidazole (500 mg, 3.46 mmol), and potassium carbonate (960 mg, 6.95 mmol) were suspended in dry dimethyl sulfoxide (28 mL), and the suspension was stirred at room temperature for 15 minutes under a nitrogen atmosphere. To this reaction mixture, 1-fluoro-4-nitrobenzene (610 mg, 4.32 mmol) was added with stirring, and the resulting mixture was stirred with heating at 130° C. for 17 hours. The reaction mixture was left to cool, and then poured into ice water, and the resulting mixture was extracted with ethyl acetate. The organic layer was washed with saturated brine, and dried over anhydrous sodium sulfate. The solvent was evaporated under reduced pressure to obtain the title compound.

$^1$H NMR (CDCl$_3$, 400 MHz) δ: 7.22 (1H, d, J=1 Hz), 7.3-7.4 (8H, m), 8.27 (2H, d, J=9 Hz)

(2) 4-(2-Phenyl-1H-imidazol-1-yl)aniline

By using 1-(4-nitrophenyl)-2-phenyl-1H-imidazole obtained above, the title compound was obtained in the same manner as that of Example 3, (4).

$^1$H NMR (CDCl$_3$, 400 MHz) δ: 3.82 (2H, s), 6.66 (2H, d, J=8 Hz), 7.00 (2H, d, J=9 Hz), 7.08 (1H, d, J=1 Hz), 7.21 (1H, d, J=1 Hz), 7.2-7.3 (3H, m), 7.4-7.5 (2H, m)

(3) Ethyl 3-[[2-[[4-(2-phenyl-1H-imidazol-1-yl)phenyl]amino]naphthalen-1-yl]amino]-3-oxopropionate By using 4-(2-phenyl-1H-imidazol-1-yl)aniline (120 mg, 0.51 mmol) obtained above, and 1-nitro-2-naphthyl trifluoromethanesulfonate (136 mg, 0.43 mmol), the title compound was obtained (60 mg, yield 29% for three steps) in the same manner as that of Example 3, (1), (4), and (5).

$^1$H NMR (CDCl$_3$, 400 MHz) δ: 1.37 (3H, t, J=7 Hz), 3.68 (2H, s), 4.35 (2H, q, J=7 Hz), 6.09 (1H, s), 7.00 (2H, d, J=9 Hz), 7.09 (2H, d, J=9 Hz), 7.12 (1H, d, J=1 Hz), 7.23 (1H, d, J=1 Hz), 7.2-7.3 (3H, m), 7.42 (1H, t, J=7 Hz), 7.4-7.5 (2H, m), 7.55 (1H, t, J=7 Hz), 7.62 (1H, d, J=9 Hz), 7.76 (1H, d, J=9 Hz), 7.82 (1H, d, J=8 Hz), 7.93 (1H, d, J=8 Hz), 9.58 (1H, s)

(4) 5-[4-(2-Phenyl-1H-imidazol-1-yl)phenyl]-1H-naphtho[1,2-b][1,4]diazepine-2,4(3H,5H)-dione By using ethyl 3-[[2-[[4-(2-phenyl-1H-imidazol-1-yl)phenyl]amino]naphthalen-1-yl]amino]-3-oxopropionate (60 mg, 0.12 mmol) obtained above, the title compound (10 mg, yield 19%) was obtained as a slightly brown amorphous substance in the same manner as that of Example 3, (6).

$^1$H NMR (DMSO-d$_6$, 400 MHz) δ: 3.18 (1H, d, J=12 Hz), 3.74 (1H, d, J=12 Hz), 6.99 (1H, d, J=9 Hz), 7.19 (1H, d, J=1 Hz), 7.3-7.4 (9H, m), 7.55 (1H, d, J=1 Hz), 7.61 (1H, t, J=7 Hz), 7.68 (1H, t, J=7 Hz), 7.76 (1H, d, J=9 Hz), 7.94 (1H, d, J=8 Hz), 8.27 (1 Hz, d, J=8 Hz), 10.94 (1H, s)

Example 51

5-[4-[2-(2-Methoxyphenyl)-1H-imidazol-1-yl]phenyl]-1H-naphtho[1,2-b][1,4]diazepine-2,4(3H,5H)-dione With reference to information described in a reference [J. Am. Chem. Soc., 134, 9796 (2012)], 5-(4-aminophenyl)-1H-naphtho[1,2-b][1,4]diazepine-2,4(3H)-dione (25 mg, 0.079 mmol) [WO2013/105608, Example 1, (3)], and 2-methoxybenzaldehyde (20 μL, 0.16 mmol) were dissolved in methanol (1 mL), ammonium carbonate (13 mg, 0.16 mmol), and glyoxal (18 μL, 0.16 mmol) were added to the solution, and the resulting mixture was stirred with heating at 60° C. for 9 hours under a nitrogen atmosphere. After the reaction, the solvent was evaporated, water was added to the residue, and the mixture was extracted with chloroform. The organic layer was dried over anhydrous sodium sulfate, then the solvent was evaporated under reduced pressure, and the residue was purified by silica gel column chromatography (chloroform/methanol=30/1) to obtain the title compound (4.6 mg, yield 12%) as a slightly brown amorphous substance.

$^1$H NMR (DMSO-d$_6$, 400 MHz) δ: 3.14 (1H, d, J=12 Hz), 3.25 (3H, s), 3.71 (1H, d, J=12 Hz), 6.92 (2H, t, J=9 Hz), 7.04 (1H, t, J=8 Hz), 7.1-7.2 (5H, m), 7.38 (1H, t, J=7 Hz), 7.51 (1H, d, J=6 Hz), 7.6-7.7 (2H, m), 7.67 (1H, t, J=7 Hz), 7.72 (1H, d, J=9 Hz), 7.93 (1H, d, J=8 Hz), 8.25 (1H, d, J=9 Hz), 10.91 (1H, s)

Example 52

2-[[2-[4-(2,4-Dioxo-3,4-dihydro-1H-naphtho[1,2-b][1,4]diazepin-5(2H)-yl)phenyl]-1H-imidazol-1-yl]methyl]benzonitrile By using 2-(4-nitrophenyl)-1H-imidazole [Heterocycles, 76, 507 (2008)](50 mg, 0.26 mmol), and 2-(bromomethyl)benzonitrile (62 mg, 0.32 mmol), the title compound was obtained as a slightly brown amorphous substance in the same manner as that of Example 24, (1), (2), (3), and (4).

$^1$H NMR (DMSO-d$_6$, 400 MHz) δ: 3.16 (1H, d, J=12 Hz), 3.72 (1H, d, J=12 Hz), 5.58 (2H, s), 6.91 (1H, d, J=7 Hz), 6.93 (1H, d, J=9 Hz), 7.11 (1H, d, J=1 Hz), 7.27 (2H, d, J=8 Hz), 7.32 (1H, s), 7.49 (1H, t, J=7 Hz), 7.6-7.8 (6H, m), 7.85 (1H, d, J=8 Hz), 7.94 (1H, d, J=8 Hz), 8.26 (1H, d, J=9 Hz), 10.92 (1H, s)

Example 53

2-[[2-[4-(2,4-Dioxo-3,4-dihydro-1H-naphtho[1,2-b][1,4]diazepin-5(2H)-yl)phenyl]-1H-imidazol-1-yl]methyl]benzamide By using 2-[[2-[4-(2,4-dioxo-3,4-dihydro-1H-naphtho[1,2-b][1,4]diazepin-5(2H)-yl)phenyl]-1H-imidazol-1-yl]methyl]benzonitrile (6.9 mg, 0.014 mmol) obtained in Example 52, the title compound was obtained as white crystals in the same manner as that of Example 49.

$^1$H NMR (DMSO-d$_6$, 400 MHz) δ: 3.16 (1H, d, J=12 Hz), 3.72 (1H, d, J=12 Hz), 5.55 (2H, s), 6.68 (1H, d, J=7 Hz), 6.98 (1H, d, J=9 Hz), 7.10 (1H, s), 7.26 (2H, d, J=8 Hz), 7.31 (1H, s), 7.3-7.4 (2H, m), 7.48 (1H, s), 7.5-7.6 (4H, m), 7.66 (1H, d, J=8 Hz), 7.70 (1H, d, J=9 Hz), 7.9-8.0 (2H, m), 8.26 (1H, d, J=8 Hz), 10.93 (1H, s)

Example 54

2-[2-[1-[4-(2,4-Dioxo-3,4-dihydro-1H-naphtho[1,2-b][1,4]diazepin-5(2H)-yl)phenyl]-1H-imidazol-2-yl]ethyl]benzonitrile By using N$^1$-(1-nitronaphthalen-2-yl)benzene-1,4-diamine (150 mg, 0.54 mmol) obtained in Example 3, (1), and 3-(2-cyanophenyl)propionic acid (113 mg, 0.64 mmol), the title compound was obtained as white crystals in the same manner as that of Example 3, (2), (4), (5), (6), Example 21, (1), (2), and (3).

$^1$H NMR (DMSO-d$_6$, 400 MHz): δ: 3.0-3.1 (2H, m), 3.1-3.2 (3H, m), 3.75 (1H, d, J=12 Hz), 6.99 (1H, d, J=1 Hz), 7.05 (1H, d, J=9 Hz), 7.3-7.4 (7H, m), 7.56 (1H, dt, J=1 Hz, 8 Hz), 7.61 (1H, t, J=7 Hz), 7.68 (2H, t, J=8 Hz), 7.75 (1H, d, J=9 Hz), 7.95 (1H, d, J=8 Hz), 8.27 (1H, d, J=8 Hz), 10.95 (1H, s)

Example 55

2-[2-[1-[4-(2,4-Dioxo-3,4-dihydro-1H-naphtho[1,2-b][1,4]diazepin-5(2H)-yl)phenyl]-1H-imidazol-2-yl]ethyl]benzamide By using 2-[2-[1-[4-(2,4-dioxo-3,4-dihydro-1H-naphtho[1,2-b][1,4]diazepin-5(2H)-yl)phenyl]-1H-imidazol-2-yl]ethyl]benzonitrile (28.5 mg, 0.057 mmol) obtained in Example 54, the title compound was obtained as a slightly brown amorphous substance in the same manner as that of Example 49.

$^1$H NMR (DMSO-d$_6$, 400 MHz) δ: 2.93 (1H, dd, J=3 Hz, 8 Hz), 2.95 (1H, d, J=6 Hz), 3.09 (2H, t, J=8 Hz), 3.18 (1H, d, J=12 Hz), 3.74 (1H, d, J=12 Hz), 6.97 (1H, d, J=1 Hz), 7.04 (1H, d, J=9 Hz), 7.10 (1H, d, J=7 Hz), 7.20 (1H, t, J=7 Hz), 7.2-7.3 (4H, m), 7.36 (2H, d, J=9 Hz), 7.41 (2H, d, J=9 Hz), 7.61 (1H, t, J=7 Hz), 7.68 (1H, t, J=7 Hz), 7.73 (1H, d, J=9 Hz), 7.83 (1H, s), 7.93 (1H, d, J=8 Hz), 8.27 (1H, d, J=8 Hz), 10.96 (1H, s)

Example 56

3-[2-[1-[4-(2,4-Dioxo-3,4-dihydro-1H-naphtho[1,2-b][1,4]diazepin-5(2H)-yl)phenyl]-1H-imidazol-2-yl]ethyl]benzonitrile By using N$^1$-(1-nitronaphthalen-2-yl)benzene-1,4-diamine (100 mg, 0.36 mmol) obtained in Example 3, (1), and 3-(3-cyanophenyl)propionic acid (75 mg, 0.43 mmol), the title compound was obtained as a slightly brown amorphous substance in the same manner as that of Example 3, (2), (4), (5), (6), Example 21, (1), (2), and (3).

$^1$H NMR (DMSO-d$_6$, 400 MHz) δ: 2.9-3.0 (4H, m), 3.18 (1H, d, J=12 Hz), 3.74 (1H, d, J=12 Hz), 6.98 (1H, d, J=1 Hz), 7.03 (1H, d, J=9 Hz), 7.33 (1H, d, J=1 Hz), 7.36 (2H, d, J=9 Hz), 7.4-7.5 (4H, m), 7.6-7.7 (3H, m), 7.68 (1H, t, J=7 Hz), 7.74 (1H, d, J=9 Hz), 7.93 (1H, d, J=7 Hz), 8.28 (1H, d, J=8 Hz), 10.94 (1H, s)

Example 57

3-[2-[1-[4-(2,4-Dioxo-3,4-dihydro-1H-naphtho[1,2-b][1,4]diazepin-5(2H)-yl)phenyl]-1H-imidazol-2-yl]ethyl]benzamide By using 3-[2-[1-[4-(2,4-dioxo-3,4-dihydro-1H-naphtho[1,2-b][1,4]diazepin-5(2H)-yl)phenyl]-1H-imidazol-2-yl]ethyl]benzonitrile (186.8 mg, 0.38 mmol) obtained in Example 56, the title compound was obtained as a slightly brown amorphous substance in the same manner as that of Example 49.

$^1$H NMR (DMSO-d$_6$, 400 MHz) δ: 2.9-3.0 (4H, m), 3.18 (1H, d, J=12 Hz), 3.74 (1H, d, J=12 Hz), 6.98 (1H, s), 7.03 (1H, d, J=9 Hz), 7.23 (1H, d, J=7 Hz), 7.2-7.3 (3H, m), 7.36 (2H, d, J=8 Hz), 7.43 (2H, d, J=8 Hz), 7.61 (1H, t, J=7 Hz), 7.6-7.7 (3H, m), 7.74 (1H, d, J=9 Hz), 7.88 (1H, s), 7.94 (1H, d, J=8 Hz), 8.27 (1H, d, J=9 Hz), 10.94 (1H, s)

Example 58

3-[2-[1-[4-(2,4-Dioxo-3,4-dihydro-1H-naphtho[1,2-b][1,4]diazepin-5(2H)-yl)phenyl]-1H-imidazol-2-yl]ethyl]benzamide hydrochloride By using 3-[2-[1-[4-(2,4-dioxo-3,4-dihydro-1H-naphtho[1,2-b][1,4]diazepin-5(2H)-yl)phenyl]-1H-imidazol-2-yl]ethyl]benzamide (126.2 mg, 0.24 mmol) obtained in Example 57, the title compound was obtained as a slightly brown amorphous substance in the same manner as that of Example 3, (7).

$^1$H NMR (DMSO-d$_6$, 400 MHz) δ: 3.00 (2H, t, J=7 Hz), 3.2-3.3 (3H, m), 3.77 (1H, d, J=12 Hz), 7.01 (1H, d, J=9 Hz), 7.16 (1H, d, J=7 Hz), 7.31 (2H, t, J=8 Hz), 7.46 (2H, d, J=9 Hz), 7.53 (2H, d, J=9 Hz), 7.6-7.7 (2H, m), 7.68 (2H, t, J=8 Hz), 7.76 (1H, d, J=9 Hz), 7.82 (1H, s), 7.9-8.0 (3H, m), 8.29 (1H, d, J=8 Hz), 10.96 (1H, s)

Example 59

5-[4-[2-[4-(Methylsulfonyl)phenethyl]-1H-imidazol-1-yl]phenyl]-1H-naphtho[1,2-b][1,4]diazepine-2,4(3H,5H)-dione hydrochloride

(1) 5-[4-[2-[4-(Methylsulfonyl)phenethyl]-1H-imidazol-1-yl]phenyl]-1H-naphtho[1,2-b][1,4]diazepine-2,4(3H,5H)-dione By using N$^1$-(1-nitronaphthalen-2-yl)benzene-1,4-diamine (150 mg, 0.54 mmol) obtained in Example 3, (1), and 3-[4-(methylsulfonyl)phenyl]propionic acid (147 mg, 0.64 mmol), the title compound was obtained in the same manner as that of Example 3, (2), (4), (5), (6), Example 21, (1), (2), and (3).

$^1$H NMR (DMSO-d$_6$, 400 MHz) δ: 2.9-3.1 (4H, m), 3.15 (3H, s), 3.18 (1H, d, J=12 Hz), 3.75 (1H, d, J=12 Hz), 6.99 (1H, d, J=1 Hz), 7.02 (1H, d, J=9 Hz), 7.33 (1H, d, J=2 Hz), 7.34 (2H, d, J=9 Hz), 7.37 (2H, d, J=8 Hz), 7.43 (2H, d, J=9 Hz), 7.61 (1H, t, J=7 Hz), 7.68 (1H, t, J=7 Hz), 7.7-7.8 (3H, m), 7.94 (1H, d, J=7 Hz), 8.28 (1H, d, J=9 Hz), 10.94 (1H, s)

(2) 5-[4-[2-[4-(Methylsulfonyl)phenethyl]-1H-imidazol-1-yl]phenyl]-1H-naphtho[1,2-b][1,4]diazepine-2,4(3H,5H)-dione hydrochloride By using 5-[4-[2-[4-(methylsulfonyl)phenethyl]-1H-imidazol-1-yl]phenyl]-1H-naphtho[1,2-b][1,4]diazepine-2,4(3H,5H)-dione (71.5 mg, 0.13 mmol) obtained above, the title compound was obtained as a slightly brown amorphous substance in the same manner as that of Example 3, (7).

$^1$H NMR (DMSO-d$_6$, 400 MHz) δ: 3.06 (2H, t, J=8 Hz), 3.16 (3H, s), 3.2-3.3 (3H, m), 3.77 (1H, d, J=12 Hz), 7.01 (1H, d, J=9 Hz), 7.32 (2H, d, J=8 Hz), 7.47 (2H, d, J=9 Hz), 7.55 (2H, d, J=9 Hz), 7.63 (1H, t, J=8 Hz), 7.70 (1H, t, J=8 Hz), 7.76 (1H, d, J=9 Hz), 7.80 (3H, d, J=8 Hz), 7.90 (1H, s), 7.95 (1H, d, J=8 Hz), 8.30 (1H, d, J=8 Hz), 10.97 (1H, s)

Example 60

5-[4-[2-(2-Fluoro-3-methoxyphenethyl)-1H-imidazol-1-yl]phenyl]-1H-naphtho[1,2-b][1,4]diazepine-2,4(3H,5H)-dione hydrochloride

(1) 5-[4-[2-(2-Fluoro-3-methoxyphenethyl)-1H-imidazol-1-yl]phenyl]-1H-naphtho[1,2-b][1,4]diazepine-2,4(3H,5H)-dione By using N$^1$-(1-nitronaphthalen-2-yl)benzene-1,4-diamine (150 mg, 0.54 mmol) obtained in Example 3, (1), and 3-(2-fluoro-3-methoxyphenyl)propionic acid (128 mg, 0.65 mmol), the title compound was obtained in the same manner as that of Example 3, (2), (4), (5), (6), Example 21, (1), (2), and (3).

$^1$H NMR (DMSO-d$_6$, 400 MHz) δ: 2.90 (4H, s), 3.18 (1H, d, J=12 Hz), 3.75 (1H, d, J=12 Hz), 3.78 (3H, s), 6.6-6.7 (1H, m), 6.9-7.0 (3H, m), 7.04 (1H, d, J=9 Hz), 7.31 (1H, d, J=2 Hz), 7.35 (2H, d, J=9 Hz), 7.41 (2H, d, J=9 Hz), 7.61 (1H, t, J=7 Hz), 7.68 (1H, t, J=7 Hz), 7.73 (1H, d, J=9 Hz), 7.94 (1H, d, J=8 Hz), 8.28 (1H, d, J=8 Hz), 10.94 (1H, s)

(2) 5-[4-[2-(2-Fluoro-3-methoxyphenethyl)-1H-imidazol-1-yl]phenyl]-1H-naphtho[1,2-b][1,4]diazepine-2,4(3H,5H)-dione hydrochloride By using 5-[4-[2-(2-fluoro-3-methoxyphenethyl)-1H-imidazol-1-yl]phenyl]-1H-naphtho[1,2-b][1,4]diazepine-2,4(3H,5H)-dione obtained above, the title compound was obtained as a slightly brown amorphous substance in the same manner as that of Example 3, (7).

$^1$H NMR (DMSO-d$_6$, 400 MHz) δ: 2.9-3.0 (2H, m), 3.1-3.2 (3H, m), 3.78 (1H, d, J=12 Hz), 3.78 (3H, s), 6.5-6.6 (1H, m), 7.0-7.1 (3H, m), 7.46 (2H, d, J=9 Hz), 7.49 (2H, d, J=9 Hz), 7.63 (1H, t, J=7 Hz), 7.70 (1H, t, J=7 Hz), 7.75 (1H, d, J=9 Hz), 7.78 (1H, s), 7.90 (1H, s), 7.96 (1H, d, J=8 Hz), 8.30 (1H, d, J=8 Hz), 10.97 (1H, s)

Example 61

5-[4-[2-(3-Methoxyphenethyl)-1H-imidazol-1-yl]phenyl]-5,8,9,10-tetrahydroindeno[4,5-b][1,4]diazepine-2,4(1H,3H)-dione hydrochloride (1) $N^1$-(4-Nitro-2,3-dihydro-1H-inden-5-yl)benzene-1,4-diamine 4-Nitro-2,3-dihydro-1H-inden-5-yl trifluoromethanesulfonate (3.72 g, 12 mmol) [WO2012/008478, Example 4, (1)], p-phenylenediamine (13.0 g, 120 mmol), potassium carbonate (1.66 g, 12 mmol), tetrakis(triphenylphosphine)palladium (0.69 g, 0.6 mmol), triphenylphosphine (0.31 g, 1.2 mmol), and dry tetrahydrofuran (120 mL) were mixed, and the mixture was refluxed by heating for 12 hours under a nitrogen atmosphere. The reaction mixture was left to cool, then water was added to the mixture, and the resulting mixture was extracted with ethyl acetate. The organic layer was washed with saturated brine, and dried over anhydrous sodium sulfate. The solvent was evaporated under reduced pressure, and the residue was purified by silica gel column chromatography (chloroform), and washed with hexane to obtain the title compound (2.80 g, yield 87%) as dark brown crystals.

$^1$H NMR (CDCl$_3$, 400 MHz) δ: 2.08 (2H, tt, J=7 Hz, 8 Hz), 2.83 (2H, t, J=7 Hz), 3.35 (2H, t, J=8 Hz), 3.69 (2H, s), 6.7-6.8 (2H, m), 6.83 (1H, d, J=9 Hz), 7.0-7.1 (2H, m), 7.13 (1H, d, J=9 Hz), 8.97 (1H, s)

(2) 5-[4-[2-(3-Methoxyphenethyl)-1H-imidazol-1-yl]phenyl]-5,8,9,10-tetrahydroindeno[4,5-b][1,4]diazepine-2, 4(1H, 3H)-dione By using $N^1$-(4-nitro-2,3-dihydro-1H-inden-5-yl)benzene-1,4-diamine (200 mg, 0.74 mmol) obtained above, and 3-(3-methoxyphenyl)propionic acid (161 mg, 0.89 mmol), the title compound was obtained in the same manner as that of Example 3, (2), (4), (5), (6), Example 21, (1), (2), and (3).

$^1$H NMR (DMSO-d$_6$, 400 MHz) δ: 2.07 (2H, t, J=7 Hz), 2.8-2.9 (8H, m), 3.08 (1H, d, J=12 Hz), 3.63 (1H, d, J=12 Hz), 3.66 (3H, s), 6.6-6.7 (4H, m), 6.97 (1H, d, J=2 Hz), 7.01 (1H, d, J=8 Hz), 7.12 (1H, t, J=8 Hz), 7.28 (3H, t, J=8 Hz), 7.35 (2H, d, J=8 Hz), 10.24 (1H, s)

(3) 5-[4-[2-(3-Methoxyphenethyl)-1H-imidazol-1-yl]phenyl]-5,8,9,10-tetrahydroindeno[4,5-b][1,4]diazepine-2,4(1H,3H)-dione hydrochloride By using 5-[4-[2-(3-methoxyphenethyl)-1H-imidazol-1-yl]phenyl]-5,8,9,10-tetrahydroindeno[4,5-b][1,4]diazepine-2,4(1H,3H)-dione (13.2 mg, 0.027 mmol) obtained above, the title compound was obtained as yellow powder in the same manner as that of Example 3, (7).

$^1$H NMR (DMSO-d$_6$, 400 MHz) δ: 2.0-2.1 (2H, m), 2.8-3.0 (6H, m), 3.1-3.2 (3H, m), 3.66 (1H, d, J=12 Hz), 3.66 (31H, s), 6.54 (2H, d, J=7 Hz), 6.68 (1H, d, J=8 Hz), 6.76 (1H, dd, J=1 Hz, 7 Hz), 7.03 (1H, d, J=8 Hz), 7.14 (1H, t, J=8 Hz), 7.38 (2H, d, J=9 Hz), 7.44 (2H, d, J=9 Hz), 7.75 (1H, s), 7.85 (1H, s), 10.28 (1H, s)

Example 62

5-[4-[2-[2-(Thiophen-3-yl)ethyl]-1H-imidazol-1-yl]phenyl]-1H-naphtho[1,2-b][1,4]diazepine-2,4(3H,5H)-dione hydrochloride (1) 1-Nitro-N-[4-[2-[2-(thiophen-3-yl)ethyl]-1H-imidazol-1-yl]phenyl]naphthalen-2-amine By using $N^1$-(1-nitronaphthalen-2-yl)benzene-1,4-diamine obtained in Example 3, (1), and 3-(thiophen-3-yl)propionic acid, the title compound was obtained in the same manner as that of Example 3, (2), Example 21, (1), (2), and (3).

$^1$H NMR (CDCl$_3$, 400 MHz) δ: 2.95 (2H, t, J=8 Hz), 3.12 (2H, t, J=8 Hz), 6.79 (1H, d, J=5 Hz), 6.86 (1H, s), 6.98 (1H, s), 7.0-7.2 (4H, m), 7.30 (2H, d, J=9 Hz), 7.4-7.5 (2H, m), 7.66 (1H, t, J=7 Hz), 7.76 (1H, d, J=8 Hz), 7.83 (1H, d, J=8 Hz), 8.46 (1H, d, J=9 Hz), 9.26 (1H, s)

(2) $N^2$-[4-[2-[2-(Thiophen-3-yl)ethyl]-1H-imidazol-1-yl]phenyl]naphthalene-1,2-diamine To calcium chloride (44 mg, 0.40 mmol), and zinc (1.11 g, 17.04 mmol), ethanol (5.7 mL) and water (0.6 mL) were added, and to the resulting mixture, a solution of 1-nitro-N-[4-[2-[2-(thiophen-3-yl)ethyl]-1H-imidazol-1-yl]phenyl]naphthalen-2-amine (250 mg, 0.57 mmol) obtained above in ethanol was added dropwise with heating at 80° C. and stirring under a nitrogen atmosphere. After completion of the reaction was confirmed, the reaction mixture was filtered through Celite, the solvent was evaporated under reduced pressure, and then the residue was purified by silica gel column chromatography (chloroform/methanol=10/1) to obtain the title compound.

(3) 5-[4-[2-[2-(Thiophen-3-yl)ethyl]-1H-imidazol-1-yl]phenyl]-1H-naphtho[1,2-b][1,4]diazepine-2,4(3H, 5H)-dione By using $N^2$-[4-[2-[2-(thiophen-3-yl)ethyl]-1H-imidazol-1-yl]phenyl]naphthalene-1,2-diamine obtained above, the title compound was obtained in the same manner as that of Example 3, (5), and Example 3, (6).

$^1$H NMR (DMSO-d$_6$, 400 MHz) δ: 2.93 (4H, s), 3.18 (1H, d, J=12 Hz), 3.75 (1H, d, J=12 Hz), 6.83 (1H, d, J=5 Hz), 6.99 (1H, d, J=1 Hz), 7.03 (1H, d, J=9 Hz), 7.06 (1H, s), 7.33 (1H, d, J=1 Hz), 7.3-7.4 (5H, m), 7.61 (1H, t, J=7 Hz), 7.68 (1H, t, J=8 Hz), 7.74 (1H, d, J=9 Hz), 7.94 (1H, d, J=8 Hz), 8.28 (1H, d, J=8 Hz), 10.96 (1H, s)

(4) 5-[4-[2-[2-(Thiophen-3-yl)ethyl]-1H-imidazol-1-yl]phenyl]-1H-naphtho[1,2-b][1,4]diazepine-2,4(3H, 5H)-dione hydrochloride By using 5-[4-[2-[2-(thiophen-3-yl)ethyl]-1H-imidazol-1-yl]phenyl]-1H-naphtho[1,2-b][1,4]diazepine-2,4(3H,5H)-dione obtained above, the title compound was obtained as a slightly brown amorphous substance in the same manner as that of Example 3, (7).

$^1$H NMR (DMSO-d$_6$, 400 MHz) δ: 2.96 (2H, t, J=8 Hz), 3.19 (2H, t, J=8 Hz), 3.20 (1H, d, J=12 Hz), 3.78 (1H, d, J=12 Hz), 6.79 (1H, dd, J=1 Hz, 5 Hz), 7.01 (1H, d, J=9 Hz), 7.07 (1H, d, J=2 Hz), 7.42 (1H, dd, J=3 Hz, 5 Hz), 7.48 (2H, d, J=9 Hz), 7.53 (2H, d, J=9 Hz), 7.63 (1H, t, J=7 Hz), 7.70

(1H, t, J=7 Hz), 7.71 (1H, d, J=9 Hz), 7.78 (1H, s), 7.90 (1H, s), 7.95 (1H, d, J=8 Hz), 8.30 (1H, d, J=8 Hz), 10.98 (1H, s)

Example 63

5-[4-[1-(2-Aminobenzyl)-1H-imidazol-2-yl]phenyl]-1H-naphtho[1,2-b][1,4]diazepine-2,4(3H,5H)-dione By using 2-(4-nitrophenyl)-1H-imidazole [Heterocycles, 76, 507 (2008)], and t-butyl [2-(bromoethyl)phenyl]carbamate, a crude product of t-butyl [2-[2-[4-(2,4-dioxo-3,4-dihydro-1H-naphtho[2,1-b][1,4]diazepin-5(2H)-yl)phenyl]-1H-imidazol-1-yl]methyl]phenyl]carbamate was obtained in the same manner as that of Example 23, (1), (2), (3), (4), and (5). This crude product was treated with trifluoroacetic acid in dichloromethane, then subjected to post treatments in a conventional manner, and purified by silica gel column chromatography to obtain the title compound (44 mg) as a brown amorphous substance.

$^1$H NMR (CDCl$_3$, 400 MHz) δ: 3.51 (2H, s), 3.59 (1H, d, J=13 Hz), 3.62 (1H, d, J=12 Hz), 5.07 (2H, s), 6.69 (1H, d, J=8 Hz), 6.75 (1H, t, J=8 Hz), 6.84 (1H, d, J=7 Hz), 6.94 (1H, s), 6.98 (1H, d, J=9 Hz), 7.13 (1H, t, J=8 Hz), 7.18 (1H, d, J=1 Hz), 7.30 (2H, d, J=9 Hz), 7.58 (2H, d, J=9 Hz), 7.61 (2H, d, J=9 Hz), 7.68 (1H, t, J=8 Hz), 7.84 (1H, d, J=8 Hz), 8.17 (1H, d, J=9 Hz), 9.47 (1H, s)

Example 64

5-[3-Methoxy-4-(1-phenethyl-1H-imidazol-2-yl)-phenyl]-1H-naphtho[1,2-b][1,4]diazepine-2,4(3H,5H)-dione By using 2-(2-methoxy-4-nitrophenyl)-1H-imidazole synthesized with reference to information described in a publication [Heterocycles, 76, 507 (2008)], the title compound (52 mg) was obtained as white powder in the same manner as that of Example 23, (1), (2), (3), (4), and (5).

$^1$H NMR (CDCl$_3$, 400 MHz) δ: 2.94 (2H, t, J=7 Hz), 3.63 (2H, s), 3.73 (3H, s), 4.05 (2H, t, J=7 Hz), 6.79 (1H, d, J=8 Hz), 6.9-7.0 (4H, m), 7.06 (1H, d, J=9 Hz), 7.1-7.3 (5H, m), 7.6-7.7 (2H, m), 7.71 (1H, t, J=7 Hz), 7.89 (1H, d, J=8 Hz), 8.08 (1H, d, J=8 Hz), 8.46 (1H, s)

Example 65

5-[3-Hydroxy-4-(1-phenethyl-1H-imidazol-2-yl)-phenyl]-1H-naphtho[1,2-b][1,4]diazepine-2,4(3H,5H)-dione By using 5-[3-methoxy-4-(1-phenethyl-1H-imidazol-2-yl)-phenyl]-1H-naphtho[1,2-b][1,4]diazepine-2,4(3H,5H)-dione (47 mg, 0.094 mmol) obtained in Example 64, the title compound (20 mg, yield 43%) was obtained as a pale red amorphous substance in the same manner as that of Example 2.

$^1$H NMR (CDCl$_3$, 400 MHz) δ: 3.16 (2H, t, J=7 Hz), 3.61 (2H, s), 4.55 (2H, t, J=7 Hz), 6.78 (1H, d, J=1 Hz), 6.87 (1H, dd, J=2 Hz, 9 Hz), 6.93 (1H, d, J=2 Hz), 7.05 (1H, d, J=1 Hz), 7.1-7.2 (3H, m), 7.2-7.3 (3H, m), 7.47 (1H, d, J=8 Hz), 7.6-7.6 (2H, m), 7.70 (1H, t, J=8 Hz), 7.86 (1H, d, J=8 Hz), 8.09 (1H, d, J=8 Hz), 8.58 (1H, s)

Example 66

5-[4-[2-[2-(Furan-2-yl)ethyl]-H-imidazol-1-yl]-phenyl]-1H-naphtho[1,2-b][1,4]diazepine-2,4(3H,5H)-dione hydrochloride By using N$^1$-(1-nitronaphthalen-2-yl)benzene-1,4-diamine obtained in Example 3, (1), and 3-(furan-2-yl)propionic acid, the title compound (23 mg) was obtained as a purple amorphous substance in the same manner as that of Example 3, (2), (4), (5), (6), Example 21, (1), (2), and (3).

$^1$H NMR (DMSO-d$_6$, 400 MHz) δ: 3.0-3.1 (2H, m), 3.1-3.2 (3H, m), 3.77 (1H, d, J=12 Hz), 6.04 (1H, d, J=2 Hz), 6.30 (1H, dd, J=2 Hz, 3 Hz), 6.99 (1H, d, J=9 Hz), 7.46 (1H, d, J=1 Hz), 7.49 (2H, d, J=9 Hz), 7.56 (2H, d, J=9 Hz), 7.62 (1H, t, J=7 Hz), 7.69 (1H, dt, J=1 Hz, 8 Hz), 7.75 (1H, d, J=9 Hz), 7.82 (1H, s), 7.93 (1H, d, J=2 Hz), 7.94 (1H, d, J=9 Hz), 8.29 (1H, d, J=9 Hz), 10.98 (1H, s)

Example 67

5-[4-[2-(2-Fluorophenethyl)-1H-imidazol-1-yl]phenyl]-5,8,9,10-tetrahydroindeno[4,5-b][1,4]diazepine-2,4(1H,3H)-dione By using N$^1$-(4-nitro-2,3-dihydro-1H-inden-5-yl)benzene-1,4-diamine obtained in Example 61, (1), and 3-(2-fluorophenyl)propionic acid, the title compound (3.8 mg) was obtained as pale yellow oil in the same manner as that of Example 3, (2), (4), (5), (6), Example 21, (1), (2), and (3).

$^1$H NMR (CDCl$_3$, 400 MHz) δ: 2.1-2.3 (2H, m), 2.9-3.1 (8H, m), 3.5-3.6 (2H, m), 6.76 (1H, d, J=8 Hz), 6.9-7.2 (9H, m), 7.2-7.3 (2H, m), 8.09 (1H, s)

Example 68

5-[4-[2-(Phenoxymethyl)-1H-imidazol-1-yl]phenyl]-1H-naphtho[1,2-b][1,4]diazepine-2,4(3H,5H)-dione By using N$^1$-(1-nitronaphthalen-2-yl)benzene-1,4-diamine (200 mg, 0.72 mol) obtained in Example 3, (1), and 2-phenoxyacetic acid (131 mg, 0.86 mmol), the title compound was obtained as white crystals in the same manner as that of Example 3, (2), (4), (5), (6), Example 21, (1), (2), and (3).

$^1$H NMR (CDCl$_3$, 400 MHz) δ: 3.62 (2H, s), 5.05 (2H, d, J=3 Hz), 6.95 (2H, d, J=8 Hz), 6.98 (2H, d, J=9 Hz), 7.19 (2H, dd, J=1 Hz, 9 Hz), 7.2-7.3 (2H, m), 7.36 (2H, d, J=9 Hz), 7.51 (2H, d, J=9 Hz), 7.61 (1H, d, J=9 Hz), 7.63 (1H, t, J=7 Hz), 7.71 (1H, t, J=7 Hz), 7.88 (1H, d, J=8 Hz), 8.07 (1H, d, J=9 Hz), 8.41 (1H, s)

Example 69

5-[4-[5-[2-Methyl-2-(pyridin-2-yl)propyl]-1H-tetrazol-1-yl]phenyl]-1H-naphtho[1,2-b][1,4]diazepine-2,4(3H,5H)-dione hydrochloride (1) 5-[4-[5-[2-Methyl-2-(pyridin-2-yl)propyl]-1H-tetrazol-1-yl]phenyl]-1H-naphtho[1,2-b][1,4]diazepine-2,4(3H,5H)-dione By using N$^1$-(1-nitronaphthalen-2-yl)benzene-1,4-diamine (138 mg, 0.50 mol) obtained in Example 3, (1), and 3-methyl-3-(pyridin-2-yl)butyric acid (80 mg, 0.45 mmol), the title compound was obtained in the same manner as that of Example 3, (2), (3), (4), (5), and (6).

¹H NMR (CDCl₃, 400 MHz) δ: 1.54 (6H, s), 3.39 (1H, d, J=15 Hz), 3.47 (1H, d, J=15 Hz), 3.66 (1H, d, J=12 Hz), 3.70 (1H, d, J=12 Hz), 7.0-7.1 (2H, m), 7.17 (1H, d, J=8 Hz), 7.32 (2H, d, J=8 Hz), 7.45 (2H, d, J=9 Hz), 7.52 (1H, t, J=8 Hz), 7.6-7.7 (2H, m), 7.74 (1H, t, J=8 Hz), 7.89 (1H, d, J=8 Hz), 8.2-8.3 (1H, m), 8.27 (1H, d, J=4 Hz), 9.4-9.7 (1H, br s)

(2) 5-[4-[5-[2-Methyl-2-(pyridin-2-yl)propyl]-1H-tetrazol-1-yl]phenyl]-1H-naphtho[1,2-b][1,4]diazepine-2,4(3H,5H)-dione hydrochloride By using 5-[4-[5-[2-methyl-2-(pyridin-2-yl)propyl]-1H-tetrazol-1-yl]phenyl]-1H-naphtho[1,2-b][1,4]diazepine-2,4(3H,5H)-dione (30 mg, 0.06 mmol) obtained above, the title compound (29 mg, yield 90%) was obtained as pale yellow powder in the same manner as that of Example 3, (7).

¹H NMR (DMSO-d₆, 400 MHz) δ: 1.50 (6H, s), 2.50 (2H, s), 3.22 (1H, d, J=12 Hz), 3.80 (1H, d, J=12 Hz), 7.07 (1H, d, J=9 Hz), 7.49 (3H, d, J=8 Hz), 7.6-7.7 (4H, m), 7.70 (1H, t, J=8 Hz), 7.78 (1H, d, J=9 Hz), 7.9-8.1 (2H, d, J=8 Hz), 8.31 (1H, d, J=8 Hz), 8.48 (1H, s), 11.00 (1H, s)

Example 70

5-[4-[5-[2-(3-Methoxypyridin-2-yl)ethyl]-1H-tetrazol-1-yl]phenyl]-1H-naphtho[1,2-b][1,4]diazepine-2,4(3H,5H)-dione hydrochloride (1) 5-[4-[5-[2-(3-Methoxypyridin-2-yl)ethyl]-1H-tetrazol-1-yl]phenyl]-1H-naphtho[1,2-b][1,4]diazepine-2,4(3H,5H)-dione By using N¹-(1-nitronaphthalen-2-yl)benzene-1,4-diamine (150 mg, 0.54 mol) obtained in Example 3, (1), and 3-(3-methoxypyridin-2-yl)propionic acid (98 mg, 0.54 mmol), the title compound was obtained in the same manner as that of Example 3, (2), (3), (4), (5), and (6).

¹H NMR (CDCl₃, 400 MHz) δ: 3.3-3.4 (4H, m), 3.64 (1H, d, J=12 Hz), 3.68 (1H, d, J=12 Hz), 3.78 (3H, s), 7.0-7.1 (3H, m), 7.49 (2H, d, J=9 Hz), 7.57 (2H, d, J=9 Hz), 7.6-7.7 (2H, m), 7.73 (1H, t, J=7 Hz), 7.89 (1H, d, J=8 Hz), 7.97 (1H, d, J=4 Hz), 8.1-8.2 (1H, m), 8.9-9.1 (1H, br s)

(2) 5-[4-[5-[2-(3-Methoxypyridin-2-yl)ethyl]-1H-tetrazol-1-yl]phenyl]-1H-naphtho[1,2-b][1,4]diazepine-2,4(3H,5H)-dione hydrochloride By using 5-[4-[5-[2-(3-methoxypyridin-2-yl)ethyl]-1H-tetrazol-1-yl]phenyl]-1H-naphtho[1,2-b][1,4]diazepine-2,4(3H,5H)-dione (20 mg, 0.04 mmol) obtained above, the title compound (21 mg, yield 97%) was obtained as yellow crystals in the same manner as that of Example 3, (7).

¹H NMR (DMSO-d₆, 400 MHz) δ: 3.20 (1H, d, J=12 Hz), 3.36 (4H, q, J=5 Hz), 3.78 (1H, d, J=12 Hz), 3.85 (3H, s), 7.05 (1H, d, J=9 Hz), 7.51 (2H, d, J=9 Hz), 7.60 (1H, s), 7.61 (1H, t, J=8 Hz), 7.69 (1H, t, J=8 Hz), 7.75 (4H, d, J=8 Hz), 7.94 (1H, d, J=8 Hz), 8.16 (1H, d, J=5 Hz), 8.29 (1H, d, J=8 Hz), 10.98 (1H, s)

Example 71

5-[4-[[2-(Pyridin-2-yl)ethyl]-1H-imidazol-1-yl]phenyl]-1H-naphtho[1,2-b][1,4]diazepine-2,4(3H,5H)-dione dihydrochloride (1) 5-[4-[[2-(Pyridin-2-yl)ethyl]-1H-imidazol-1-yl]phenyl]-1H-naphtho[1,2-b][1,4]diazepine-2,4(3H,5H)-dione By using N¹-(1-nitronaphthalen-2-yl)benzene-1,4-diamine (200 mg, 0.71 mol) obtained in Example 3, (1), and 3-(pyridin-2-yl)propionic acid (119 mg, 0.79 mmol), the title compound was obtained in the same manner as that of Example 3, (2), (4), (5), (6), Example 21, (1), (2), and (3).

¹H NMR (CDCl₃, 400 MHz) δ: 3.13 (2H, t, J=8 Hz), 3.29 (2H, t, J=8 Hz), 3.64 (2H, s), 6.97 (1H, s), 7.1-7.2 (4H, m), 7.21 (2H, d, J=8 Hz), 7.36 (2H, d, J=9 Hz), 7.53 (1H, t, J=7 Hz), 7.6-7.8 (3H, m), 7.88 (1H, d, J=8 Hz), 8.19 (1H, d, J=7 Hz), 8.45 (1H, d, J=4 Hz), 9.3-9.5 (1H, br s)

(2) 5-[4-[[(Pyridin-2-yl)ethyl]-1H-imidazol-1-yl]phenyl]-1H-naphtho[1,2-b][1,4]diazepine-2,4(3H,5H)-dione dihydrochloride By using 5-[4-[[(pyridin-2-yl)ethyl]-1H-imidazol-1-yl]phenyl]-1H-naphtho[1,2-b][1,4]diazepine-2,4(3H,5H)-dione (20 mg, 0.042 mmol) obtained above, the title compound (17 mg, yield 74%) was obtained as slightly brown crystals in the same manner as that of Example 3, (7).

¹H NMR (DMSO-d₆, 400 MHz) δ: 3.20 (1H, d, J=12 Hz), 3.3-3.4 (4H, m), 3.78 (1H, d, J=12 Hz), 7.03 (1H, d, J=9 Hz), 7.49 (4H, d, J=9 Hz), 7.6-7.7 (3H, m), 7.70 (1H, t, J=8 Hz), 7.76 (1H, d, J=9 Hz), 7.83 (1H, d, J=2 Hz), 7.93 (1H, d, J=12 Hz), 7.96 (1H, d, J=8 Hz), 8.04 (1H, s), 8.30 (1H, d, J=8 Hz), 8.55 (1H, s), 10.99 (1H, s)

Example 72

5-[4-(5-Phenyl-1H-imidazol-4-yl)phenyl]-1H-naphtho[1,2-b][1,4]diazepine-2,4(3H,5H)-dione hydrochloride (1) 1-Nitro-N-[4-(phenylethenyl)phenyl]naphthalen-2-amine 1-Nitro-2-naphthyl trifluoromethanesulfonate (733 mg, 2.28 mmol), 4-(phenylethynyl)aniline (440 mg, 2.28 mmol), palladium(II) acetate (51 mg, 0.028 mmol), 4,5-bis(diphenylphosphino)-9,9-dimethylxanthene triphenylphosphine (264 mg, 0.456 mmol), and potassium carbonate (473 mg, 3.42 mmol) were dissolved in dry toluene (10 mL), and the solution was refluxed by heating for 16 hours under a nitrogen atmosphere. The reaction mixture was left to cool, and then the insoluble matter was separated by filtration, and washed away with ethyl acetate. The organic layer was washed with saturated aqueous sodium hydrogencarbonate, and dried over anhydrous sodium sulfate. The solvent was evaporated under reduced pressure, and the residue was purified by silica gel column chromatography (hexane/ethyl acetate=4/1) to obtain the title compound (830 mg, yield 100%).

¹H NMR (CDCl₃, 400 MHz) δ: 7.2-7.3 (2H, m), 7.3-7.4 (3H, m), 7.43 (2H, d, J=8 Hz), 7.5-7.6 (4H, m), 7.64 (1H, t, J=9 Hz), 7.74 (1H, d, J=8 Hz), 7.80 (1H, d, J=9 Hz), 8.48 (1H, d, J=9 Hz), 9.37 (1H, s)

(2) 5-[4-(Phenylethynyl)-1,5-dihydro-2H-naphtho[1,2-b][1,4]diazepine-2,4(3H)-dione 1-Nitro-N-[4-(phenylethynyl)phenyl]naphthalen-2-amine (830 mg, 2.28 mmol) obtained above was dissolved in ethanol (22 mL) and water (3 mL), zinc powder (4.47 g, 68.4 mmol), and calcium chloride (361 mg, 1.6 mmol) were added to the solution, and the mixture was refluxed by heating for 2 hours under a nitrogen atmosphere. The reaction mixture was left to cool, and then the insoluble matter was separated by filtration, and washed away with ethanol. The organic layer was evaporated to obtain N²-[4-

(phenylethynyl)benzyl]naphthalene-1,2-diamine as a crude product. The resulting crude product was purified in the same manner as that of Example 3, (5), and (6) to obtain the title compound (700 mg, 76%).

$^1$H NMR (CDCl$_3$, 400 MHz) δ: 3.62 (2H, s), 7.01 (1H, d, J=9 Hz), 7.26 (2H, d, J=8 Hz), 7.3-7.4 (3H, m), 7.5-7.7 (6H, m), 7.70 (1H, t, J=8 Hz), 7.86 (1H, d, J=8 Hz), 8.15 (1H, d, J=8 Hz), 9.18 (1H, s)

(3) 5-[4-(2-Oxo-2-phenylacetyl)phenyl]-1,5-dihydro-2H-naphtho[1,2-b][1,4]diazepine-2,4(3H)-dione 5-[4-(Phenylethynyl)-1,5-dihydro-2H-naphtho[1,2-b][1,4]diazepine-2,4(3H)-dione (100 mg, 0.25 mmol) obtained above was dissolved in acetone (3 mL), and 0.22% aqueous sodium hydrogencarbonate (1.7 mL), and 2.2% aqueous magnesium sulfate (1.7 mmol) were added to the solution. Potassium permanganate (99 mg, 0.63 mmol) was further added to the mixture, and the resulting mixture was stirred at room temperature for 16 hours under a nitrogen atmosphere. The reaction mixture was left to cool, and then the insoluble matter was separated by filtration, and washed away with ethyl acetate. The organic layer was washed with saturated aqueous sodium hydrogencarbonate, and dried over anhydrous sodium sulfate. The solvent was evaporated under reduced pressure, and the residue was purified by silica gel column chromatography (hexane/ethyl acetate=20/1) to obtain the title compound (37 mg, yield 34%).

$^1$H NMR (CDCl$_3$, 400 MHz) δ: 3.62 (2H, s), 7.01 (1H, d, J=9 Hz), 7.2-7.3 (2H, m), 7.3-7.4 (3H, m), 7.5-7.7 (6H, m), 7.71 (1H, t, J=7 Hz), 7.87 (1H, d, J=8 Hz), 8.10 (1H, d, J=9 Hz), 8.67 (1H, s)

(4) 5-[4-(5-Phenyl-1H-imidazol-4-yl)phenyl]-1H-naphtho[1,2-b][1,4]diazepine-2,4(3H,5H)-dione 5-[4-(2-Oxo-2-phenylacetyl)phenyl]-1,5-dihydro-2H-naphtho[1,2-b][1,4]diazepine-2,4(3H)-dione (37 mg, 0.085 mmol) obtained above was dissolved in acetic acid (2 mL), ammonium acetate (131 mg, 1.7 mmol), and paraformaldehyde (5 mg, 0.17 mmol) were added to the solution, and the mixture was stirred at room temperature for 12 hours under a nitrogen atmosphere. The reaction mixture was left to cool, and then evaporated, and the residue was neutralized with aqueous potassium carbonate. The aqueous layer was extracted with chloroform, and the organic layer was dried over sodium sulfate. The solvent was evaporated under reduced pressure, and the residue was purified by silica gel column chromatography (chloroform/methanol=20/1) to obtain the title compound (15 mg, yield 40%).

$^1$H NMR (CDCl$_3$, 400 MHz) δ: 3.58 (2H, s), 6.6-6.8 (3H, m), 6.82 (1H, t, J=7 Hz), 6.97 (1H, d, J=1 Hz), 7.1-7.4 (6H, m), 7.6-7.7 (2H, m), 7.69 (1H, dt, J=1 Hz, 7 Hz), 7.88 (1H, d, J=7 Hz), 8.13 (1H, d, J=8 Hz), 9.07 (1H, s)

(5) 5-[4-(5-Phenyl-1H-imidazol-4-yl)phenyl]-1H-naphtho[1,2-b][1,4]diazepine-2,4(3H,5H)-dione hydrochloride By using 5-[4-(5-phenyl-1H-imidazol-4-yl)phenyl]-1H-naphtho[1,2-b][1,4]diazepine-2,4(3H,5H)-dione obtained above, the title compound (12 mg, yield 74%) was obtained in the same manner as that of Example 3, (7).

$^1$H NMR (DMSO-d$_6$, 400 MHz) δ: 3.17 (1H, d, J=12 Hz), 3.74 (1H, d, J=12 Hz), 6.99 (1H, d, J=9 Hz), 7.35 (2H, d, J=8 Hz), 7.4-7.5 (5H, m), 7.56 (2H, d, J=8 Hz), 7.61 (1H, t, J=7 Hz), 7.68 (1H, t, J=7 Hz), 7.74 (1H, d, J=9 Hz), 7.93 (1H, d, J=8 Hz), 8.28 (1H, d, J=8 Hz), 9.23 (1H, s), 10.95 (1H, s)

Example 73

5-[4-[(5-Phenylethyl)-1H-imidazol-4-yl]phenyl]-1H-naphtho[1,2-b][1,4]diazepine-2,4(3H,5H)-dione hydrochloride

(1) 4-(4-Phenylbut-1-yn-1-yl)aniline

4-Iodoaniline (0.5 g, 2.28 mmol), 3-butynylbenzene (0.64 ml, 4.56 mmol), bis(triphenylphosphine)palladium(II) dichloride (80 mg, 0.11 mmol), copper(I) iodide (87 mg, 0.46 mmol), and diisopropylethylamine (1.57 mL, 9.12 mmol) were dissolved in dimethylformamide (10 mL), and the solution was refluxed by heating for 16 hours under a nitrogen atmosphere. The reaction mixture was left to cool, and then the insoluble matter was separated by filtration, and washed away with ethyl acetate. The organic layer was washed with saturated aqueous sodium hydrogencarbonate, and dried over anhydrous sodium sulfate. The solvent was evaporated under reduced pressure, and the residue was purified by silica gel column chromatography (hexane/ethyl acetate=10/1) to obtain the title compound (504 mg, yield 100%).

$^1$H NMR (CDCl$_3$, 400 MHz) δ: 2.66 (2H, t, J=7 Hz), 2.90 (2H, t, J=7 Hz), 3.72 (2H, s), 6.57 (2H, d, J=8 Hz), 7.18 (2H, d, J=8 Hz), 7.22 (1H, d, J=7 Hz), 7.2-7.3 (4H, m)

(2) 5-[4-[(5-Phenylethyl)-1H-imidazol-4-yl]phenyl]-1H-naphtho[1,2-b][1,4]diazepine-2,4(3H,5H)-dione By using 1-nitro-2-naphthyl trifluoromethanesulfonate (733 mg, 2.28 mmol), and 4-(4-phenylbut-1-yn-1-yl)aniline (504 mg, 2.28 mmol) obtained above, the title compound (15 mg) was obtained in the same manner as that of Example 72.

$^1$H NMR (CDCl$_3$, 400 MHz) δ: 1.76 (4H, s), 4.81 (1H, d, J=15 Hz), 4.87 (1H, d, J=15 Hz), 6.6-6.7 (3H, m), 6.75 (1H, d, J=2 Hz), 6.92 (1H, d, J=2 Hz), 7.03 (2H, d, J=9 Hz), 7.1-7.3 (3H, m), 7.49 (2H, d, J=7 Hz), 7.6-7.7 (2H, m), 7.70 (1H, t, J=7 Hz), 7.89 (1H, d, J=8 Hz), 8.13 (1H, d, J=8 Hz), 8.95 (1H, s)

(3) 5-[4-[(5-Phenylethyl)-1H-imidazol-4-yl]phenyl]-1H-naphtho[1,2-b][1,4]diazepine-2,4(3H,5H)-dione hydrochloride By using 5-[4-[(5-phenylethyl)-1H-imidazol-4-yl]phenyl]-1H-naphtho[1,2-b][1,4]diazepine-2,4(3H,5H)-dione (15 mg, 0.032 mmol) obtained above, the title compound (14 mg, yield 86%) was obtained as yellow powder in the same manner as that of Example 3, (7).

$^1$H NMR (DMSO-d$_6$, 400 MHz) δ: 2.98 (2H, t, J=7 Hz), 3.08 (2H, t, J=7 Hz), 3.18 (1H, d, J=11 Hz), 3.75 (1H, d, J=12 Hz), 6.98 (1H, d, J=9 Hz), 7.14 (2H, d, J=7 Hz), 7.18 (1H, d, J=7 Hz), 7.25 (2H, t, J=7 Hz), 7.36 (2H, d, J=8 Hz), 7.46 (2H, d, J=8 Hz), 7.62 (1H, t, J=7 Hz), 7.69 (1H, t, J=7 Hz), 7.74 (1H, d, J=9 Hz), 7.94 (1H, d, J=8 Hz), 8.29 (1H, d, J=8 Hz), 9.19 (1H, s), 10.96 (1H, s), 14.68 (1H, s)

Example 74

5-[4-(4,4-Dimethyl-2-phenethyl-4,5-dihydro 1H-imidazol-1-yl)phenyl]-1H-naphtho[1,2-b][1,4] diazepine-2,4(3H,5H)-dione hydrochloride

(1) 2-Methyl-N$^1$-(4-nitrophenyl)propane-1,2-diamine

4-Fluoronitrobenzene (0.5 mL, 4.69 mmol), and 2-methylpropane-1,2-diamine (0.59 mL, 5.63 mmol) were dissolved in dimethylformamide (10 mL), potassium carbonate (1.94 g, 14.1 mmol) was added to the solution, and the mixture was refluxed by heating for 16 hours under a nitrogen atmosphere. The reaction mixture was left to cool, and then diluted with ethyl acetate, and the organic layer was washed with water and saturated brine. The organic layer was dried over sodium sulfate, then the solvent was evaporated under reduced pressure, and the residue was purified by silica gel column chromatography (chloroform/methanol=20/1) to obtain the title compound (0.98 g, yield 100%).

$^1$H NMR (CDCl$_3$, 400 MHz) δ: 1.1-1.4 (2H, m), 1.22 (6H, s), 3.03 (2H, d, J=5 Hz), 5.24 (1H, s), 6.55 (2H, d, J=9 Hz), 8.08 (2H, d, J=9 Hz)

(2) 4,4-Dimethyl-1-(4-nitrophenyl)-2-phenethyl-4,5-dihydro-1H-imidazole

By using 2-methyl-N$^1$-(4-nitrophenyl)propane-1,2-diamine (0.98 g, 4.69 mmol) obtained above, and 3-phenylpropionic acid (0.948 g, 6.31 mmol), a crude product of N-[2-methyl-1-[(4-nitrophenyl)amino]propan-2-yl]-3-phenylpropanamide was obtained in the same manner as that of Example 3, (2). The resulting crude product was dissolved in acetonitrile (100 mL), phosphorus(V) oxychloride (15.7 mL, 168.3 mmol) was added to the solution, and the mixture was refluxed by heating for 16 hours under a nitrogen atmosphere. The reaction mixture was left to cool, and then evaporated, and the residue was diluted with ethyl acetate. The organic layer was washed with aqueous sodium hydrogencarbonate, water, and saturated brine, and dried over sodium sulfate. The solvent was evaporated under reduced pressure, and the residue was purified by silica gel column chromatography (hexane/ethyl acetate=10/1) to obtain the title compound (1.51 g, yield 100%).

$^1$H NMR (CDCl$_3$, 400 MHz) δ: 1.32 (6H, s), 2.82 (2H, t, J=8 Hz), 2.99 (2H, t, J=7 Hz), 3.58 (2H, s), 6.97 (2H, d, J=9 Hz), 7.15 (2H, d, J=7 Hz), 7.21 (1H, d, J=7 Hz), 7.2-7.3 (2H, m), 8.16 (2H, d, J=9 Hz)

(3) N-[4-(4,4-Dimethyl-2-phenethyl-4,5-dihydro-1H-imidazol-1-yl)phenyl]-1-nitronaphthalen-2-amine 4,4-Dimethyl-1-(4-nitrophenyl)-2-phenethyl-4,5-dihydro-1H-imidazole (1.51 g, 4.69 mmol) obtained above was dissolved in methanol (50 mL), after the atmosphere was substituted with nitrogen, 10% Pd—C(200 mg) was added to the solution, and the resulting mixture was stirred at room temperature for 2 hours under a hydrogen atmosphere. The insoluble matter was separated by filtration, and washed with ethyl acetate. The organic layer was washed with saturated aqueous sodium hydrogencarbonate, and dried over anhydrous sodium sulfate. The solvent was evaporated under reduced pressure to obtain a crude product of 4-(4,4-dimethyl-2-phenethyl-4,5-dihydro-1H-imidazol-1-yl)aniline. By using the resulting crude product (321 mg), and 1-nitro-2-naphthyl trifluoromethanesulfonate (293 mg, 1 mmol), the title compound (465 mg, yield 1.00%) was obtained in the same manner as that of Example 73, (1).

$^1$H NMR (CDCl$_3$, 400 MHz): δ: 1.33 (6H, s), 2.62 (2H, t, J=8 Hz), 2.94 (2H, t, J=7 Hz), 3.54 (2H, s), 7.03 (2H, d, J=9 Hz), 7.1-7.2 (2H, m), 7.2-7.3 (6H, m), 7.39 (1H, dt, J=1 Hz, 8 Hz), 7.63 (1H, dt, J=1 Hz, 7 Hz), 7.71 (1H, d, J=8 Hz), 7.75 (1H, d, J=9 Hz), 8.57 (1H, d, J=9 Hz), 9.55 (1H, s)

(4) 5-[4-(4,4-Dimethyl-2-phenethyl-4,5-dihydro-1H-imidazol-1-yl)phenyl]-1H-naphtho[1,2-b][1,4]diazepine-2,4(3H,5H)-dione By using N-[4-(4,4-dimethyl-2-phenethyl-4, 5-dihydro-1H-imidazol-1-yl)phenyl]-1-nitronaphthalen-2-amine (465 mg, 1 mmol) obtained above, the title compound (50 mg, 17%) was obtained in the same manner as that of Example 74, (3), Example 3, (5), and (6).

$^1$H NMR (CDCl$_3$, 400 MHz) δ: 1.31 (6H, s), 2.65 (2H, t, J=8 Hz), 2.92 (2H, t, J=9 Hz), 3.53 (2H, s), 3.61 (2H, s), 7.0-7.1 (3H, m), 7.1-7.3 (7H, m), 7.61 (2H, d, J=9 Hz), 7.70 (1H, t, J=8 Hz), 7.85 (1H, d, J=8 Hz), 8.16 (1H, d, J=8 Hz), 9.20 (1H, s)

(5) 5-[4-(4,4-Dimethyl-2-phenethyl-4, 5-dihydro-1H-imidazol-1-yl)phenyl]-1H-naphtho[1,2-b][1,4] diazepine-2,4(3H,5H)-dione hydrochloride By using 5-[4-(4,4-dimethyl-2-phenethyl-4,5-dihydro-1H-imidazol-1-yl)phenyl]-1H-naphtho[1,2-b][1,4]diazepine-2,4(3H,5H)-dione (50 mg, 0.1 mmol) obtained above, the title compound (47 mg, yield 88%) was obtained in the same manner as that of Example 3, (7).

$^1$H NMR (DMSO-d$_6$, 400 MHz) δ: 1.42 (6H, s), 2.85 (4H, s), 3.18 (1H, d, J=12 Hz), 3.75 (1H, d, J=12 Hz), 4.06 (2H, s), 6.98 (1H, d, J=9 Hz), 7.12 (2H, d, J=7 Hz), 7.2-7.3 (3H, m), 7.38 (2H, d, J=9 Hz), 7.50 (2H, d, J=9 Hz), 7.6-7.8 (3H, m), 7.95 (1H, d, J=8 Hz), 8.29 (1H, d, J=9 Hz), 10.96 (1H, s), 11.25 (1H, s)

Example 75

5-[4-[2-[(2-Methoxyphenyl)amino]-1H-imidazol-1-yl]phenyl]-1H-naphtho[1,2-b][1,4]diazepine-2,4(3H, 5H)-dione

(1) 2-Bromo-1-(4-nitrophenyl)-1H-imidazole

1-Fluoro-4-nitrobenzene (0.36 mL, 3.4 mmol), 2-bromoimidazole (0.5 g, 3.4 mmol), and potassium carbonate (1.46 g, 10.2 mmol) were dissolved in dimethylformamide (10 mL), and the solution was heated at 110° C. for 16 hours under a nitrogen atmosphere. The reaction mixture was left to cool, and then evaporated, and the residue was diluted with ethyl acetate. The organic layer was washed with aqueous sodium hydrogencarbonate, water, and saturated brine, and dried over sodium sulfate. The solvent was evaporated under reduced pressure, and the residue was purified by silica gel column chromatography (chloroform/methanol=20/1) to obtain the title compound (0.8 g, yield 88%).

$^1$H NMR (CDCl$_3$, 400 MHz) δ: 7.20 (2H, d, J=2 Hz), 7.61 (2H, d, J=9 Hz), 8.40 (2H, d, J=9 Hz)

(2) N-(2-Methoxyphenyl)-1-(4-nitrophenyl)-1H-imidazol-2-amine

2-Bromo-1-(4-nitrophenyl)-1H-imidazole (0.1 g, 0.37 mmol) obtained above, o-anisidine (62 μL, 0.56 mmol), and p-toluenesulfonic acid (0.14 g, 0.74 mmol) were dissolved in toluene (4 mL), and the solution was refluxed by heating for 16 hours under a nitrogen atmosphere. The reaction mixture was left to cool, and then evaporated, and the residue was diluted with ethyl acetate. The organic layer was washed with aqueous sodium hydrogencarbonate, water, and saturated brine, and dried over sodium sulfate. The solvent was evaporated under reduced pressure, and the residue was purified by silica gel column chromatography (chloroform/methanol=20/1) to obtain the title compound (95 mg, yield 83%).

$^1$H NMR (CDCl$_3$, 400 MHz) δ: 3.82 (3H, s), 6.76 (1H, s), 6.84 (1H, dd, J=2 Hz, 8 Hz), 6.8-6.9 (2H, m), 6.96 (1H, dt, J=2 Hz, 8 Hz), 7.02 (1H, d, J=2 Hz), 7.66 (2H, d, J=9 Hz), 7.98 (1H, dd, J=2 Hz, 8 Hz), 8.39 (2H, d, J=9 Hz)

(3) N-Benzyl-N-(2-methoxyphenyl)-1-(4-nitrophenyl)-1H-imidazol-2-amine

N-(2-Methoxyphenyl)-1-(4-nitrophenyl)-1H-imidazol-2-amine (80 mg, 0.26 mmol) obtained above was dissolved in dimethylformamide (3 mL), and 60% sodium hydride (11 mg, 0.29 mmol) was added to the solution under ice cooling. After the mixture was stirred for 10 minutes, benzyl bromide (37 μL, 0.31 mmol) was added to the mixture, and the resulting mixture was stirred at room temperature for 16 hours under a nitrogen atmosphere. The reaction mixture was diluted with ethyl acetate, and the organic layer was washed with water and saturated brine, and dried over sodium sulfate. The solvent was evaporated under reduced pressure, and then the residue was purified by silica gel column chromatography (chloroform/methanol=20/1) to obtain the title compound (67 mg, yield 64%).

$^1$H NMR (CDCl$_3$, 400 MHz) δ: 3.79 (3H, s), 4.82 (2H, s), 6.6-6.7 (3H, m), 6.8-6.9 (2H, m), 6.97 (1H, s), 7.2-7.3 (3H, m), 7.36 (2H, d, J=9 Hz), 7.50 (2H, d, J=8 Hz), 8.00 (2H, d, J=9 Hz)

(4) 5-[4-[2-[Benzyl(2-methoxyphenyl)amino]-1H-imidazol-1-yl]phenyl]-1,5-dihydro-2H-naphtho[1,2-b][1,4]diazepine-2,4(3H,5H)-dione By using N-benzyl-N-(2-methoxyphenyl)-1-(4-nitrophenyl)-1H-imidazol-2-amine (67 mg, 0.17 mmol) obtained above, a crude product of the title compound was obtained in the same manner as that of Example 73, (2), Example 3, (5), and (6).

(5) 5-[4-[2-[(2-Methoxyphenyl)amino]-1H-imidazol-1-yl]phenyl]-1, 5-dihydro-2H-naphtho[1,2-b][1,4]diazepine-2,4(3H,5H)-dione The crude product of 5-[4-[2-[benzyl(2-methoxyphenyl)amino]-1H-imidazol-1-yl]phenyl]-1,5-dihydro-2H-naphtho[1,2-b][1,4]diazepine-2,4(3H,5H)-dione obtained above was dissolved in acetic acid, and 10% palladium hydroxide-activated carbon (5 mg) was added to the solution under a nitrogen atmosphere. The resulting mixture was stirred at room temperature for 2 hours under a hydrogen atmosphere, and then the insoluble matter was separated by filtration, and washed with ethyl acetate. The organic layer was evaporated under reduced pressure, and the residue was neutralized with aqueous potassium carbonate. The resulting mixture was extracted with chloroform, the organic layer was dried over anhydrous sodium sulfate, the solvent was evaporated under reduced pressure, and then the residue was purified by silica gel column chromatography (chloroform/methanol=20/1) to obtain the title compound (2 mg, yield 9%) as a yellow amorphous substance.

$^1$H NMR (CDCl$_3$, 400 MHz) δ: 3.64 (2H, s), 3.78 (3H, s), 6.8-7.0 (7H, m), 7.4-7.5 (3H, m), 7.62 (1H, d, J=8 Hz), 7.66 (1H, d, J=3 Hz), 7.72 (1H, t, J=9 Hz), 7.89 (1H, d, J=8 Hz), 8.07 (1H, d, J=8 Hz), 8.12 (1H, d, J=8 Hz), 8.69 (1H, s)

Example 76

5-[4-[2-(Phenylamino)-1H-imidazol-1-yl]phenyl]-1H-naphtho[1,2-b][1,4]diazepine-2,4(3H,5H)-dione By using 2-bromo-1-(nitrophenyl)-1H-imidazole (400 mg, 1.49 mmol) obtained in Example 75, (1), and aniline (0.2 mL, 2.24 mmol), the title compound (2.3 mg) was obtained as a yellow amorphous substance in the same manner as that of Example 75, (2), (3), (4), and (5).

$^1$H NMR (CDCl$_3$, 400 MHz) δ: 3.63 (2H, s), 6.21 (1H, s), 6.87 (1H, d, J=2 Hz), 6.9-7.0 (1H, m), 6.96 (1H, d, J=1 Hz), 6.97 (1H, d, J=8 Hz), 7.2-7.3 (4H, m), 7.37 (2H, d, J=9 Hz), 7.45 (2H, d, J=9 Hz), 7.6-7.7 (2H, m), 7.72 (1H, t, J=7 Hz), 7.88 (1H, d, J=8 Hz), 8.13 (1H, d, J=8 Hz), 8.87 (1H, s)

Example 77

5-[4-[1-[(6-Methoxypyridin-2-yl)methyl]-1H-imidazol-2-yl]phenyl]-1H-naphtho[1,2-b][1,4]diazepine-2,4(3H,5H)-dione hydrochloride

(1) 5-[4-[1-[(6-Methoxypyridin-2-yl)methyl]-1H-imidazol-2-yl]phenyl]-1H-naphtho[1,2-b][1,4]diazepine-2,4(3H,5H)-dione By using 2-(4-nitrophenyl)-1H-imidazole [Heterocycles, 76, 507 (2008)], and 2-(bromomethyl)-6-methoxypyridine, the title compound (48.4 mg) was obtained in the same manner as that of Example 23, (1), (2), (3), (4), and (5).

$^1$H NMR (CDCl$_3$, 400 MHz) δ: 3.62 (2H, s), 3.86 (3H, s), 5.18 (1H, d, J=16 Hz), 5.23 (1H, d, J=16 Hz), 6.58 (1H, d, J=7 Hz), 6.66 (1H, d, J=8 Hz), 6.99 (1H, d, J=9 Hz), 7.09 (1H, d, J=1 Hz), 7.20 (1H, d, J=1 Hz), 7.32 (2H, d, J=8 Hz), 7.52 (1H, t, J=8 Hz), 7.59 (1H, d, J=9 Hz), 7.60 (1H, d, J=7 Hz), 7.68 (1H, dt, J=1 Hz, 8 Hz), 7.72 (2H, d, J=9 Hz), 7.85 (1H, d, J=8 Hz), 8.14 (1H, d, J=8 Hz), 9.22 (1H, s)

(2) 5-[4-[1-[(6-Methoxypyridin-2-yl)methyl]-1H-imidazol-2-yl]phenyl]-1H-naphtho[1,2-b][1,4]diazepine-2,4(3H,5H)-dione hydrochloride By using 5-[4-[1-[(6-methoxypyridin-2-yl)methyl]-1H-imidazol-2-yl]phenyl]-1H-naphtho[1,2-b][1,4]diazepine-2,4(3H,5H)-dione (18.4 mg, 0.038 mmol) obtained above, the title compound (8.4 mg, yield 42%) was obtained as pale yellow powder in the same manner as that of Example 3, (7).

$^1$H NMR (DMSO-d$_6$, 400 MHz) δ: 3.19 (1H, d, J=12 Hz), 3.66 (3H, s), 3.77 (1H, d, J=12 Hz), 5.51 (2H, s), 6.79 (1H, d, J=8 Hz), 6.91 (1H, d, J=9 Hz), 7.03 (1H, d, J=7 Hz), 7.51 (2H, d, J=9 Hz), 7.63 (1H, t, J=7 Hz), 7.7-7.8 (3H, m), 7.9-8.0 (5H, m), 8.30 (1H, d, J=8 Hz), 10.97 (1H, s)

Example 78

5-[4-[1-[(6-Hydroxypyridin-2-yl)methyl]-1H-imidazol-2-yl]phenyl]-1H-naphtho[1,2-b][1,4]diazepine-2,4(3H,5H)-dione hydrochloride

(1) 5-[4-[1-[(6-Hydroxypyridin-2-yl)methyl]-1H-imidazol-2-yl]phenyl]-1H-naphtho[1,2-b][1,4]diazepine-2,4(3H,5H)-dione 5-[4-[1-[(6-Methoxypyridin-2-yl)methyl]-1H-imidazol-2-yl]phenyl]-1H-naphtho[1,2-b][1,4]diazepine-2,4(3H,5H)-dione (30 mg, 0.061 mmol) obtained in Example 77 was dissolved in acetonitrile (0.5 mL), chlorotrimethylsilane (32 μL, 0.25 mmol), and sodium iodide (22 mg, 0.15 mmol) were added to the solution, and the mixture was refluxed by heating at 70° C. for 16 hours under a nitrogen atmosphere. The reaction mixture was left to cool, and then diluted with ethyl acetate, the organic layer was washed with water and saturated brine, and the organic layer was dried over sodium sulfate. The solvent was evaporated under reduced pressure, and then the residue was purified by silica gel column chromatography (chloroform/methanol=20/1) to obtain the title compound (20 mg, yield 84%).

$^1$H NMR (CDCl$_3$, 400 MHz) δ: 3.6-3.7 (2H, m), 5.08 (1H, d, J=19 Hz), 5.17 (1H, d, J=19 Hz), 5.77 (1H, d, J=7 Hz), 6.39 (1H, d, J=9 Hz), 6.96 (1H, d, J=9 Hz), 7.06 (1H, d, J=1 Hz), 7.2-7.3 (1H, m), 7.3-7.4 (3H, m), 7.5-7.6 (4H, m), 7.74 (1H, t, J=7 Hz), 7.82 (1H, d, J=8 Hz), 8.46 (1H, d, J=9 Hz), 11.74 (1H, s), 14.02 (1H, s)

(2) 5-[4-[1-[(6-Hydroxypyridin-2-yl)methyl]-1H-imidazol-2-yl]phenyl]-1H-naphtho[1,2-b][1,4]diazepine-2,4(3H,5H)-dione hydrochloride By using 5-[4-[1-[(6-hydroxypyridin-2-yl)methyl]-1H-imidazol-2-yl]phenyl]-1H-naphtho[1,2-b][1,4]diazepine-2,4(3H,5H)-dione (20 mg, 0.042 mmol) obtained above, the title compound (17 mg, yield 79%) was obtained as pale yellow powder in the same manner as that of Example 3, (7).

$^1$H NMR (DMSO-d$_6$, 400 MHz) δ: 3.19 (1H, d, J=12 Hz), 3.77 (1H, d, J=12 Hz), 5.34 (2H, s), 6.43 (1H, d, J=7 Hz), 6.92 (1H, d, J=9 Hz), 7.4-7.5 (3H, m), 7.62 (1H, t, J=8 Hz), 7.69 (1H, t, J=8 Hz), 7.74 (1H, d, J=9 Hz), 7.8-8.0 (6H, m), 8.29 (1H, d, J=9 Hz), 10.98 (1H, s)

Example 79

5-[4-[2-(3-Fluorophenethyl)-1H-imidazol-1-yl]phenyl]-5,8,9,10-tetrahydroindeno[4,5-b][1,4]diazepine-2,4(1H,3H)-dione hydrochloride

(1) 5-[4-[2-(3-Fluorophenethyl)-1H-imidazol-1-yl]phenyl]-5,8,9,10-tetrahydroindeno[4,5-b][1,4]diazepine-2,4(1H,3H)-dione By using N$^1$-(4-nitro-2,3-dihydro-1H-inden-5-yl)benzene-1,4-diamine (400 mg, 1.48 mmol) obtained in Example 61, (1), and 3-(3-fluorophenyl)propionic acid (309 mg, 1.84 mmol), the title compound (80 mg) was obtained in the same manner as that of Example 3, (2), (4), (5), (6), Example 21, (1), (2), and (3).

$^1$H NMR (CDCl$_3$, 400 MHz) δ: 2.2-2.3 (2H, m), 2.9-3.1 (8H, m), 3.56 (2H, d, J=12 Hz), 6.7-6.8 (2H, m), 6.8-6.9 (2H, m), 6.96 (1H, d, J=1 Hz), 7.01 (1H, d, J=8 Hz), 7.1-7.2 (3H, m), 7.2-7.3 (3H, m), 8.79 (1H, s)

(2) 5-[4-[2-(3-Fluorophenethyl)-1H-imidazol-1-yl]phenyl]-5,8,9,10-tetrahydroindeno[4,5-b][1,4]diazepine-2,4(1H,3H)-dione hydrochloride By using 5-[4-[2-(3-fluorophenethyl)-1H-imidazol-1-yl]phenyl]-5,8,9,10-tetrahydroindeno[4,5-b][1,4]diazepine-2,4(1H,3H)-dione (80 mg, 0.166 mmol) obtained above, the title compound (70 mg, yield 82%) was obtained as pale yellow powder in the same manner as that of Example 3, (7).

$^1$H NMR (DMSO-d$_6$, 400 MHz) δ: 2.08 (2H, t, J=7 Hz), 2.8-2.9 (3H, m), 3.00 (2H, t, J=7 Hz), 3.11 (1H, d, J=12 Hz), 3.22 (3H, d, J=5 Hz), 3.67 (1H, d, J=12 Hz), 6.68 (1H, d, J=8 Hz), 6.86 (1H, d, J=7 Hz), 6.91 (1H, d, J=10 Hz), 7.04 (2H, d, J=8 Hz), 7.28 (1H, q, J=7 Hz), 7.41 (2H, d, J=8 Hz), 7.51 (2H, d, J=8 Hz), 7.84 (1H, s), 7.91 (1H, s), 10.29 (1H, s)

Example 80

5-[4-[2-[(Phenylamino)methyl]-1H-imidazol-1-yl]phenyl]-1H-naphtho[1,2-b][1,4]diazepine-2,4(3H,5H)-dione

By using N$^1$-(1-nitronaphthalen-2-yl)benzene-1,4-diamine (300 mg, 1.18 mol) obtained in Example 3, (1), and N-phenylglycine (155 mg, 1.18 mmol), the title compound (1.1 mg) was obtained as white powder in the same manner as that of Example 3, (2), (4), (5), (6), Example 21, (1), (2), and (3).

$^1$H NMR (DMSO-d$_6$, 400 MHz) δ: 3.65 (2H, s), 4.3-4.4 (3H, m), 6.62 (2H, d, J=8 Hz), 6.73 (1H, t, J=7 Hz), 7.04 (1H, d, J=9 Hz), 7.10 (1H, d, J=1 Hz), 7.1-7.2 (3H, m), 7.4-7.5 (4H, m), 7.6-7.8 (3H, m), 7.90 (1H, d, J=8 Hz), 8.08 (1H, d, J=8 Hz), 8.40 (1H, s)

Example 81

3-[[2-[4-[2,4-Dioxo-3,4-dihydro-1H-naphtho[2,1-b][1,4]diazepin-5-(2H)-yl]phenyl]-1H-imidazol-1-yl]methyl]benzonitrile

By using 2-(4-nitrophenyl)-1H-imidazole [Heterocycles, 76, 507 (2008)], and 3-cyanobenzyl chloride, the title compound (164 mg) was obtained as a slightly brown amorphous substance in the same manner as that of Example 23, (1), (2), (3), (4), and (5).

$^1$H NMR (CDCl$_3$, 400 MHz) δ: 3.61 (2H, s), 5.30 (2H, s), 6.98 (2H, d, J=9 Hz), 7.2-7.3 (5H, m), 7.47 (1H, t, J=8 Hz), 7.54 (2H, d, J=9 Hz), 7.6-7.6 (3H, m), 7.78 (1H, t, J=2 Hz), 7.87 (1H, d, J=8 Hz), 8.07 (1H, d, J=8 Hz), 8.47 (1H, s)

Example 82

3-[[2-[4-[2,4-Dioxo-3,4-dihydro-1H-naphtho[2,1-b][1,4]diazepin-5-(2H)-yl]phenyl]-1H-imidazol-1-yl]methyl]benzamide

By using 3-[[2-[4-[2,4-dioxo-3,4-dihydro-1H-naphtho[2,1-b][1,4]diazepin-5-(2H)-yl]phenyl]-1H-imidazol-1-yl]methyl]benzonitrile obtained in Example 81, the title compound (35 mg) was obtained as a slightly brown amorphous substance in the same manner as that of Example 45.

$^1$H NMR (CDCl$_3$, 400 MHz) δ: 3.58 (1H, d, J=12 Hz), 3.61 (1H, d, J=12 Hz), 5.25 (2H, s), 5.75 (1H, br s), 6.25 (1H, br s), 6.97 (1H, d, J=9 Hz), 7.03 (1H, d, J=1 Hz), 7.19 (2H, d, J=9 Hz), 7.26 (2H, d, J=8 Hz), 7.40 (1H, t, J=7 Hz), 7.46 (1H, s), 7.51 (2H, d, J=8 Hz), 7.5-7.6 (2H, m), 7.6-7.7 (2H, m), 7.85 (1H, d, J=8 Hz), 8.11 (1H, d, J=8 Hz), 8.84 (1H, br s)

Example 83

5-[4-[(2-(3-Fluoro-2-methoxyphenyl)ethyl)-1H-imidazol-1-yl]phenyl]-1H-naphtho[1,2-b][1,4]diazepine-2,4(3H,5H)-dione hydrochloride By using $N^1$-(1-nitronaphthalen-2-yl)benzene-1,4-diamine obtained in Example 3, (1), and 3-(3-fluoro-2-methoxyphenyl)propionic acid, the title compound (67.3 mg) was obtained as a white amorphous substance in the same manner as that of Example 3, (2), (4), (5), (6), (7), Example 21, (1), (2), and (3).

$^1$H NMR (CD$_3$OD, 400 MHz) δ: 2.9-3.0 (2H, m), 3.2-3.3 (2H, m), 3.39 (1H, d, J=12 Hz), 3.76 (3H, s), 3.78 (1H, d, J=15 Hz), 6.74 (1H, d, J=7 Hz), 6.88-6.95 (1H, m), 7.0-7.1 (1H, m), 7.08 (1H, d, J=9 Hz), 7.36 (2H, d, J=9 Hz), 7.50 (2H, d, J=9 Hz), 7.6-7.7 (5H, m), 7.93 (1H, d, J=8 Hz), 8.26 (1H, d, J=9 Hz)

Example 84

(P2X4 Receptor Antagonist Activity)
(Test Method)

The P2X4 receptor antagonist activities of the compounds of the present invention were measured as follows.

The 1321N1 cells stably expressing human P2X4 receptor were seeded on a 96-well plate, cultured under the conditions of 37° C. and 5% CO$_2$ for 24 hours, and then used for intracellular calcium measurement. Fura-2 AM, which is a calcium fluorescent indicator, was used for the intracellular calcium measurement. Fura-2 AM dissolved in an assay buffer was added to the cells, the cells were left standing at room temperature for 45 minutes so that Fura-2 AM was incorporated into the cells, and then the plate was used for the fluorescence measurement. The treatment of the cells with each test substance was performed 15 minutes before the addition of ATP, and inflow of calcium into the cells as a response induced by the addition of ATP was measured over time by using a microplate reader. The ratio of fluorescence values obtained with excitation lights of 340 nm and 380 nm was used as an index of the change of intracellular calcium level, and the inhibitory activity of the test substance was calculated on the basis of the comparison with the value obtained in the absence of the test substance (control). The test results are shown in Table 29.
(Test Results)

TABLE 29

| Test compound | Inhibitory activity IC$_{50}$ (μM) |
| --- | --- |
| Example 1 | 0.025 |
| Example 2 | 0.037 |
| Example 3 | 0.38 |
| Example 4 | 0.044 |
| Example 11 | 0.077 |
| Example 19 | 0.32 |
| Example 21 | 0.078 |
| Paroxetine | 4.0 |

As clearly seen from the results shown in Table 29, it was found that the compounds of the present invention have superior P2X4 receptor antagonist activity.

Example 85

(P2X4 Receptor Antagonist Activity)
(Test Method)

In the same manner as that of Example 84, the P2X4 receptor antagonist activities of the compound of Example 22 and other compounds were measured. The results are shown in Tables 30 and 31.
(Test Results)

TABLE 30

| Test compound | Inhibitory activity IC$_{50}$ (μM) |
| --- | --- |
| Example 22 | 0.091 |
| Example 23 | 0.30 |
| Example 25 | 0.082 |
| Example 27 | 0.078 |
| Example 30 | 0.27 |
| Example 31 | 0.051 |
| Example 32 | 0.18 |
| Example 37 | 0.079 |
| Example 38 | 0.55 |
| Example 40 | 0.63 |
| Example 41 | 0.65 |
| Example 42 | 0.092 |
| Example 43 | 0.053 |
| Example 43 | 0.19 |
| Example 47 | 0.094 |
| Example 50 | 3.7 |
| Example 51 | 1.7 |
| Example 53 | 0.59 |
| Example 54 | 0.19 |

TABLE 31

| Test compound | Inhibitory activity IC$_{50}$ (μM) |
| --- | --- |
| Example 55 | 0.34 |
| Example 57 | 0.13 |
| Example 61 | 0.074 |
| Example 62 | 0.088 |
| Example 64 | 0.52 |
| Example 65 | 0.13 |
| Example 66 | 0.55 |
| Example 67 | 0.053 |
| Example 68 | 0.79 |
| Example 69 | 5.4 |
| Example 71 | 0.59 |
| Example 72 | 3.4 |
| Example 73 | 0.32 |
| Example 74 | 2.5 |
| Example 79 | 0.039 |
| Example 80 | 1.3 |
| Example 83 | 0.087 |
| Paroxetine | 4.0 |

As clearly seen from the results shown in Tables 30 and 31, it was found that the compounds of the present invention described in the examples have superior P2X4 receptor antagonist activity.

Example 86

(Analgesic Activity)

The analgesic activities of the compounds of the present invention were measured by the following method.
Preparation of Mouse Neuropathic Pain Model Mouse neuropathic pain model was prepared according to the method of Tozaki-Saitoh H. et al. (Tozaki-Saitoh H., Tsuda M., Miyata H., Ueda K., Kohsaka S. and Inoue K.;

P2Y12 Receptors in Spinal Microglia Are Required for Neuropathic Pain after Peripheral Nerve Injury. Neuroscience, 28(19): 4949-4956 (2008)). Under isoflurane anesthesia, back hair of mice was extensively shaved, the shaved parts were wiped with rubbing alcohol, and the mice were fixed in the prone position on a heating pad. The skins were cut and opened along the dorsal median line on the upper and lower sides of the head end of the sacroiliac bone in a length of about 1 cm each, with confirming the head end of the bone with fingers. The left lateral paravertebral muscle was separated in the sacral region, and then the ligament was separated. The sacroiliae rim and the upper part thereof were cut and opened along the pyramid, and the transverse process of the first sacral vertebra (S1) was confirmed. The transverse process of S1 was removed, the fourth lumber nerve (L4) running just under the transverse process was confirmed and cut, and the operative wound was sutured. Mice that showed a 50% pain threshold of 0.6 g or lower in the von Frey filament test were defined to have allodynia.

Measurement of Pain Threshold and Calculation Method of 50% Threshold

The measurement of the pain threshold was performed after the mice were moved to a cage for pain threshold measurement, and they substantially no longer showed exploratory behavior. The pain threshold (paw withdrawal threshold (g)) was measured by stimulating the soles of mice with each of seven von Frey filaments (Stoelting Co., TOUCH-TEST SENSORY EVALUATOR) that gave different stimulation strengths, and determining presence or absence of withdrawal response. The 50% threshold was calculated according to the up down method with reference to the method of Chaplan et al. (Chaplan S R, Bach F W, Pogrel J W, Chung J M, Yaksh T L: Quantitative assessment of tactile allodynia in the rat paw, J. Neurosci. Method, 53:55-63 (1994)).

Evaluation Method and Results

For evaluation of efficacy, each of the compounds described in Examples 21 and 42 was orally administered to the neuropathic pain model mice with a sonde for oral administration in mice, and effect thereof on the pain threshold measured in the von Frey filament test was observed. As a result, it was observed that oral administration of 30 mg/kg of each of the compounds described in Examples 21 and 42 increased the pain threshold of diseased limb, and provided significant difference with respect to the vehicle administration group. From the results shown in FIG. 1, it became clear that the compound described in Example 21 has superior analgesic activity.

EXPLANATION OF SYMBOLS

In FIG. 1, the open circles (○) indicate the results obtained with administration of the vehicle (n=16), and the black solid circles (●) indicate the results obtained with administration of 30 mg/kg of the compound described in Example 21 (n=13).

What is claimed is:

1. A compound represented by the following formula (I), a tautomer or a stereoisomer of the compound, or a pharmacologically acceptable salt thereof, or a solvate of any of the foregoing:

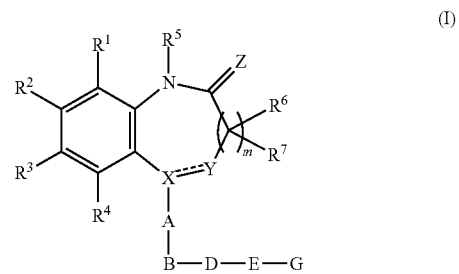

wherein
$R^1$ and $R^2$ bind together to form a condensed ring selected from a naphthalene ring, a quinoline ring, an isoquinoline ring, a tetrahydronaphthalene ring, an indane ring, a tetrahydroquinoline ring, and a tetrahydroisoquinoline ring, together with the benzene ring to which they bind, the ring constituted by $R^1$ and $R^2$, bound to each other, together with the carbon atoms to which $R^1$ and $R^2$ bind may be substituted with the same or different 1 to 4 substituents selected from an alkyl group having 1 to 8 carbon atoms, a cycloalkyl group having 3 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, an amino group, an alkylamino group having 1 to 8 carbon atoms, a dialkylamino group having 2 to 8 carbon atoms, a carboxamido group having 2 to 8 carbon atoms, a carboxyl group, an alkanoyl group having 2 to 8 carbon atoms, an alkoxycarbonyl group in which the alkoxy moiety has 1 to 8 carbon atoms, and an aralkyl group in which the aryl moiety has 6 to 10 carbon atoms and the alkylene moiety has 1 to 8 carbon atoms,
$R^3$ and $R^4$ may be the same or different, and represent a hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, an amino group, an alkylamino group having 1 to 8 carbon atoms, a dialkylamino group having 2 to 8 carbon atoms, a carboxamido group having 2 to 8 carbon atoms, a carboxyl group, an alkanoyl group having 2 to 8 carbon atoms, an alkoxycarbonyl group in which the alkoxy moiety has 1 to 8 carbon atoms, or an aralkyl group in which the aryl moiety has 6 to 10 carbon atoms and the alkylene moiety has 1 to 8 carbon atoms,
$R^5$ represents a hydrogen atom, an alkyl group having 1 to 8 carbon atoms, an alkenyl group having 2 to 8 carbon atoms, an alkyl group having 1 to 8 carbon atoms and substituted with 1 to 3 halogen atoms, an alkyl group having 1 to 8 carbon atoms and substituted with a hydroxyl group, or an aralkyl group in which the aryl moiety has 6 to 10 carbon atoms and the alkylene moiety has 1 to 8 carbon atoms,
$R^6$ and $R^7$ may be the same or different, and represent a hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, or an amino group, X represents N, Y represents C(=O), the double line consisting of the solid line and the broken line represents a single bond or double bond, Z represents O, A represents a benzene ring, a pyridine ring, a pyrimidine ring, a pyridazine ring, a thiophene ring, a furan ring, a pyrazole ring, a imidazole ring, a quinoline ring, a benzimidazole ring, or an indane ring, which may have the same or different 1 to 4 substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, an amino group, an alkylamino group having 1 to 8 carbon atoms, and a dialkylamino group having 2 to 8 carbon atoms, as a substituent, B represents an atomic bond, D represents a tetrazole ring or an imidazole ring, which may have the same or different 1 to 4 substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, an amino group, an alkylamino group having 1 to 8 carbon atoms, and a dialkylamino group having 2 to 8 carbon atoms, as a substituent, E represents —$(CR^9R^{10})_n$-T-, wherein $R^9$ and $R^{10}$ may be the same or different, and represent a hydrogen atom, a hydroxyl group, or an alkyl group having 1 to 8 carbon atoms, n represents an integer of 0 to 8, and T represents O, S, $NR^{11}$, or an atomic bond, wherein $R^{11}$ represents a hydrogen atom, G represents a benzene ring, a pyridine ring, a imidazole ring, a pyrrole ring, a pyrazole ring, a thiophene ring, a furan ring, a thiazole ring, an oxazole ring, a pyrimidine ring, a pyridazine ring, a pyrazine ring, a naphthalene ring, a quinoline ring, a quinazoline ring, an indole ring, an indoline ring, a piperazine ring, a piperidine ring, a morpholine ring, or a 5- to 8-membered cycloalkyl ring, which may have the same or different 1 to 5 substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, an amino group, an alkylamino group having 1 to 8 carbon atoms, a dialkylamino group having 2 to 8 carbon atoms, carbamoyl group, and methanesulfonyl group, as a substituent, and m represents an integer of 0 to 2.

2. The compound according to claim 1, a tautomer or a stereoisomer of the compound, or a pharmacologically acceptable salt thereof, or a solvate of any of the foregoing, wherein m is 1.

3. The compound according to claim 1, a tautomer or a stereoisomer of the compound, or a pharmacologically acceptable salt thereof, or a solvate of any of the foregoing, wherein $R^1$ and $R^2$ bind together to form a naphthalene ring together with the benzene ring to which they bind, and the naphthalene ring may be substituted with the same or different 1 to 4 substituents selected from an alkyl group having 1 to 8 carbon atoms, a cycloalkyl group having 3 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, an amino group, an alkylamino group having 1 to 8 carbon atoms, and a dialkylamino group having 2 to 8 carbon atoms.

4. The compound according to claim 1, a tautomer or a stereoisomer of the compound, or a pharmacologically acceptable salt thereof, or a solvate of any of the foregoing, wherein $R^3$ and $R^4$ may be the same or different, and are a hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, an amino group, an alkylamino group having 1 to 8 carbon atoms, or a dialkylamino group having 2 to 8 carbon atoms.

5. The compound according to claim 1, a tautomer or a stereoisomer of the compound, or a pharmacologically acceptable salt thereof, or a solvate of any of the foregoing, wherein $R^5$ is a hydrogen atom.

6. The compound according to claim 1, a tautomer or a stereoisomer of the compound, or a pharmacologically acceptable salt thereof, or a solvate of any of the foregoing, wherein $R^6$ and $R^7$ are hydrogen atoms.

7. The compound according to claim 1, a tautomer or a stereoisomer of the compound, or a pharmacologically acceptable salt thereof, or a solvate of any of the foregoing, wherein A is a benzene ring or a pyridine ring, which may have the same or different 1 to 4 substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, an amino group, an alkylamino group having 1 to 8 carbon atoms, and a dialkylamino group having 2 to 8 carbon atoms, as a substituent.

8. The compound according to claim 1, a tautomer or a stereoisomer of the compound, or a pharmacologically acceptable salt thereof, or a solvate of any of the foregoing, wherein D binds to A via a nitrogen atom.

9. The compound according to claim 1, a tautomer or a stereoisomer of the compound, or a pharmacologically acceptable salt thereof, or a solvate of any of the foregoing, wherein E is an alkylene chain having 1 to 5 carbon atoms.

10. The compound according to claim 1, a tautomer or a stereoisomer of the compound, or a pharmacologically acceptable salt thereof, or a solvate of any of the foregoing, wherein G is a benzene ring, a pyridine ring, an imidazole ring, a pyrrole ring, a pyrazole ring, a pyrimidine ring, a pyridazine ring, a pyrazine ring, or a 5- to 7-membered cycloalkyl ring, which may have the same or different 1 to 5 substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, a amino group, an alkylamino group having 1 to 8 carbon atoms, a dialkylamino group having 2 to 8 carbon atoms, a carbamoyl group, and a methanesulfonyl group, as a substituent.

11. The compound according to claim 1, a tautomer or a stereoisomer of the compound, or a pharmacologically acceptable salt thereof, or a solvate of any of the foregoing, wherein:
$R^1$ and $R^2$ bind together to form a naphthalene ring, or an indane ring together with the benzene ring to which they bind,
the naphthalene ring or indane ring may be substituted with the same or different 1 to 4 substituents selected from an alkyl group having 1 to 8 carbon atoms, a cycloalkyl group having 3 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, an amino group, an alkylamino group having 1 to 8 carbon atoms, a dialkylamino group having 2 to 8 carbon atoms, a carboxamido group having 2 to 8 carbon atoms, a carboxyl group, an alkanoyl group having 2 to 8 carbon atoms, an alkoxycarbonyl group in which the alkoxy moiety has 1 to 8 carbon atoms, and an aralkyl group in which the aryl moiety has 6 to 10 carbon atoms and the alkylene moiety has 1 to 8 carbon atoms,
$R^3$ and $R^4$ may be the same or different, and are a hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, an amino group, an alkylamino group having 1 to 8 carbon atoms, a dialkylamino group having 2 to 8 carbon atoms, a carboxamido group having 2 to 8 carbon atoms, a carboxyl group, an alkanoyl group having 2 to 8 carbon atoms, an alkoxycarbonyl group in which the alkoxy moiety has 1 to 8 carbon atoms, or an aralkyl group in which the aryl moiety has 6 to 10 carbon atoms and the alkylene moiety has 1 to 8 carbon atoms,
$R^5$ is a hydrogen atom, an alkyl group having 1 to 8 carbon atoms, an alkenyl group having 2 to 8 carbon atoms, an alkyl group having 1 to 8 carbon atoms and substituted with 1 to 3 halogen atoms, an alkyl group having 1 to 8 carbon atoms and substituted with a hydroxyl group, or an aralkyl group in which the aryl moiety has 6 to 10 carbon atoms and the alkylene moiety has 1 to 8 carbon atoms,
$R^6$ and $R^7$ may be the same or different, and are a hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, or an amino group,
X is N,
Y is C(=O),
the double line consisting of the solid line and the broken line is a single bond,
Z is O,
A is a benzene ring or a pyridine ring, which may have the same or different 1 to 4 substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, a amino group, an alkylamino group having 1 to 8 carbon atoms, and a dialkylamino group having 2 to 8 carbon atoms, as a substituent,
B is an atomic bond,
D is a tetrazole ring or an imidazole ring, which may have the same or different 1 or 2 substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, an amino group, an alkylamino group having 1 to 8 carbon atoms, and a dialkylamino group having 2 to 8 carbon atoms, as a substituent,
D binds to A via nitrogen atom of D, and binds to E via carbon atom of D,
E is —$(CR^9R^{10})_n$—, wherein $R^9$ and $R^{10}$ may be the same or different, and are a hydrogen atom, a hydroxyl group, or an alkyl group having 1 to 8 carbon atoms, and n is an integer of 1 to 8,
G is a benzene ring, which may have the same or different 1 to 5 substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, an amino group, an alkylamino group having 1 to 8 carbon atoms, a dialkylamino group having 2 to 8 carbon atoms, a carbamoyl group, and a methanesulfonyl group, as a substituent, and
m is 1.

12. The compound according to claim 1, a tautomer or a stereoisomer of the compound, or a pharmacologically acceptable salt thereof, or a solvate of any of the foregoing, wherein:
$R^1$ and $R^2$ bind together to form a naphthalene ring or an indane ring together with the benzene ring to which they bind,
$R^3$ and $R^4$ are hydrogen atoms,
$R^5$ is a hydrogen atom,
$R^6$ and $R^7$ are hydrogen atoms, X is N,
Y is C(=O),
the double line consisting of the solid line and the broken line is a single bond,
Z is O,
A is a benzene ring, which may have the same or different 1 to 4 substituents selected from an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, a amino group, an alkylamino group having 1 to 8 carbon atoms, and a dialkylamino group having 2 to 8 carbon atoms, as a substituent,
B is an atomic bond,
D is a tetrazole ring or an imidazole ring, which may have 1 or 2 substituents selected from an alkyl group having 1 to 8 carbon atoms, and an alkyl group having 1 to 8 carbon atoms and substituted with 1 to 3 halogen atoms, as a substituent,
D binds to A via nitrogen atom of D, and binds to E via carbon atom of D,
E is —(CR$^9$R$^{10}$)$_n$—, wherein R$^9$ and R$^{10}$ are the same or different, and are a hydrogen atom or an alkyl group having 1 to 8 carbon atoms, and n is an integer of 1 to 4,
G is a benzene ring, which may have the same or different 1 to 5 substituents selected from an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, an amino group, an alkylamino group having 1 to 8 carbon atoms, a dialkylamino group having 2 to 8 carbon atoms, and a carbamoyl group, as a substituent, and
m is 1.

13. The compound according to claim 1, a tautomer or a stereoisomer of the compound, or a pharmacologically acceptable salt thereof, or a solvate of any of the foregoing, wherein:
R$^1$ and R$^2$ bind together to form a naphthalene ring or an indane ring together with the benzene ring to which they bind,
R$^3$ and R$^4$ are hydrogen atoms,
R$^5$ is hydrogen atom,
R$^6$ and R$^7$ are hydrogen atoms,
X is N,
Y is C(=O),
the double line consisting of the solid line and the broken line is a single bond,
Z is O,
A is a benzene ring, which may have the same or different 1 to 4 substituents selected from an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, a amino group, a an alkylamino group having 1 to 8 carbon atoms, and a dialkylamino group having 2 to 8 carbon atoms, as a substituent,
B is an atomic bond,
D is an imidazole ring, which may have 1 or 2 substituents selected from an alkyl group having 1 to 8 carbon atoms, and an alkyl group having 1 to 8 carbon atoms and substituted with 1 to 3 halogen atoms, as a substituent,
D binds to A at the 2-position of the imidazole ring, and binds to E via a nitrogen atom of the imidazole ring,
E is —(CR$^9$R$^{10}$)$_n$—, wherein R$^9$ and R$^{10}$ are the same or different, and are a hydrogen atom or an alkyl group having 1 to 8 carbon atoms, and n is an integer of 1 to 4,
G is a benzene ring, which may have the same or different 1 to 5 substituents selected from an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, an amino group, an alkylamino group having 1 to 8 carbon atoms, a dialkylamino group having 2 to 8 carbon atoms, and a carbamoyl group, as a substituent, and
m is 1.

14. A compound represented by the following formula (II), a tautomer or a stereoisomer of the compound, or a pharmacologically acceptable salt thereof, or a solvate of any of the foregoing:

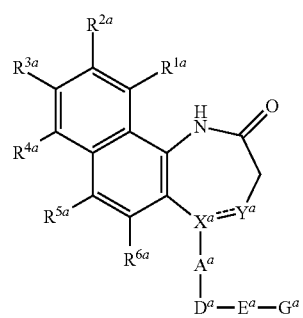

(II)

wherein, in the formula, R$^{1a}$, R$^{2a}$, R$^{3a}$, R$^{4a}$, R$^{5a}$, and, R$^{6a}$ may be the same or different, and represent a hydrogen atom, an alkyl group having 1 to 8 carbon atoms, a cycloalkyl group having 3 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, an amino group, an alkylamino group having 1 to 8 carbon atoms, a dialkylamino group having 2 to 8 carbon atoms, a carboxamido group having 2 to 8 carbon atoms, a carboxyl group, an alkanoyl group having 2 to 8 carbon atoms, an alkoxycarbonyl group in which the alkoxy moiety has 1 to 8 carbon atoms, a phenyl group which may be substituted, a pyridyl group which may be substituted, or an aralkyl group in which the aryl moiety has 6 to 10 carbon atoms and the alkylene moiety has 1 to 8 carbon atoms,
X$^a$ represents N,
Y$^a$ represents C(=O),
the double line consisting of the solid line and the broken line represents a single bond or double bond, $A^a$ represents a benzene ring, a pyridine ring, a pyrimidine ring, a pyridazine ring, a thiophene ring, a furan ring, a pyrazole ring, an imidazole ring, a quinoline ring, a benzimidazole ring, or an indane ring, which may have the same or different 1 to 4 substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, an amino group, an alkylamino group having 1 to 8 carbon atoms, and a dialkylamino group having 2 to 8 carbon atoms, as a substituent, $D^a$ represents a a tetrazole ring or an imidazole ring, which may have the same or different 1 to 4 substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, an amino group, an alkylamino group having 1 to 8 carbon atoms, and a dialkylamino group having 2 to 8 carbon atoms, as a substituent, $E^a$ represents $-(CR^{9a}R^{10a})_p-T^a-$, wherein $R^{9a}$ and $R^{10a}$ are the same or different, and represent a hydrogen atom, a hydroxyl group, or an alkyl group having 1 to 8 carbon atoms, p represents an integer of 0 to 8, and $T^a$ represents O, S, $NR^{11a}$, or an atomic bond, wherein $R^{11a}$ represents a hydrogen atom, and $G^a$ represents a benzene ring, a pyridine ring, a imidazole ring, a pyrrole ring, a pyrazole ring, a thiophene ring, a furan ring, a thiazole ring, an oxazole ring, a pyrimidine ring, a pyridazine ring, a pyrazine ring, a naphthalene ring, a quinoline ring, a quinazoline ring, an indole ring, an indoline ring, a piperazine ring, a piperidine ring, a morpholine ring, or a 5- to 8-membered cycloalkyl ring, which may have the same or different 1 to 5 substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, an amino group, an alkylamino group having 1 to 8 carbon atoms, a dialkylamino group having 2 to 8 carbon atoms, carbamoyl group, and methanesulfonyl group, as a substituent.

15. The compound according to claim 14, a tautomer or a stereoisomer of the compound, or a pharmacologically acceptable salt thereof, or a solvate of any of the foregoing, wherein $R^{1a}$, $R^{2a}$, $R^{3a}$, $R^{4a}$, $R^{5a}$, and $R^{6a}$ may be the same or different, and represent a hydrogen atom, an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, or a hydroxyl group.

16. The compound according to claim 14, a tautomer or a stereoisomer of the compound, or a pharmacologically acceptable salt thereof, or a solvate of any of the foregoing, wherein $A^a$ is a benzene ring or a pyridine ring, which may have the same or different 1 to 4 substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, an amino group, an alkylamino group having 1 to 8 carbon atoms, and a dialkylamino group having 2 to 8 carbon atoms, as a substituent.

17. The compound according to claim 14, a tautomer or a stereoisomer of the compound, or a pharmacologically acceptable salt thereof, or a solvate of any of the foregoing, wherein $A^a$ is a benzene ring, which may have the same or different 1 to 4 substituents selected from an alkyl group having 1 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, and an amino group, as a substituent.

18. The compound according to claim 14, a tautomer or a stereoisomer of the compound, or a pharmacologically acceptable salt thereof, or a solvate of any of the foregoing, wherein $D^a$ is a tetrazole ring.

19. The compound according to claim 14, a tautomer or a stereoisomer of the compound, or a pharmacologically acceptable salt thereof, or a solvate of any of the foregoing, wherein $D^a$ binds to $A^a$ via a nitrogen atom.

20. The compound according to claim 14, a tautomer or a stereoisomer of the compound, or a pharmacologically acceptable salt thereof, or a solvate of any of the foregoing, wherein $E^a$ is an alkylene chain having 1 to 5 carbon atoms.

21. The compound according to claim 14, a tautomer or a stereoisomer of the compound, or a pharmacologically acceptable salt thereof, or a solvate of any of the foregoing, wherein $G^a$ is a benzene ring, a pyridine ring, an imidazole ring, a pyrrole ring, a pyrazole ring, a pyrimidine ring, a pyridazine ring, a pyrazine ring, or a 5- to 7-membered cycloalkyl ring, which may have the same or different 1 to 5 substituents selected from an alkyl group having 1 to 8 carbon atoms, an alkenyl group having 2 to 8 carbon atoms, an alkoxy group having 1 to 8 carbon atoms, an alkyl group having 1 to 8 carbon atoms and substituted with 1 to 3 halogen atoms, an alkoxy group having 1 to 8 carbon atoms and substituted with 1 to 3 halogen atoms, a halogen atom, a hydroxyl group, a nitro group, a cyano group, an amino group, an alkylamino group having 1 to 8 carbon atoms, a dialkylamino group having 2 to 8 carbon atoms, a carbamoyl group, and a methanesulfonyl group, as a substituent.

22. A P2X4 receptor antagonist, or a prophylactic or therapeutic agent for nociceptive pain, inflammatory pain, or neuropathic pain, comprising the compound according to claim 1, a tautomer or a stereoisomer of the compound, or a pharmacologically acceptable salt thereof, or a solvate of any of the foregoing as an active ingredient, and further comprising at least one pharmaceutically acceptable excipient.

* * * * *

UNITED STATES PATENT AND TRADEMARK OFFICE
CERTIFICATE OF CORRECTION

PATENT NO. : 9,873,683 B2
APPLICATION NO. : 14/903382
DATED : January 23, 2018
INVENTOR(S) : S. Sakuma et al.

Page 1 of 1

It is certified that error appears in the above-identified patent and that said Letters Patent is hereby corrected as shown below:

In the Claims

Column 109, Line 10 (Claim 10, Line 14) please change "a amino" to -- an amino --
Column 110, Line 21 (Claim 11, Line 75) please change "a amino" to -- an amino --
Column 111, Line 13 (Claim 12, Line 23) please change "a amino" to -- an amino --
Column 111, Line 64 (Claim 13, Line 23) please change "a amino" to -- an amino --
Column 111, Line 65 (Claim 13, Line 24) please change "group, a an" to -- group an --
Column 113, Line 16 (Claim 14, Line 44) please change "represents a a" to -- represents a --

Signed and Sealed this
Thirty-first Day of July, 2018

Andrei Iancu
*Director of the United States Patent and Trademark Office*